United States Patent
Smith et al.

(10) Patent No.: US 10,046,045 B2
(45) Date of Patent: Aug. 14, 2018

(54) VACCINE COMPOSITIONS AND USES THEREOF

(71) Applicants: THE REGENTS OF THE UNIVERSITY OF MICHIGAN, Ann Arbor, MI (US); PURDUE RESEARCH FOUNDATION, West Lafayette, IN (US)

(72) Inventors: Janet L. Smith, Ann Arbor, MI (US); David L. Akey, Ann Arbor, MI (US); W. Clay Brown, Chelsea, MI (US); Richard J Kuhn, West Lafayette, IN (US)

(73) Assignees: THE REGENTS OF THE UNIVERSITY OF MICHIGAN, Ann Arbor, MI (US); PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/106,085

(22) PCT Filed: Dec. 19, 2014

(86) PCT No.: PCT/US2014/071552
§ 371 (c)(1),
(2) Date: Jun. 17, 2016

(87) PCT Pub. No.: WO2015/095735
PCT Pub. Date: Jun. 25, 2015

(65) Prior Publication Data
US 2016/0317644 A1    Nov. 3, 2016

Related U.S. Application Data

(60) Provisional application No. 61/919,407, filed on Dec. 20, 2013.

(51) Int. Cl.
*A61K 39/12*    (2006.01)
*A61K 39/39*    (2006.01)
*C12N 7/00*    (2006.01)

(52) U.S. Cl.
CPC ............ *A61K 39/12* (2013.01); *A61K 39/39* (2013.01); *C12N 7/00* (2013.01); *C12N 2770/24122* (2013.01); *C12N 2770/24134* (2013.01); *C12N 2770/24171* (2013.01)

(58) Field of Classification Search
None
See application file for complete search history.

(56) References Cited

U.S. PATENT DOCUMENTS

2009/0010961 A1    1/2009    Kinney et al.
2009/0226478 A1    9/2009    Flamand et al.

FOREIGN PATENT DOCUMENTS

WO    2015095735    6/2015

OTHER PUBLICATIONS

International Search Report of priority App. No. PCT/US2014/071552, dated Jul. 10, 2015. 15 pages.
Akey et al., "A new structural form in the SAM/metal-dependent o-methyltransferase family: MycE from the mycinamicin biosynthetic pathway." J Mol Biol. Oct. 21, 2011;413(2):438-50.
Alcon-Lepoder et al., "Secretion of flaviviral non-structural protein NS1: from diagnosis to pathogenesis." Novartis Found Symp. 2006;277:233-47; discussion 247-53.
Avirutnan et al., "Antagonism of the complement component C4 by flavivirus nonstructural protein NS1." J Exp Med. Apr. 12, 2010;207(4):793-806.
Avirutnan et al., "Binding of flavivirus nonstructural protein NS1 to C4b binding protein modulates complement activation." J Immunol. Jul. 1, 2011;187(1):424-33.
Brown et a., "New ligation-independent cloning vectors compatible with a high-throughput platform for parallel construct expression evaluation using baculovirus-infected insect cells." Protein Expr Purif. May 2011;77(1):34-45.
Cheng et al., "Proteomic analysis of endothelial cell autoantigens recognized by anti-dengue virus nonstructural protein 1 antibodies." Exp Biol Med (Maywood). Jan. 2009;234(1):63-73.
Chung et al., "West Nile virus nonstructural protein NS1 inhibits complement activation by binding the regulatory protein factor H." Proc Natl Acad Sci U S A. Dec. 12, 2006;103(50):19111-6.
Civril et al., "The RIG-I ATPase domain structure reveals insights into ATP-dependent antiviral signalling." EMBO Rep. Oct. 28, 2011;12(11):1127-34.
Falconar "Monoclonal antibodies that bind to common epitopes on the dengue virus type 2 nonstructural-1 and envelope glycoproteins display weak neutralizing activity and differentiated responses to virulent strains: implications for pathogenesis and vaccines." Clin Vaccine Immunol. Mar. 2008;15(3):549-61.
Falconar "The dengue virus nonstructural-1 protein (NS1) generates antibodies to common epitopes on human blood clotting, integrin/adhesin proteins and binds to human endothelial cells: potential implications in haemorrhagic fever pathogenesis." Arch Viral. 1997;142(5):897-916.
Gutsche et al., "Secreted dengue virus nonstructural protein NS1 is an atypical barrel-shaped high-density ipoprotein." Proc Natl Acad Sci U S A. May 10, 2011;108(19):8003-8.
Henchal et al., "Synergistic interactions of anti-NS1 monoclonal antibodies protect passively immunized mice from lethal challenge with dengue 2 virus." J Gen Virol. Aug. 1988;69 ( Pt 8):2101-7.
Kabsch et al., "XDS" Acta Crystallogr D Biol Crystallogr. Feb. 1, 2010; 66(Pt 2): 125-132.
Khromykh et al., "cis- and trans-acting elements in flavivirus RNA replication." J Virol. Apr. 2008;74(7):3253-63.

(Continued)

*Primary Examiner* — Stacy B Chen
(74) *Attorney, Agent, or Firm* — Casimir Jones, S.C.; Tanya Arenson

(57) ABSTRACT

The present disclosure relates to nonstructural protein 1 (NS1) from flaviviruses and uses thereof. In particular, the present invention relates to diagnostic and therapeutic uses of NS1 to treat and prevent disease caused by flaviviruses.

8 Claims, 10 Drawing Sheets

(56) References Cited

OTHER PUBLICATIONS

Kinney et al., "Construction of infectious cDNA clones for dengue 2 virus: strain 16681 and its attenuated vaccine lerivative, strain PDK-53." Virology. Apr. 14, 1997;230(2):300-8.

Krishna et al., "Virus-specific cytolytic antibodies to nonstructural protein 1 of Japanese encephalitis virus effect reduction of virus output from infected cells." J Virol. May 2009;83(10):4766-77.

Lindenbach et al., "Genetic interaction of flavivirus nonstructural proteins NS1 and NS4A as a determinant of replicase function." J Virol. Jun. 1999;73(6):4611-21.

Lindenbach et al., "Molecular biology of flaviviruses." Adv Virus Res. 2003;59:23-61.

Lindenbach et al., "trans-Complementation of yellow fever virus NS1 reveals a role in early RNA replication." J Virol. Dec. 1997;71(12):9608-17.

Liu et al., "Molecular mimicry of human endothelial cell antigen by autoantibodies to nonstructural protein 1 of dengue virus." J Biol Chem. Mar. 18, 2011;286(11):9726-36.

Mackenzie et al., "Immunolocalization of the dengue virus nonstructural glycoprotein NS1 suggests a role in viral RNA replication." Virology. Jun. 1, 1996;220(1):232-40.

Motz et al.,"Paramyxovirus V proteins disrupt the fold of the RNA sensor MDA5 to inhibit antiviral signaling." Science. Feb. 8, 2013;339(6120):690-3.

Muller et al., "Structure of the dengue virus glycoprotein non-structural protein 1 by electron microscopy and single-particle analysis." J Gen Virol. Apr. 2012;93(Pt 4):771-9.

Muller et al., "The flavivirus NS1 protein: molecular and structural biology, immunology, role in pathogenesis and application as a diagnostic biomarker." Antiviral Res. May 2013;98(2):192-208.

Sheldrick et al., "Experimental phasing with SHELXC/D/E: combining chain tracing with density modification" Acta Crystallogr D Biol Crystallogr. Apr. 1, 2010; 66(Pt 4): 479-485.

Suthar et al. "West Nile virus infection and immunity." Nat Rev Microbiol. Feb. 2013;11(2):115-28.

Vita et al., "The immune epitope database 2.0." Nucleic Acids Res. Jan. 2010;38(Database issue):D854-62.

Westaway et al., "Ultrastructure of Kunjin virus-infected cells: colocalization of NS1 and NS3 with double-stranded RNA, and of NS2B with NS3, in virus-induced membrane structures." J Virol. Sep. 1997;71(9):6650-61.

Youn et al., "Evidence for a genetic and physical interaction between nonstructural proteins NS1 and NS4B that modulates replication of West Nile virus." J Virol. Jul. 2012;86(13):7360-71.

Young et al., "An antigen capture enzyme-linked immunosorbent assay reveals high levels of the dengue virus protein NS1 in the sera of infected patients." J Clin Microbiol. Mar. 2000;38(3):1053-7.

A. 1st gel filtration

B. neg stain EM after 1st SEC

C. 2nd gel filtration

D. neg stain EM after 2nd SEC

Figure 11

VACCINE COMPOSITIONS AND USES THEREOF

CROSS-REFERENCE TO RELATED APPLICATION

The present application is a 371 U.S. National Phase Entry of pending International Application No. PCT/US2014/071552, filed Dec. 19, 2014, which claims priority to U.S. Provisional Application Ser. No. 61/919,407, filed Dec. 20, 2013, each of which is hereby incorporated by reference in their entireties.

STATEMENT REGARDING FEDERALLY SPONSORED RESEARCH OR DEVELOPMENT

This invention was made with government support under AI055672 awarded by the National Institutes of Health. The government has certain rights in the invention.

FIELD OF THE INVENTION

The present disclosure relates to nonstructural protein 1 (NS1) from flaviviruses and uses thereof. In particular, the present invention relates to diagnostic and therapeutic uses of NS1 to treat and prevent disease caused by flaviviruses.

BACKGROUND OF THE INVENTION

The Flaviviridae are a family of positive, single-stranded, enveloped RNA viruses. They are found in arthropods, primarily ticks and mosquitoes, and can occasionally infect humans. Members of this family belong to a single genus, Flavivirus, and cause widespread morbidity and mortality throughout the world. Some of the mosquitoes-transmitted viruses include: Yellow Fever, Dengue Fever, Japanese encephalitis, and West Nile viruses. Other Flaviviruses are transmitted by ticks and are responsible of encephalitis and hemorrhagic diseases: Tick-borne Encephalitis (TBE), Kyasanur Forest Disease (KFD) and Al-Khurma disease, and Omsk hemorrhagic fever.

With incidence rates on the rise, worldwide dengue epidemics have become a major public health concern not only for those living in the tropics, but in Central America and the U.S. as well.

The successful yellow fever 17D vaccine, introduced in 1937, produced dramatic reductions in epidemic activity. Effective killed Japanese encephalitis and Tick-borne encephalitis vaccines were introduced in the middle of the 20th century. Unacceptable adverse events have prompted change from a mouse-brain killed Japanese encephalitis vaccine to safer and more effective second generation Japanese encephalitis vaccines. These may come into wide use to effectively prevent this severe disease in the huge populations of Asia—North, South and Southeast. The dengue viruses produce many millions of infections annually due to transmission by a successful global mosquito vector. As mosquito control has failed, several dengue vaccines are in varying stages of development. However, additional vaccines and other therapeutics against pathogenic Flaviviridae are needed.

SUMMARY OF THE INVENTION

The present disclosure relates to nonstructural protein 1 (NS1) from flaviviruses and uses thereof. In particular, the present invention relates to diagnostic and therapeutic uses of NS1 to treat and prevent disease caused by flaviviruses.

Embodiments of the present invention provide compositions for generating an immune response, comprising one or more NS1 polypeptides or peptides (e.g., including but not limited to, those described by SEQ ID NOs: 3382, peptides that are at least 80% (e.g., 85%, 90%, or 95%) identical to SEQ ID NOs: 3382, or variants, mimetics, or modified versions thereof); and b) a pharmaceutically acceptable carrier. In some embodiments, the composition further comprises an adjuvant.

In some embodiments, the present invention provides methods and uses of inducing an immune response towards a flavivirus or treating or preventing infection by a flavivirus in a subject, comprising: administering any of the aforementioned compositions to a subject, wherein the administering induces an immune response against a flavivirus or prevents or treats infection by the flavivirus. In some embodiments, the flavivirus, is, for example, dengue virus (e.g., serotypes 1-4), West Nile virus or Japanese encephalitis virus.

Additional embodiments provide a kit comprising any of the aforementioned compositions. In some embodiments, the kits further comprise a device for administering the composition to a subject.

Further embodiments provide a device for delivery of any of the aforementioned compositions. In some embodiments, the device is, for example, a syringe and needle, or an intranasal delivery device.

The present invention additional provides a method of identifying compounds that inhibit the binding of NS1 to liposmes, comprising: a) contacting a purified flavivirus NS1 polypeptide with a liposome and a test compound; and b) measuring the level of binding of the NS1 polypeptide to the liposome in the presence and absence of the test compound. In some embodiments, the NS1 polypeptide is present as a dimer.

The present invention further provides a agent that specifically binds to amino acids 159-162 of NS1 (e.g., an aptamer or an antibody). In some embodiments, the agent prevents or treats infection of a subject with a flavivivrus.

Additional embodiments are described herein.

DESCRIPTION OF THE FIGURES

Figure 11:
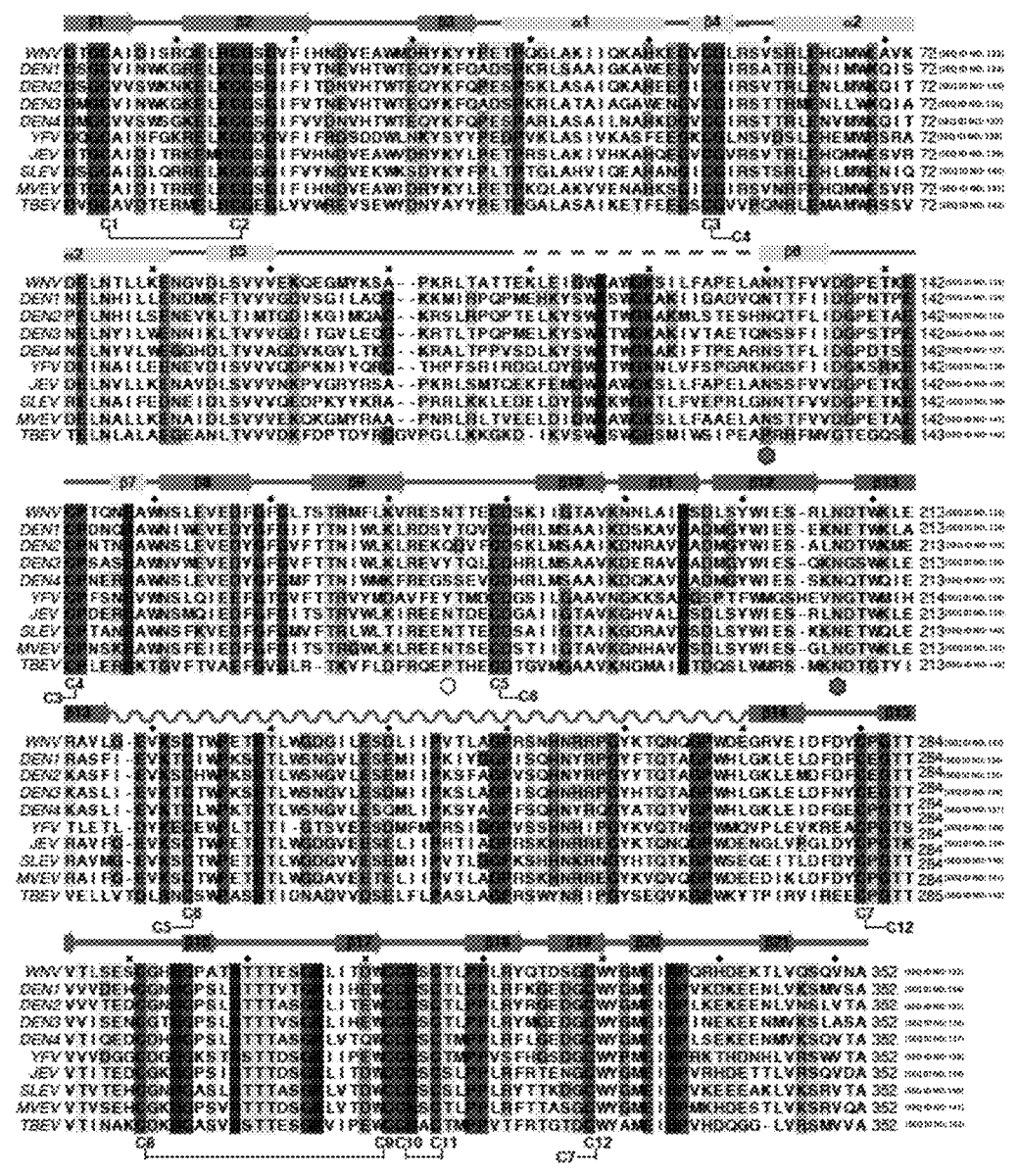

FIG. 11 shows secondary structure and sequence alignment of flavivirus NS1 proteins.

DEFINITIONS

Figure 1:
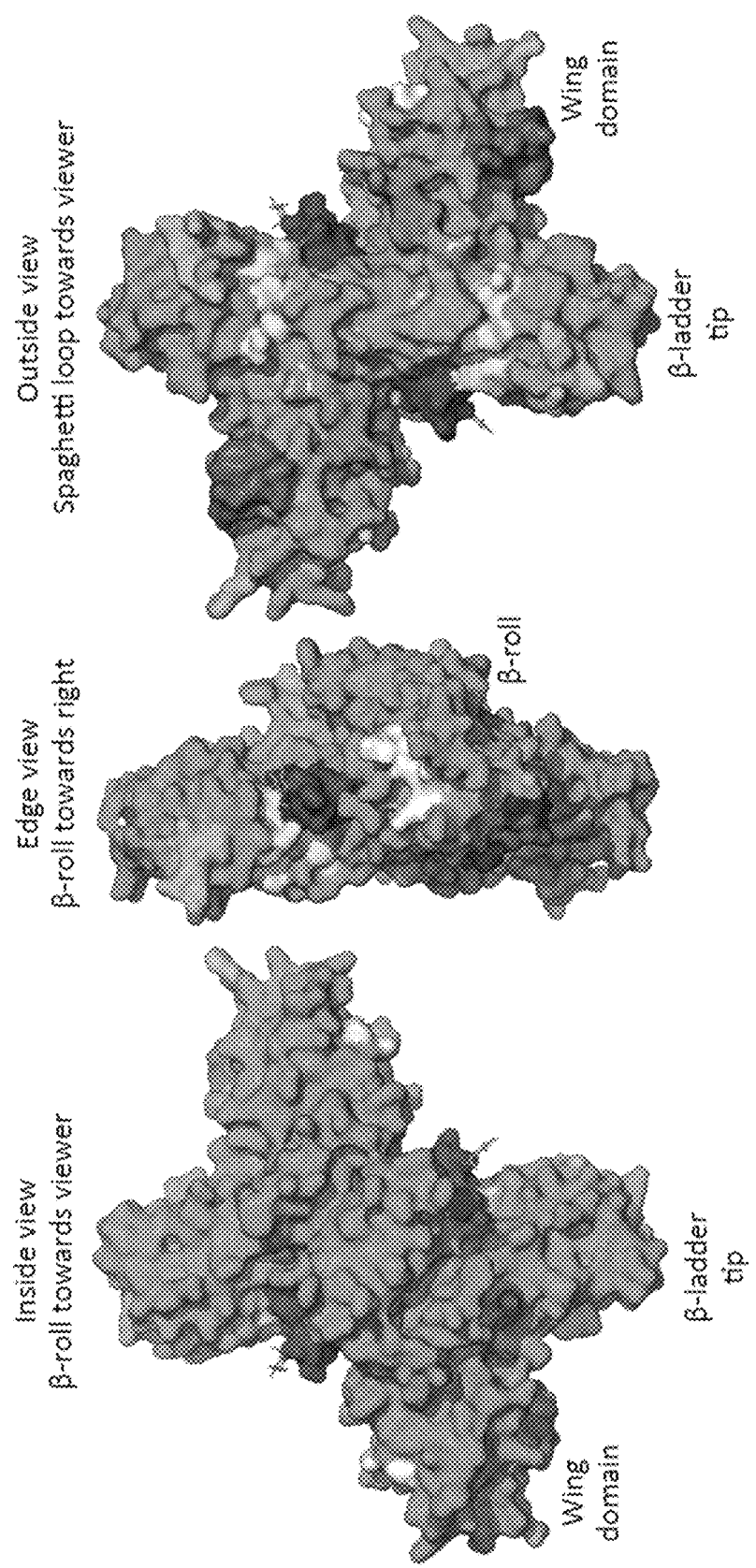
FIG. 1 shows the crystal structure of NS1.

As used herein, the terms "subject" and "patient" refer to any animal, such as a mammal like a dog, cat, bird, livestock, and preferably a human.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F' (ab)$_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments.

A molecule that "specifically binds to" or is "specific for" another molecule is one that binds to that particular molecule without substantially binding to any other molecule. As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the term "administration" refers to the act of giving a drug, prodrug, antibody, vaccine, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Co administration" refers to administration of more than one chemical agent or therapeutic treatment to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, "carriers" include pharmaceutically acceptable carriers, excipients, or stabilizers which are non-toxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "protein," "polypeptide," and "peptide" refer to a molecule comprising amino acids joined via peptide bonds. In general, "peptide" is used to refer to a sequence of 20 or less amino acids and "polypeptide" is used to refer to a sequence of greater than 20 amino acids.

As used herein, the term, "synthetic polypeptide," "synthetic peptide", and "synthetic protein" refer to peptides, polypeptides, and proteins that are produced by a recombinant process (i.e., expression of exogenous nucleic acid encoding the peptide, polypeptide, or protein in an organism, host cell, or cell-free system) or by chemical synthesis.

As used herein, the term "protein of interest" refers to a protein encoded by a nucleic acid of interest.

As used herein, the term "native" (or wild type) when used in reference to a protein refers to proteins encoded by the genome of a cell, tissue, or organism, other than one manipulated to produce synthetic proteins.

As used herein, "domain" (typically a sequence of three or more, generally 5 or 7 or more amino acids) refers to a portion of a molecule, such as proteins or the encoding nucleic acids, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as proteolytic activity. As such, a domain refers to a folded protein structure that retains its tertiary structure independently of the rest of the protein. Generally, domains are responsible for discrete functional properties of proteins, and in many cases may be added, removed or transferred to other proteins without loss of function of the remainder of the protein and/or of the domain.

A protein can have one, or more than one, distinct domains. For example, a domain can be identified, defined or distinguished by homology of the sequence therein to related family members, such as homology to motifs that define a protease domain or a gla domain. In another example, a domain can be distinguished by its function, such as by proteolytic activity, or an ability to interact with a biomolecule, such as DNA binding, ligand binding, and dimerization. A domain independently can exhibit a biological function or activity such that the domain independently or fused to another molecule can perform an activity, such as, for example proteolytic activity or ligand binding. A domain can be a linear sequence of amino acids or a non-linear sequence of amino acids. Many polypeptides contain a plurality of domains. Some domains are known and can be identified by those of skill in the art. It is to be understood that it is well within the skill in the art to recognize particular domains by name. If needed, appropriate software can be employed to identify domains.

As used herein, the term "host cell" refers to any eukaryotic cell (e.g., mammalian cells, avian cells, amphibian cells, plant cells, fish cells, insect cells, yeast cells), and bacteria cells, and the like, whether located in vitro or in vivo (e.g., in a transgenic organism). The term "host cell" refers to any cell capable of replicating and/or transcribing and/or translating a heterologous gene. Thus, a "host cell" refers to any eukaryotic or prokaryotic cell, whether located in vitro or in vivo. For example, host cells may be located in a transgenic animal.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "isolated" when used in relation to a nucleic acid or polypeptide or protein refers to a nucleic acid or polypeptide or protein sequence that is identified and separated from at least one contaminant nucleic acid or polypeptide or protein with which it is ordinarily associated in its natural source. Isolated nucleic acids or polypeptides or proteins are molecules present in a form or setting that is different from that in which they are found in nature. In contrast, non-isolated nucleic acids or polypeptides or proteins are found in the state in which they exist in nature.

The term "antigen" refers to a molecule (e.g., a protein, glycoprotein, lipo-protein, lipid, nucleic acid, or other substance) that is reactive with an antibody specific for a portion of the molecule.

The term "antigenic determinant" refers to that portion of an antigen that makes contact with a particular antibody (e.g., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (e.g., the "immunogen" used to elicit the immune response) for binding to an antibody.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

As used herein, a "vaccine" comprises one or more immunogenic antigens intentionally administered to induce acquired immunity in the recipient (e.g., a subject).

DETAILED DESCRIPTION OF THE INVENTION

The present disclosure relates to nonstructural protein 1 (NS1) from flaviviruses and uses thereof. In particular, the present invention relates to diagnostic and therapeutic uses of NS1 to treat and prevent disease caused by flaviviruses.

NS1 was initially identified as a viral antigen in sera of patients infected with dengue virus. NS1 exists in multiple oligomeric forms as well as within different compartments within infected host cells. Its involvement in the pathology of multiple flavivirus family members including, for example, dengue (DENV), yellow fever (YFV), Japanese encephalitis (JEV), West Nile (WNV), tick-borne encephalitis (TBE), St. Louis encephalitis (SLEV) and Murray Valley encephalitis (MVEV), has made it an important target for the development of viral therapeutics as well as vaccines to combat these infections diseases. Additionally the elevated levels of NS1 which circulate during the early stages of host infection have also supported the use of NS1 as a marker for early detection of viral infection.

The major bottle neck in the development of these therapeutics and diagnostics has been the lack of a clear and accurate crystal structure as well as a method to produce large quantities of protein. Lack of a procedure to make recombinant NS1 has hampered research on its role in both replication and immune defense and pathogenesis. Embodiments of the present disclosure provide a method to produce large quantities of recombinant, pure NS1 in native, active form.

Some of the early attempts at developing vaccines for NS1 lead to antibodies which attacked important host self-proteins because of homology between the unknown structural motifs present in NS1 which the antibodies detected. Embodiments of the present disclosure further provide a 3-dimensional structure of NS1 through protein crystallography. FIG. 1 shows three crystal structures of NS1 from two flaviviruses.

In some embodiments, the present disclosure provides secreted NS1 (sNS1) and uses thereof. The sNS1 assembles into a 10-nm lipid bound hexamer with a hydrophobic interior and flexible loops and glycosylation sites facing outside. During infection NS1 can direct complement-based lysis of virus-infected cells. Hexameric NS1 is taken up by hepatocytes and this enhances the level of flavivirus infection. This makes the NS1 oligomer a useful vaccine target. The 3D structures (See e.g., FIG. 1) provide detailed information about the regions of NS1 that are accessible in the sNS1 hexamer and which are not, allowing for selection of antigens.

Peptide sequences from NS1 that find use in inducing immune responses are shown below. Aligned sequences for six flavivirus NS1 proteins are shown for each peptide useful for inducing immune response.

In some embodiments, one or more of the following peptides (or peptides that are at least 80%, at least 90%, or at least 95% identical to the peptides), mimetics, variants, modified (e.g., comprising one or more modified amino acids) are utilized to induce immune responses and other applications. In some embodiments, polypeptides or peptides comprising the following peptides are utilized.

In some embodiments, the present disclosure contemplates peptides comprising one or more amino acid substitutions relative to the following sequences. In some embodiments, substitutions are conservative or non-conservative substitutions.

The peptides are mapped onto the 3D structure in FIG. 1.

```
                Regions that vary among DEN1/2/3/4 NS1

Region 1: Within the wing domain
DENV1: Q66466_27_388/40-52 KRLSAAIGKAWEE (SEQ ID NO: 1)
DENV2: I0AXR0-191_552/40-52 SKLASAIQKAHEE (SEQ ID NO: 2)
DENV3: gi:130437/40-52 KRVATAIAGAWEN (SEQ ID NO: 3)
DENV4: gi:74486/40-52 ARLASAILNAHKD (SEQ ID NO: 4)

Region 2: Flexible loop within wing domain
DENV1: Q66466 27 388/99-112 QGRKMIGPQPMEHK (SEQ ID NO: 5)
DENV2: I0AXR0-191 552/99-112 VGKRSLQPQPTELR (SEQ ID NO: 6)
DENV3: gi:130437/99-112 QGKRTLTPQPMELK (SEQ ID NO: 7)
DENV4: gi:74486/99-112 KGKRALTPPVSDLK (SEQ ID NO: 8)

Region 3: Within the wing domain
DENV1: Q66466_27_388/139-147 NTPECPDDQ (SEQ ID NO: 9)
DENV2: I0AXR0-191_552/139-147 ETAECPNTN (SEQ ID NO: 10)
DENV3: gi:130437/139-147 STPECPSAS (SEQ ID NO: 11)
DENV4: gi:74486/139-147 DTSECPNER (SEQ ID NO: 12)

Region 4: Connector sub-domain of wing
DENV1: Q66466_27_388/174-182 SYTQVCDPR (SEQ ID NO: 13)
DENV2: I0AXR0-191_552/174-182 KQDVFCDSK (SEQ ID NO: 14)
DENV3: gi:130437/174-182 VYTQLCDHR (SEQ ID NO: 15)
DENV4: gi:74486/174-182 GSSEVCDHR (SEQ ID NO: 16)

Region 5: Glycosylation site in β-ladder
DENV1: Q66466_27_388/205-213 EKN-ETWKLA (SEQ ID NO: 17)
DENV2: I0AXR0-191_552/205-213 ALN-DTWKIE (SEQ ID NO: 18)
DENV3: gi:130437/205-213 QKN-GSWKLE (SEQ ID NO: 19)
DENV4: gi:74486/205-213 SKN-QTWQIE (SEQ ID NO: 20)

Region 6: Within spaghetti loop
DENV1: Q66466_27_388/246-251 IYGGPI (SEQ ID NO: 21)
DENV2: I0AXR0-191_552/246-251 NLAGPV (SEQ ID NO: 22)
DENV3: gi:130437/246-251 SLAGPI (SEQ ID NO: 23)
DENV4: gi:74486/246-251 SYAGPF (SEQ ID NO: 24)

Region 7: Within spaghetti loop
DENV1: Q66466_27_388/256-265 YRPGYSTQTA (SEQ ID NO: 25)
DENV2: I0AXR0-191_552/256-265 NRPGYYTQTA (SEQ ID NO: 26)
DENV3: gi:130437/256-265 HRPGYHTQTA (SEQ ID NO: 27)
DENV4: gi:74486/256-265 YRQGYATQTV (SEQ ID NO: 28)

Region 8: Within C-terminal tip of β-ladder
DENV1: Q66466_27_388/286-293 VVDEHCGN (SEQ ID NO: 29)
DENV2: I0AXR0-191_552/286-293 VVTEDCGN (SEQ ID NO: 30)
DENV3: gi:130437/286-293 VISENCGT (SEQ ID NO: 31)
DENV4: gi:74486/286-293 TIQEDCDH (SEQ ID NO: 32)
```

-continued

Exemplary peptides useful for inducing immune responses

Region 1: β-roll-residues 1-29
DEN1   1 DSGCVINWKGRELKCGSGIFVTNEVHTWT  29 (SEQ ID NO: 33)
DEN2   1 DSGCVVSWKNKELKCGSGIFITDNVHTWT  29 (SEQ ID NO: 34)
DEN3   1 DMGCVINWKGKELKCGSGIFVTNEVHTWT  29 (SEQ ID NO: 35)
DEN4   1 DMGCVVSWSGKELKCGSGIFVVDNVHTWT  29 (SEQ ID NO: 36)
WNV    1 DTGCAIDISRQELRCGSGVFIHNDVEAWM  29 (SEQ ID NO: 37)
JEV    1 DTGCAIDITRKEMRCGSGIFVHNDVEAWV  29 (SEQ ID NO: 38)

Region 2: Floppy loop in the wing domain-residues 108-128
DEN1 108 PMEYKYSWKSWGKAKIIGADVQ 128 (SEQ ID NO: 39)
DEN2 108 PTELKYSWKTWGKAKMLSTESH 128 (SEQ ID NO: 40)
DEN3 108 PMELKYSWKTWGLAKIVTAETQ 128 (SEQ ID NO: 41)
DEN4 108 VSDLKYSWKTWGKAKIFTPEAR 128 (SEQ ID NO: 42)
WNV  108 TEKLEIGWKAWGKSILFAPELA 128 (SEQ ID NO: 43)
JEV  108 QEKFEMGWKAWGKSLLFAPELA 128 (SEQ ID NO: 44)

Region 3: Wing domain-residues 30-174
DEN1  30 EQYKFQADSPKRLSAAIGKAWEEGVCGIRSATRLENIMWKQISNELNHIL
79 (SEQ ID NO: 45)
DEN2  30 EQYKFQPESPSKLASAIQKAHEEGICGIRSVTRLENLMWKQITPELNHIL
79 (SEQ ID NO: 46)
DEN3  30 EQYKFQADSPKRVATAIAGAWENGVCGIRSTTRMENLLWKQIANELNYIL
79 (SEQ ID NO: 47)
DEN4  30 EQYKFQPESPARLASAILNAHKDGVCGIRSTTRLENVMWKQITNELNYVL
79 (SEQ ID NO: 48)
WNV   30 DRYKYYPETPQGLAKIIQKAHKEGVCGLRSVSRLEHQMWEAVKDELNTLL
79 (SEQ ID NO: 49)
JEV   30 DRYKYLPETPRSLAKIVHKAHQEGVCGVRSVTRLEHQMWESVRDELNVLL
79 (SEQ ID NO: 50)
DEN1  80 LENDMKFTVVVGDVSGILAQGKKMIRPQPMEYKYSWKSWGKAKIIGADVQ
129 (SEQ ID NO: 51)
DEN2  80 SENEVKLTIMTGDIKGIMQAGKRSLRPQPTELKYSWKTWGKAKMLSTESH
129 (SEQ ID NO: 52)
DEN3  80 WENDIKLTVVVGDITGVLEQGKRTLTPQPMELKYSWKTWGLAKIVTAETQ
129 (SEQ ID NO: 53)
DEN4  80 WEGGHDLTVVAGDVKGVLTKGKRALTPPVSDLKYSWKTWGKAKIFTPEAR
129 (SEQ ID NO: 54)
WNV   80 KENGVDLSVVVEKQEGMYKSAPKRLTATTEKLEIGWKAWGKSILFAPELA
129 (SEQ ID NO: 55)
JEV   80 KENAVDLSVVVNKPVGRYRSAPKRLSMTQEKFEMGWKAWGKSLLFAPELA
129 (SEQ ID NO: 56)
DEN1 130 NSTFIIDGPNTPECPDDQRAWNIWEVEDYGFGIFTTNIWLKLRDS 174
(SEQ ID NO: 57)
DEN2 130 NQTFLIDGPETAECPNTNRAWNSLEVEDYGFGVFTTNIWLKLKEK 174
(SEQ ID NO: 58)
DEN3 130 NSSFIIDGPSTPECPSASRAWNVWEVEDYGFGVFTTNIWLKLREV 174
(SEQ ID NO: 59)
DEN4 130 NSTFLIDGPDTSECPNERRAWNSLEVEDYGFGMFTTNIWMKFREG 174
(SEQ ID NO: 60)
WNV  130 NNTFVVDGPETKECPTQNRAWNSLEVEDFGFGLTSTRMFLKVRES 174
(SEQ ID NO: 61)
JEV  130 NSSFVVDGPETKECPDERRAWNSMQIEDFGFGITSTRVWLKIREE 174
(SEQ ID NO: 1) (SEQ ID NO: 62)

Region 4: Most exposed region of spaghetti loop-residues 232-240
DEN1 232 WSNGVLESE 240 (SEQ ID NO: 63)
DEN2 232 WSNGVLESE 240 (SEQ ID NO: 64)
DEN3 232 WSNGVLESD 240 (SEQ ID NO: 65)
DEN4 232 WSNGVLESQ 240 (SEQ ID NO: 66)
WNV  232 WGDGVLESD 240 (SEQ ID NO: 67)
JEV  232 WGDGVEESE 240 (SEQ ID NO: 68)

Region 5: C-terminal tip of β-ladder-residues 265-352
DEN1 265 AGPWHLGKLELDFDLCEGTTVVVDEHCGNRGPSLRTTTVTGKIIHEWCCR
314 (SEQ ID NO: 69)
DEN2 265 TGPWHLGKLEMDFDFCDGTTVVVTEDCGNRGPSLRTTTASGKLITEWCCR
314 (SEQ ID NO: 70)
DEN3 265 AGPWHLGKLELDFNYCEGTTVVISENCGTRGPSLRTTTVSGKLIHEWCCR
314 (SEQ ID NO: 71)
DEN4 265 VGPWHLGKLEIDFGECPGTTVTIQEDCDHRGPSLRTTTASGKLVTQWCCR
314 (SEQ ID NO: 72)
WNV  265 QGPWDEGRVEIDFDYCPGTTVTLSESCGHRGPATRTTTESGKLITDWCCR
314 (SEQ ID NO: 73)
JEV  265 QGPWDENGLVPGLDYCPGTKVTITEDCGKRGPSIRTTTDSGKLITDWCCR
314 (SEQ ID NO: 74)
DEN1 315 SCTLPPLRFKGEDGCWYGMEIRPVKEKEENLVKSMVSA 352
(SEQ ID NO: 75)

-continued

```
DEN2  315  SCTLPPLRYRGEDGCWYGMEIRPLKEKEENLVNSLVTA  352
(SEQ ID NO: 76)
DEN3  315  SCTLPPLRYMGEDGCWYGMEIRPINEKEENMVKSLASA  352
(SEQ ID NO: 77)
DEN4  315  SCTMPPLRFLGEDGCWYGMEIRPLSEKEENMVKSQVTA  352
(SEQ ID NO: 78)
WNV   315  SCTLPPLRYQTDSGCWYGMEIRPQRHDEKTLVQSQVNA  352  (SEQ ID NO: 79)
JEV   315  SCSLPPLRFRTENGCWYGMEIRPVRHDETTLVRSQVDA  352  (SEQ ID NO: 80)

Sequences above are from:
WNV NY99 (Crystal structure)
DEN2 16681 (Crystal structure)
DEN1 GZ/80 strain (Genbank GI: 13540387)
DEN3 Philippines/H87/1956 (Genbank GI: 130437 P27915.1)
DEN4 no strain given (Genbank AFG45436 GI: 12018172 AF326826.6)
JEV K94P05 (Genbank GI: 5231233)
```

```
WNV NY99 sequence in crystal structure:
                                                          (SEQ ID NO: 81)
DTGCAIDISRQELRCGSGVFIHNDVEAWMDRYKYYPETPQGLAKIIQKAHKEGVCGLRSV   60

SRLEHQMWEAVKDELNTLLKENGVDLSVVVEKQEGMYKSAPKRLTATTEKLEIGWKAWGK  120

SILFAPELANNTFVVDGPETKECPTQNRAWNSLEVEDFGFGLTSTRMFLKVRESNTTECD  180

SKIIGTAVKNNLAIHSDLSYWIESRLNDTWKLERAVLGEVKSCTWPETHTLWGDGILESD  240

LIIPVTLAGPRSNHNRRPGYKTQNQGPWDEGRVEIDFDYCPGTTVTLSESCGHRGPATRT  300

TTESGKLITDWCCRSCTLPPLRYQTDSGCWYGMEIRPQRHDEKTLVQSQVNA         352

DEN2 16681 sequence in crystal structure:
                                                          (SEQ ID NO: 82)
DSGCVVSWKNKELKCGSGIFITDNVHTWTEQYKFQPESPSKLASAIQKAHEEGICGIRSV   60

TRLENLMWKQITPELNHILSENEVKLTIMTGDIKGIMQAGKRSLRPQPTELKYSWKTWGK  120

AKMLSTESHNQTFLIDGPETAECPNTNRAWNSLEVEDYGFGVFTTNIWLKLKEKQDVFCD  180

SKLMSAAIKDNRAVHADMGYWIESALNDTWKIEKASFIEVKNCHWPKSHTLWSNGVLESE  240

MIIPKNLAGPVSQHNYRPGYHTQITGPWHLGKLEMDFDFCDGTTVVVTEDCGNRGPSLRT  300

TTASGKLITEWCCRSCTLPPLRYRGEDGCWYGMEIRPLKEKEENLVNSLVTA         352
```

I. Compositions Comprising NS1

In some embodiments, the present disclosure provides compositions for inducing immune responses (e.g., vaccines) comprising NS1 polypeptides or fragments thereof. NS1 interacts with components of the adaptive and innate immune systems. A major complication in vaccine development is the involvement of NS1 both in immune system evasion and in pathogenesis, e.g., some antibodies offer protection while some are implicated in disease pathogenesis. For example, an epitope at amino acids 311-330 of NS1 has been identified that is shared with a number of host components including the ATP synthase β chain, protein disulfide isomerase, vimentin and heat shock protein 60.

The present disclosure is not limited to a particular NS1 polypeptide, peptide or fragment thereof. In some embodiments, compositions comprise one or more NS1 peptides identified using the crystal structure described in FIG. 1. In some embodiments, the choice of peptide is based on the specific flavivirus that the vaccine targets. In some embodiments, compositions comprise one or more of the peptides described in SEQ ID NOs: 33-80, peptides that are at least 80%, 85%, 90%, or 95% identical to SEQ ID NOs: 33-80, or mimetics of the peptides described in SEQ ID NOs: 33-80. In some embodiments, one or more amino acids of the peptides in SEQ ID NOs: 33-80 is modified.

The compositions find use in preventing and/or treating infection by a variety of flavivirus pathogens. Examples include, but are not limited to, dengue virus (types 1, 2, 3 and 4), West Nile virus and Japanese encephalitis virus.

In some embodiments, compositions comprise one or more NS1 peptides or fragments thereof, and a pharmaceutically compatible carrier. Suitable carriers are, e.g., phosphate-buffered common salt solutions, water, emulsions, e.g. oil/water emulsions, wetting agents, sterile solutions, etc. The compositions are administered orally or parenterally. The methods of parenteral administration comprise the topical, intra-arterial, intramuscular, subcutaneous, intramedullary, intrathekal, intraventricular, intravenous, intraperitoneal, or intranasal administration. The suitable dose is determined by the attending physician and depends on different factors, e.g. the patient's age, sex and weight, the kind of administration etc.

In one aspect, vaccines or vaccine components are used to immunize mice to produce hybridomas. In some embodiments, the vaccine is for an infectious disease. Infectious diseases for which a vaccine may be constructed include but are not limited to viral diseases (e.g., flavivirus diseases). In some embodiments, the vaccine is for human use and in some embodiments it is for vaccination of animals, e.g., livestock, companion animals, and any other type of animal (fish, wildlife, etc.). Said vaccines can further also be applied in vitro to cells derived from a subject (e.g., a patient) to cause APC binding and presentation; said cells may then be returned to the host (subject, patient) of origin.

In some embodiments, nucleic acids expressing the NS1 polypeptides are present in a host cell in vitro for the production of the NS1 polypeptides. Recombinant methods for producing polypeptides in a cell culture are well known in the art. For example, in some embodiments, the polypeptides are expressed in a bacterial culture such as a culture of E. coli and the polypeptides are purified and isolated from the culture to provide the vaccine. In some embodiments, the host cell is a eukaryotic cell kept in cell culture (e.g., transfected into NSO cells, 293E cells and Cos-7 cells) and may or may not by a transformed cell in some embodiments.

In one embodiment, compositions are administered parenterally. In another embodiment compositions are administered to a mucosal surface such as the nasal cavity or other mucosa. In another particular embodiment, compositions are administered orally so as to permit presentation to the buccal or gastrointestinal mucosa. In some forms of oral administration compositions are encapsulated in an enteric capsule or gel capsule. In yet other embodiments compositions are provided in a chewable form. When the delivery is to a non-human animal, compositions can be incorporated into a bait or foodstuff. In some embodiments, compositions are applied topically to the skin.

The present disclosure is not limited by the particular formulation of a composition comprising a NS1 peptide. Indeed, a composition of the present disclosure may comprise one or more different agents in addition to the NS1 peptide or polypeptide. These agents or cofactors include, but are not limited to, adjuvants, surfactants, additives, buffers, solubilizers, chelators, oils, salts, therapeutic agents, drugs, bioactive agents, and antimicrobial agents (e.g., antibiotics, antivirals, etc.). In some embodiments, a vaccine composition comprises an agent or co-factor that enhances the ability of the antigenic unit to induce an immune response (e.g., an adjuvant). In some preferred embodiments, the presence of one or more co-factors or agents reduces the amount of antigenic unit required for induction of an immune response (e.g., a protective immune response (e.g., protective immunization)). In some embodiments, the presence of one or more co-factors or agents is used to skew the immune response towards a cellular (e.g., T-cell mediated) or humoral (e.g., antibody-mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995, incorporated by reference herein in its entirety for all purposes. The present invention is not limited by the type of adjuvant utilized (e.g., for use in a composition (e.g., a pharmaceutical composition)). For example, in some embodiments, suitable adjuvants include an aluminium salt such as aluminium hydroxide gel (e.g., alum) or aluminium phosphate. In some embodiments, an adjuvant may be a salt of calcium, iron, or zinc, or it may be an insoluble suspension of acylated tyrosine, or acylated sugars, cationically or anionically derivatized polysaccharides, or polyphosphazenes.

In general, an immune response is generated to an antigen through the interaction of the antigen with the cells of the immune system. Immune responses may be broadly categorized into two categories: humoral and cell-mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an antigenic unit). Immune responses can be measured in many ways including activation, proliferation, or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, immunostimulatory compositions can promote a Th1-type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF, and low levels of TNF-α. Th1 type cytokines promote both cell-mediated immunity and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in some embodiments, the present disclosure provides a method of stimulating a Th1-type immune response in a subject comprising administering to a subject a composition comprising an antigenic unit (e.g., NS1 peptide or polypeptide). However, in other embodiments, the present invention provides a method of stimulating a Th2-type immune response in a subject (e.g., if balancing of a T cell mediated response is desired) comprising administering to a subject a composition comprising an antigenic unit (e.g., NS1 peptide or polypeptide). In further embodiments, adjuvants are used to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present disclsoure. These include, but are not limited to, the following. In some embodiments, monophosphoryl lipid A (e.g., in particular, 3-de-O-acylated monophosphoryl lipid A (3D-MPL)), is used. 3D-MPL is an adjuvant manufactured by Ribi Immunochem, Montana. It is often supplied as a mixture of 3-de-O-acylated monophosphoryl lipid A with either 4, 5, or 6 acylated chains. In some embodiments, diphosphoryl lipid A and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 micrometers in diameter, described in EP 0 689 454, hereby incorporated by reference in its entirety).

In some embodiments, saponins are used as an immunogen (e.g., Th1-type adjuvant). Saponins are adjuvants (See, e.g., Lacaille-Dubois and Wagner (1996) Phytomedicine vol 2 pp 363-386). Examples of saponins include Quil A (derived from the bark of the South American tree Quillaja Saponaria Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety).

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activates various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. AcadSci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63), LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., WO93/13202 and WO92/19265, each of which is hereby incorporated by reference), and other immunogenic substances (e.g., that enhance the effectiveness of a composition of the present invention) are used with a vaccine composition of the present disclosure.

Additional examples of adjuvants include, but are not limited to, poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); 0M-174 (a glucosamine disaccharide related to lipid A; O M Pharma S A, Meyrin, Switzerland); and Leishmania elongation factor (a purified Leishmania protein; Corixa Corporation, Seattle, Wash.).

Adjuvants may be added to a vaccine composition or the adjuvant may be formulated with carriers, for example liposomes or metallic salts (e.g., aluminium salts (e.g., aluminium hydroxide)) prior to combining with or co-administration with a composition.

In some embodiments, a composition comprising NS1 peptides or polypeptides comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a vaccine composition comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives is contemplated to be useful in the present invention including, but not limited to, cross-linked derivatives of poly (acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive enhances induction of an immune response in a subject due to an increase in duration and/or amount of exposure to an antigenic unit that a subject experiences when a mucoadhesive is used compared to the duration and/or amount of exposure to a vaccine molecule in the absence of using the mucoadhesive.

In some embodiments, compositions comprise sterile aqueous preparations. Acceptable vehicles and solvents include, but are not limited to, water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

In some embodiments, compositions are used therapeutically (e.g., to enhance an immune response) or as a prophylactic (e.g., for immunization (e.g., to prevent signs or symptoms of disease)). A composition can be administered to a subject via a number of different delivery routes and methods.

For example, in some embodiments, compositions are administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal, and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the route of administration as it has been shown that mucosal administration of antigens induces protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). In addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, compositions are used to protect or treat a subject susceptible to, or suffering from, disease by administering via a mucosal route (e.g., an oral/alimentary or nasal route). Alternative mucosal routes include intravaginal and intra-rectal routes. In some embodiments, a nasal route of administration is used, termed "intranasal administration" or "intranasal vaccination" herein. Methods of intranasal vaccination include the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this invention.

Compositions can also be administered via the oral route. Under these circumstances, a vaccine composition comprises a pharmaceutically acceptable excipient and/or include alkaline buffers or enteric capsules. Formulations for nasal delivery may include those with dextran or cyclodextran and saponin as an adjuvant.

Compositions can also be administered via a vaginal route. In such cases, a composition may comprise pharmaceutically acceptable excipients and/or emulsifiers, polymers (e.g., CARBOPOL), and other known stabilizers of vaginal creams and suppositories. In some embodiments, vaccine compositions are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition is administered to a mucosal surface of a subject in either a priming or boosting vaccination regime. Alternatively, in some embodiments, the composition is administered systemically in either a priming or boosting vaccination regime. In some embodiments, a composition is administered to a subject in a priming vaccination regimen via mucosal administration and a boosting regimen via systemic administration. In some embodiments, a composition is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal, or intravenous administration.

In some embodiments, compositions are administered by pulmonary delivery. For example, a composition of the present disclosure can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this disclosure are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers, and/or other agents useful in therapy. Also, the use of liposomes, microcapsules or microspheres, inclusion complexes, or other types of carriers is contemplated.

Thus, in some embodiments, a composition is used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance a immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present disclosure. Indeed, a wide variety of subjects are contemplated to be benefited from administration of a composition of the present disclosure. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

The present disclosure also provides methods involving co-administration of a vaccine composition with one or more additional active and/or immunostimulatory agents (e.g., a composition comprising a different antigenic unit, an antiviral agent, anti-oxidant, etc.). In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antiviral agents, adjuvants, etc.) can be any of the well-known agents in the art, including, but not limited to, those that are currently in clinical use.

In some embodiments, a composition is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an antigenic unit or organism from which the antigenic unit is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of the composition) may have a stronger immune response to an antigenic unit than a subject administered a composition via just one route.

Other delivery systems include time-release, delayed release, or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a composition of the present disclosure is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of a material present in the concentrated composition. Concentrated compositions are contemplated to be useful in a setting in which large numbers of subjects may be administered a composition of the present invention (e.g., an immunization clinic, hospital, school, etc.). In some embodiments, a composition (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an antigenic unit in a boost dose enables vigorous systemic immunity in a subject. The boost can be with the same formulation given for the primary immune response, or can be with a different formulation that contains the antigenic unit. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Thus, it is not intended that the present invention be limited to any particular subject and/or application setting.

The present disclosure further provides kits comprising the compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

II. Antiviral Agents

Embodiments of the present invention provide antiviral agents against flaviviruses, methods of identifying such agents, and therapeutic uses thereof. NS1 forms stable homodimers approximately 30 minutes after synthesis and the dimers have affinity for membranes, even in the absence of transmembrane domains. NS1 has an important role in early RNA replication and thus in virus production. Interaction of NS1 and NS4A/NS4B is required for replication of the viral genome. It had previously been thought that the NS1 dimer has a hydrophobic surface for peripheral membrane association. From the 3D structure it is now clear that a β-roll domain (amino acids 1-29) is responsible for dimer formation and creates a large hydrophobic surface upon dimerization, presumably the membrane interaction region.

Amino acids Arg10 and Gln11 (WNV NS1), which have been shown to be involved in the NS4B interaction, are present in the β-roll domain, indicating that disruption of the β-roll provides a target region for antiviral agents. In the 3D structure, another region of NS1 (amino acids 159-162) forms part of the hydrophobic surface adjacent to the β-roll domain. Disruption of this region by mutagenesis is highly deleterious to viral RNA replication. Accordingly, in some embodiments, therapeutic agents target the NS1 dimerization domain and/or binding regions for the replication complex are identified.

In some embodiments, target therapeutics (e.g., libraries of compounds) are screened using the NS1—liposome binding and disruption assay described below or other assay. In some embodiments, screening is high throughput screening.

In some embodiments, the present disclosure provides therapeutic agents that target NS1. In some embodiments, agents (e.g., small molecules, antibodies, nucleic acids, aptamers, etc.) are identified using the screening methods described herein.

In some embodiments, the present disclosure provides agents (e.g., antibodies or aptamers) that interact with amino acids 159-162 and inhibit one or more biological activities of NS1. In some embodiments, such antibodies or aptamters find use in the treatment or prevention of infection by flaviviruses.

In some embodiments, the peptides described herein or full length NS1, including fragments, derivatives and analogs thereof, may be used as immunogens to produce antibodies having use in the diagnostic, screening, research, and therapeutic methods described herein. The antibodies may be polyclonal or monoclonal, chimeric, humanized, single chain, Fv or Fab fragments. Various procedures can be used for the production and labeling of such antibodies and fragments. See+, e.g., Burns, ed., Immunochemical Protocols, 3rd ed., Humana Press (2005); Harlow and Lane, Antibodies: A Laboratory Manual, Cold Spring Harbor Laboratory (1988); Kozbor et al., Immunology Today 4: 72 (1983); Köhler and Milstein, Nature 256: 495 (1975).

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

A composition of the present disclosure may be formulated for administration by any route, such as mucosal, oral, transdermal, intranasal, parenteral or other route described herein. The compositions may be in any one or more different forms including, but not limited to, tablets, capsules, powders, granules, lozenges, foams, creams or liquid preparations.

In some embodiments, compositions (e.g., compositions for inducing an immune response or anti-viral agents) are co-administered with one or more antiviral agents. For example, one or more antiviral agents may be administered with, before and/or after administration of the pharmaceutical composition or vaccine composition described herein. Numerous antimicrobial agents are currently available for use in treating bacterial, fungal, and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include, for example, agents that act directly to disrupt the cell membrane of the microorganism (e.g., detergents such as polmyxin and colistimethate and the antifungals nystatin and amphotericin B); agents that alter protein synthesis and lead to cell death (e.g., aminoglycosides); and the nucleic acid analogues such as zidovudine, gangcyclovir, vidarabine, and acyclovir which act to inhibit viral enzymes essential for DNA synthesis. Various combinations of antimicrobials may be employed.

III. Diagnostic Uses

Embodiments of the present disclosure provide diagnostic and research uses. NS1 is synthesized by all flaviviruses and is secreted from infected mammalian cells. Embodiments of the present disclosure provide a simplified method of diagnosis during the acute stage of dengue infection is via detection of viral antigen NS1 in the bloodstream. The presence of secreted NS1 (sNS1) in the bloodstream stimulates a strong humoral response and high concentrations of this antigen can be detected in patients with primary and secondary dengue infections up to 9 days after the onset of illness. Many studies have investigated the utility of sNS1 detection as a diagnostic tool during the acute phase of a dengue infection. A serotype specific mAb-based NS1 antigen-capture ELISA has been developed and shows good serotype specificity. This test can differentiate between primary and secondary dengue virus infections. Sensitivity and specificity of NS1 antigen detection methods range from 49 to 59% for the Bio-Rad NS1 antigen strip (Bio-Rad, France), and 93 to 99% for the Panbio dengue NS1 antigen strip (Inverness, Australia). Another leading NS1 antibody on the market is directed against a synthetic peptide corresponding to a region within amino acids 51-144 of NS1 (dengue virus 2).

None of these materials was developed with knowledge of the NS1 3D structure. Using the 3D structures and a multiple-sequence alignment, a nonconserved wing domain that is highly exposed in the sNS1 hexamer was identified. The wing includes a highly accessible disordered loop with a short conserved peptide corresponding to amino acids 114-119. Using the 3D structures, regions of variability among NS1 proteins of the four dengue virus serotypes was identified. In some embodiments, antibodies to these peptides (e.g., monoclonal or polyclonal antibodies) find use in diagnostic and research uses for identifying flaviviruses and as serotype-specific dengue diagnostics. In some embodiments, antibodies directed to surface loops that are conserved among the dengue serotypes find use as pan-dengue diagnostics.

In some embodiments, diagnostic assays utilize antibodies that specifically bind to regions of NS1 (e.g., amino acids 114-119 or other regions). Methods for generating antibodies are described above.

In some embodiments, an immunoassay is utilized to detect binding of antibodies to NS1 (e.g., to diagnose infection by flavivirus). Illustrative non-limiting examples of immunoassays include, but are not limited to: immunoprecipitation; Western blot; ELISA; immunohistochemistry; immunocytochemistry; immunochromatography; flow cytometry; and, immuno-PCR. Polyclonal or monoclonal antibodies detectably labeled using various techniques (e.g., colorimetric, fluorescent, chemiluminescent or radioactive labels) are suitable for use in the immunoassays.

Immunoprecipitation is the technique of precipitating an antigen out of solution using an antibody specific to that antigen. The process can be used to identify proteins or protein complexes present in cell extracts by targeting a specific protein or a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and optionally sorting microscopic particles or cells suspended in a stream of fluid. It allows simultaneous multi-parametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In other embodiments, the immunoassay described in U.S. Pat. Nos. 5,599,677 and 5,672,480; each of which is herein incorporated by reference.

IV. Research Uses

In some embodiments, the present invention provides research and screening uses (e.g. to identify therapeutic agents that target NS1). NS1 contains a hydrophobic protrusion and membrane-binding region that interacts with the early replication complex. Experiments conducted during the course of development of embodiments of the present invention determined that NS1 binds liposomes and converts them into protein-lipid nanoparticles. Disruption of the NS1-membrane interaction can cripple viral genome replication. In some embodiments, the liposome-based assay for NS1-membrane interaction is used as an assay to identify antiviral leads.

Accordingly, in some embodiments, the present invention provides methods and compositions for identifying agents that interact with NS1 and alter one or more biological activities of NS1. In some embodiments, the assays comprise contacting a purified flavivirus NS1 polypeptide with a liposome and a test compound; and measuring the level of binding of the NS1 polypeptide to the liposome in the presence and absence of the test compound. In some embodiments, test compounds that interact with NS1 are screened in additional assays to identify test compounds that alter (e.g., inhibit or decrease) one or more biological activities of NS1 and consequently treat or prevent infection by flaviviruses.

EXPERIMENTAL

The following examples are provided in order to demonstrate and further illustrate certain preferred embodiments and aspects of the present disclosure and are not to be construed as limiting the scope thereof.

Example 1

Materials and Methods

Construction, cloning and expression evaluation. The construction of the West Nile virus (WNV; NY99) and dengue virus type 2 (DEN2; 16681) NS1 coding sequences, production of recombinant baculovirus and small-scale expression evaluation were carried out as previously described (Brown et al., *Protein Expr Purif* 77, 34-45 (2011)).

Lysis buffer screening. High-five and Sf9 cells at a density of $2 \times 10^6$ cells per mL were infected with baculovirus encoding the NS1 sequence fused with a secretion signal sequence (Ac-gp64 for WNV NS1, Op-gp64 for DEN2 NS1), followed by a His tag (Brown et al., supra). After 72 hours, cells were pipetted into a 24-well block. Cell pellets were resuspended and then sonicated 5 sec. The contents of each well were transferred to 1.7 mL microfuge tubes and centrifuged 10 min at 20,000×g. The small-scale, high-throughput purification was then completed as previously described (Brown et al., supra).

Large-scale production and purification of NS1 protein. Cell pellets (High Five for WNV NS1, Sf9 for DEN2 NS1) from 1 L NS1 infection cultures were resuspended at 4 mL/g with 50 mM Tris (pH8.5), 50 mM $(NH_4)_2SO_4$, 10% glycerol, 0.5% triton, and sonicated on ice 3×30 sec at 50% power. The lysate was cleared by centrifugation and the supernatant was diluted by 50% with buffer. Protein was batch bound to nickel resin for four hours. The slurry was poured into a column and the flow-through buffer was collected. The resin was washed with 50 volumes of buffer, and the protein was eluted in 10-15 volumes of buffer with 200 mM imidazole. Detergent was absent from the buffers in subsequent steps. The eluate was dialyzed, concentrated and subjected to gel filtration using a Superose S200 column. An alternative purification was carried out in which the wash and elution buffers for the metal-affinity chromatography step did not contain triton and the dialysis step was omitted.

Crystallization. All crystals were grown by vapor diffusion at 4° C. WNV NS1 crystal form 1 grew by equilibrating ~7 mg/mL protein against a reservoir solution containing 20%-25% PEG 3000 or PEG 3350, 5% glycerol, and 150-300 mM sodium citrate pH 5.5. Crystals formed in two weeks, but often were allowed to continue growing for up to six months before harvesting and data collection. Crystal form 2 grew in similar conditions, but over a pH range of 5.5-7.5. The data reported here were collected from a form 2 crystal grown with 25% PEG 3350, 250 mM sodium citrate pH 5.5. DEN2 NS1 crystals grew by equilibrating ~10 mg/mL protein against a reservoir solution containing 21% PEG 3350 and 250 mM ammonium formate pH 6.6. Crystals were harvested without additional cryoprotection and cryoprotected in liquid nitrogen.

Structure determination. The WNV NS1 structure in crystal form 1 was solved by native sulfur SAD phasing. Data were collected at GM/CA beamline 23-ID-D at the Advanced Photon Source. Data were collected at 7.1 keV using a 100-mm helium box to reduce air absorption. 90° of data were collected from each crystal using 0.5° oscillations in inverse beam mode. Data (up to ~2.9 Å maximum usable resolution) were integrated and scaled using XDS (Kabsch, *Acta Crystallogr D Biol Crystallogr* 66, 125-132 (2010)) (Table 1). Complete data sets from eighteen crystals were scaled and combined using XSCALE for a final data multiplicity of 200 (anomalous multiplicity of 100 between 50.0 and 3.1 Å). Anomalous signal was estimated to extend to 6.1 Å. Data to 5.2 Å were used to find sulfur sites with SHELX (Sheldrick, *Acta Crystallogr D Biol Crystallogr* 66, 479-485 (2010)). Sites for what were later determined to be all 12 cysteine disulfides and 8 of 10 methionines were located. Two-fold noncrystallographic symmetry (NCS) was identified by visual inspection of the sites, and the NCS operator was refined using LSQKAB (Programs for Protein Crystallography. *Acta Cryst. D,* 760-763 (1994). Phases to 4.5 Å were calculated using SHELX, and these phases were extended and modified by DM (Programs for Protein Crystallography. *Acta Cryst. D,* 760-763 (1994) to 3.0 Å using the two-fold NCS operator and solvent flattening (75% solvent content). The resultant maps were readily interpretable (FIG. 7a), and a preliminary model was auto-built using Buccaneer (Cowtan, *Acta Crystallogr D Biol Crystallogr* 62, 1002-1011 (2006)). Disulfide and methionine sites were confirmed by inspection of the anomalous difference map, which in conjunction with the high occurrence of tryptophan, allowed us to build the chain trace and determine the correct register with a high degree of confidence. Model building was carried out using Coot (Emsley et al., *Acta Crystallogr D Biol Crystallogr* 60, 2126-2132 (2004) and refinement with Refmac (Murshudov et al., *Acta Crystallogr D Biol Crystallogr* 53, 240-255 (1997)) and Phenix (Adams et al., *Acta Crystallogr D Biol Crystallogr* 58, 1948-1954 (2002)) using jelly body restraints and Prosmart-generated secondary structure restraints. Native data to 2.6 Å were collected at 12 keV from a crystal grown using vapor diffusion under Al's oil (Hampton Research) (Table 1). The final models are complete with the exception of residues 108-128 (chain A) and 109-129 (chain B) and contain 5 of 6 identified glycosylation sites and several residues from N-terminal His$_6$ tag and linker (11 in chain A and 21 in chain B). Coordinates and structure factors for the 2.6-Å native structure are deposited in the protein data bank. The WNV NS1 dimer structure was used to solve structures of WNV NS1 in crystal form 2 and DEN2 NS1 by molecular replacement using MOLREP (Programs for Protein Crystallography. *Acta Cryst. D,* 760-763 (1994). Both of these crystal forms are twinned. The structures were validated by Mol-Probity (Chen et al., *Acta Crystallogr D Biol Crystallogr* 66, 12-21 (2010)). The dimer interface buries 2700 Å$^2$ of surface area per monomer, as analyzed by PISA (Krissinel et al., *J Mol Biol* 372, 774-797 (2007)). The β-roll accounts for 70% of the buried surface area.

Liposome preparation and NS1 interaction. Lipid solutions were made by dissolving cholesterol (CHOL) (Sigma) and 1, 2-dipalmitoyl-sn-glycero-3-phosphocholine (PC) in chloroform at ratios of 10:90 CHOL:PC. Portions of each solution were placed in glass tubes and dried under a stream of nitrogen. Liposomes were produced by adding 400 μL of buffer (50 mM Bis-Tris pH 5.5, 50 mM (NH$_4$)$_2$SO$_4$, 10% glycerol) to the dried lipids and then sonicating in a bath at 37° C. for approximately 5 min. A 50 μL sample of approximately 10 mg/mL NS1 protein was mixed with 150 μL of the liposome solution in 1.5 mL tubes followed by 2 hr incubation at 37° C. and 30 min centrifugation at 13,000 RPM. The supernatant was removed and the soluble fraction and pellet were treated separately for electron microscopy. The methyltransferase MycE (Akey et al., *J Mol Biol* 413, 438-450 (2011)), which does not interact with membranes, was used as a negative control. NS1 interaction with liposomes was insensitive to pH over a range of 5.5-7.5.

Negative-stain electron microscopy. Samples were prepared using the conventional negative staining protocol (Ohi et al., *Biol Proced Online* 6, 23-34 (2004)), and imaged at room temperature with a Morgagni 268 at 100 kV or a Tecnai T12 electron microscope (FEI Company) operated at 120 kV. For single particle analysis, images were recorded with the T12 at a magnification of 71,139× and a defocus value of ~1.6 μm on a Gatan US4000 CCD camera. All images were binned (2×2 pixels) to obtain a pixel size of 4.16 Å at the specimen level. A total of 7297 projections of TEV-cleaved NS1 were manually excised using Boxer [part of the EMAN 1.9 software suite]. (Ludtke et al., *J Struct Biol* 128, 82-97 (1999)) Reference-free alignment and classifications into 100 classes for each sample were performed in EMAN 1.9 using refine2d.py (Ludtke et al., supra; Ohi et al., supra).

Figure 10:
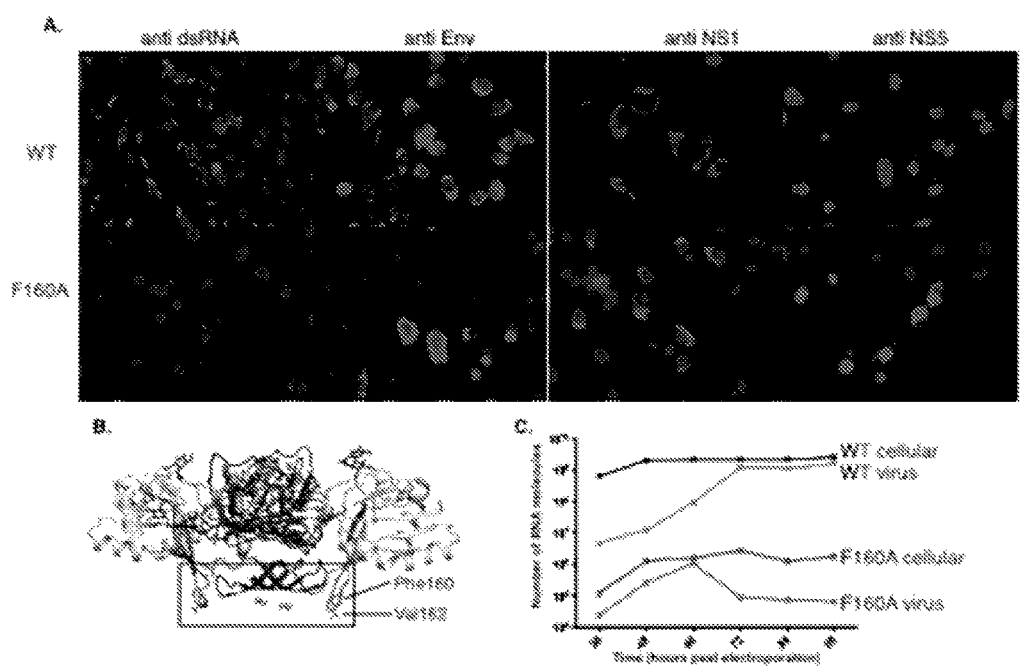
FIG. 10 shows NS1 mutagenesis. (A) Localization of dsRNA, E, NS1 and NS5 by immunofluorescence (IF) assay. (B) Molecular drawing (same view as FIG. 2C) shows the position of Phe160 and Val162 in the "greasy finger" of the connector sub-domain. (C) Total viral RNA in both virus particles and infected cells is reduced in F160 Å mutants. (D) Effect of amino acid substitutions on NS1 association with liposomes.
Figure 10:
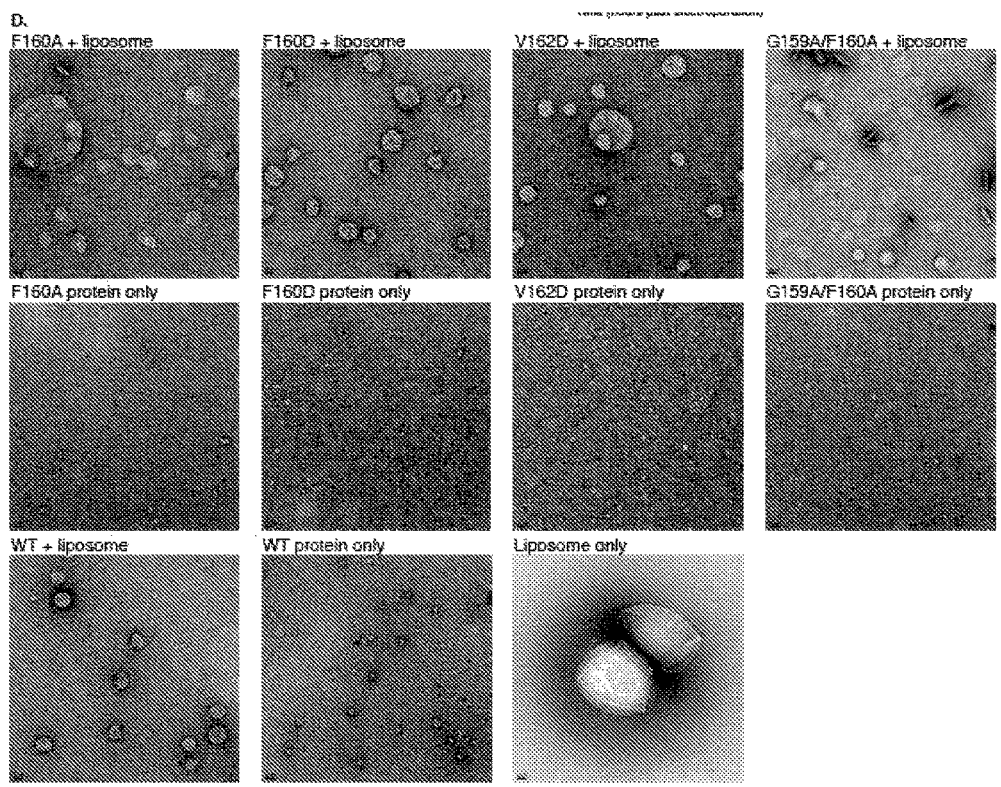

Mutagenesis in DEN2. NS1 mutations were introduced into the DENV-2 16681 infectious cDNA clone (pD2/IC-30P) (Kinney et al., *Virology* 230, 300-308 (1997)) by standard overlapping PCR and ligated into the SphI and KasI restriction sites of pD2/IC-30P. Constructs were then digested with XbaI and in vitro transcribed using T7 RNA polymerase. Transcripts (10 μg) for wild type DEN2 and each of the four full-length clones containing mutations were electroporated into 1×10$^7$ BHK-15 cells. Supernatants collected 96-hr post-electroporation were used for plaque assays with neutral red staining after 7 days (Table 2). Plaques were visible only for the wild type (3-mm diameter) and the F160 Å mutant (1-mm diameter). An immunofocus virus titer assay using supernatants 96-hr post-electroporation was consistent with the plaque assay (Table 2). In a separate experiment (FIG. 10), BHK-15 cells were fixed 48 hr post electroporation using 3.7% paraformaldehyde and permeabilized using 0.1% Triton X-100 for immunofluorescence analysis with mouse monoclonal antibodies to double-stranded RNA, DEN2 envelope protein, DEN2 NS1 and DEN2 NS5 (RNA-dependent RNA polymerase). The secondary antibody was tetramethylrhodamine (TRITC)-conjugated goat anti-mouse and the nuclei were stained with Hoechst stain.

Results

Flaviviruses have a positive-sense RNA genome that encodes a single viral polyprotein. The polyprotein is inserted into the ER membrane through several signal sequences and processed by viral and host proteases into three structural and seven non-structural proteins (NS1, NS2A, NS2B, NS3, NS4A, NS4B, NS5) (Lindenbach, C. M. Rice, Molecular biology of flaviviruses. *Adv Virus Res* 59, 23-61 (2003)). Six of the non-structural proteins (NS2A-NS5) form a replication complex on the cytoplasmic side of the ER membrane where the NS3 and NS5 enzymes function at a scaffold created by the other four trans-membrane proteins. The remaining protein, the conserved glycosylated non-structural protein 1 (NS1), is associated with lipids, both early in infection, where intracellular dimeric NS1 localizes on the ER membrane at the site of viral RNA replication, and late in infection, where secreted hexameric NS1 lipo-protein particles interact with components of the complement-mediated immune system (Suthar et al., *Nat Rev Microbiol* 11, 115-128 (2013); Muller et al., *Antiviral Res* 98, 192-208 (2013)). NS1 is an essential cofactor for replication of the flavivirus genome (Khromykh et al., *J Virol* 74, 3253-3263 (2000); Lindenbach et al., *J Virol* 73, 4611-4621 (1999); Westaway et al., *J Virol* 71, 6650-6661 (1997); Lindenbach et al., *J Virol* 71, 9608-9617 (1997); Mackenzie et al., *Virology* 220, 232-240 (1996)). Elimination of NS1 abrogates viral RNA replication and replacement of NS1 with cross-species NS1 impairs RNA synthesis, which can be rescued by mutations in NS4A, indicating a genetic interaction between NS1 and NS4 Å (Lindenbach et al., supra). Additionally, genetic and biochemical data indicate a direct interaction between NS1 and NS4B (Youn et al., *J Virol* 86, 7360-7371 (2012)). As NS1 localizes to the luminal face of the ER membrane, it is postulated to organize other factors of the replication complex through the trans-membrane proteins NS4 Å and NS4B (Muller et al., supra). Electron microscopy (EM) studies of secreted NS1 (sNS1) identified a symmetric barrel-shaped hexamer which carries a cargo of ~70 lipid molecules (Gutsche et al., *Proc Natl Acad Sci USA* 108, 8003-8008 (2011); Muller et al., *J Gen Virol* 93, 771-779 (2012)). NS1 interacts with multiple components of both the innate and adaptive immune systems, (Avirutnan et al., *J Immunol* 187, 424-433 (2011); Avirutnan et al., *J Exp Med* 207, 793-806 (2010); Chung et al., *Proc Natl Acad Sci US A* 103, 19111-19116 (2006)) is involved in immune system evasion and pathogenesis, (Avirutnan et al., 2011, supra; Avirutnan et al., 2010, supra; Chung et al., supra; Krishna et al., *J Virol* 83, 4766-4777 (2009)) and is the major antigenic marker of viral infection (Young et al., *J Clin Microbiol* 38, 1053-1057 (2000)). Although many antibodies to NS1 offer some protection, a number of antibodies are implicated in disease pathogenesis (Falconar, *Clin Vaccine Immunol* 15, 549-561 (2008); Falconar, *Arch Virol* 142, 897-916 (1997); Henchal et al., *J Gen Virol* 69 (Pt 8), 2101-2107 (1988)). While the role of NS1 in multiple stages of the virus life cycle is well established, little is known of the molecular mechanisms of its various functions. The lack of sequence identity to any protein of known structure and the difficulty of producing pure, stable protein has hindered progress in understanding the roles and mechanisms of NS1. An understanding of NS1 structure will help to sort out these contradictory results and will facilitate more efficient vaccine development.

Figure 7:
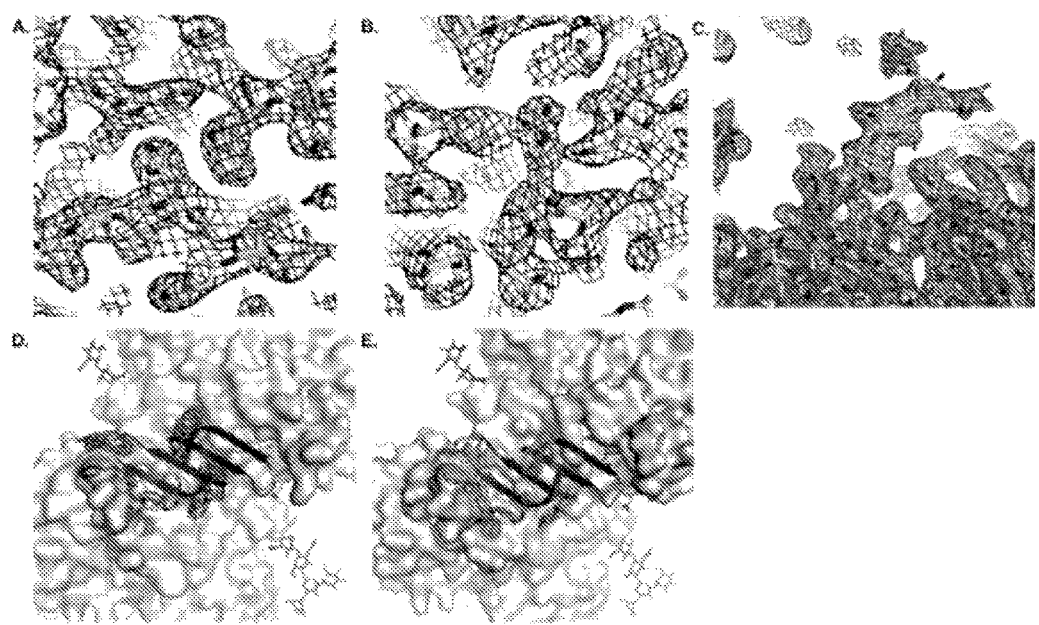
FIG. 7 shows electron densities from WNV NS1 crystal form 1. (A,B) Two regions of density in the 3.0-Å map (1σ contour) computed with phases from S-SAD followed by density modification phase refinement and extension from 4.5 Å to 3.0 Å. (C) Density for the carbohydrate at Asn207 in the final 2.6-Å map (2mFo-dFc, 1σ contour). (D) Density in the original 3.0-Å map shown in A (1σ contour) for detergent fragments (Triton X-100 head groups and tail) bound to the hydrophobic protrusion. The final model is superimposed. (E) Omit density (Fo-Fc, 3σ contour) for bound detergent fragments in the final 2.6-Å map.

Recombinant, full-length, glycosylated WNV and dengue virus type 2 (DEN2) NS1 was produced in insect cells using a baculovirus expression system. Despite the presence of a secretion signal in the expression construct, nearly all NS1 was retained inside the cell and partitioned with the membrane fraction. Soluble NS1 was released by mild detergent treatment of the membrane fraction and, after a two-step purification, appeared as a dimer by gel filtration chromatography and in agreement with direct visualization of particles by negative-stain electron microscopy (EM) (FIG. 7A, B). Multiple chromatography steps without detergent shifted the oligomeric state to a hexamer, presumably due to removal of bound detergent (FIG. 7C, D). WNV NS1 crystallized in two forms and DEN2 NS1 in one form. The WNV NS1 structure was solved from the anomalous scattering of the native sulfur atoms (12 Cys and 5 Met per subunit) using high-multiplicity (~100 fold) data acquired from 18 crystals of form 1 (Table 1). A readily interpretable 3.0 Å electron density map was obtained by phase extension from 4.5 Å with twofold averaging of monomer densities (FIG. 7A, B). The twelve cysteines form six disulfide bonds within the NS1 monomer. Three asparagines are glycosylated (Asn130, Asn175 and Asn207), each with clear electron density for one to five sugar residues (FIG. 7C). The structure is complete for all amino acids with the exception of one internal loop (amino acids 108-128). This structure was used to solve structures of WNV NS1 in crystal form 2 and DEN2 NS1, both of which were obtained from twinned crystals. Identical dimer structures occur in WNV and DEN2 NS1 (0.582 Å root-mean-square deviation of 576 Cα atoms).

Figure 2:
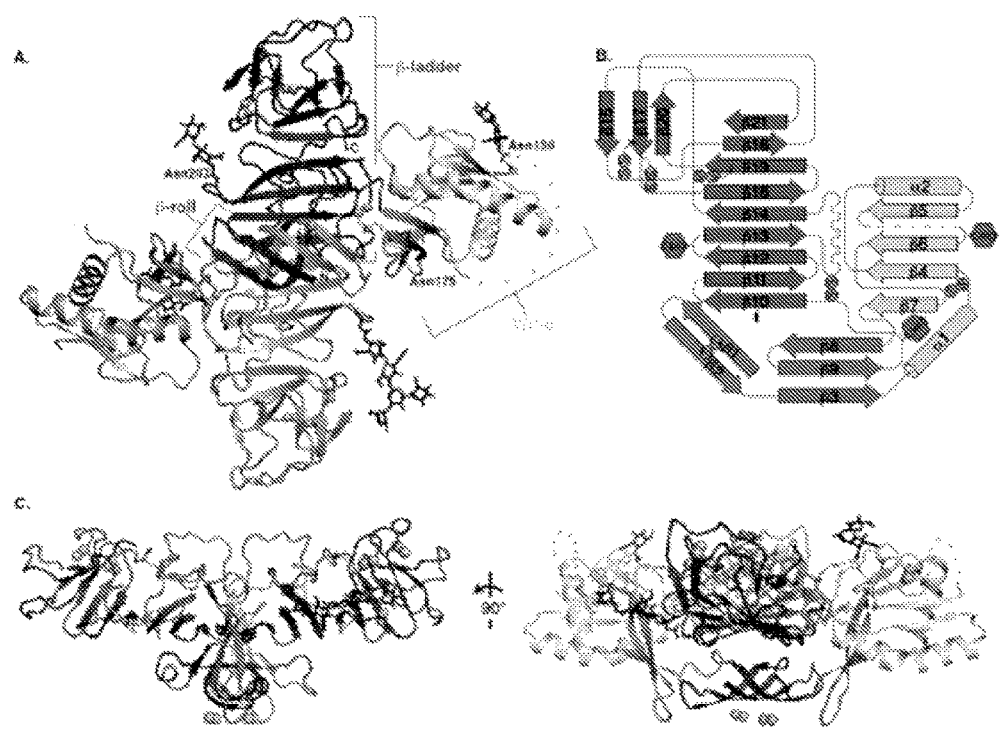
FIG. 2 shows the structure of the NS1 dimer. (A) NS1 dimer. Disulfides are shown as spheres and N-linked glycosylation sites as sticks with black C. A 20-residue disordered region is indicated with dotted lines. (B) Topology diagram for NS1 monomer. (C) Perpendicular views of NS1 from the edge (left) and the end (right) of the β-ladder.

NS1 has an inherently dimeric structure constructed around an extended central β-sheet domain of novel fold (FIG. 2A, B; 11). Each monomer has three distinct domains described here from N- to C-terminus. A small "β-roll" domain comprising amino acids 1-29 contributes extensively to dimer formation (FIG. 2A; FIG. 7D, E). The β-roll is a mini domain-swap structure of two β-hairpins (β1, β2), one from each monomer, each stabilized by a disulfide (Cys4-CyslS). The β-hairpins extend across the dimer axis and intertwine to form a four-stranded β-sheet that curves into a roll-like structure.

The second domain (amino acids 30-180) of each monomer protrudes from the central β-domain like a wing (FIG. 2a). Each "wing" domain contains two glycosylation sites (Asn130, Asn175), an internal disulfide (Cys55-Cys143), and two discreet subdomains. An α/β subdomain (amino acids 38-151) comprises a four-stranded β-sheet (β4-β7), two α-helices (α1, α2) and a disordered distal tip (amino acids 108-128; FIG. 2a, dotted line). A connector subdomain (amino acids 30-37 and 152-180), consisting of a three-stranded β-sheet (β3, β38, β9), links the wing to the β-roll and central β-sheet and packs against the β-roll (FIG. 2a). A disulfide (Cys179-Cys223) also links the wing to the central β-sheet domain.

The predominant structural feature of NS1 is a continuous β-sheet that extends along the length of the dimer with its 18 β-strands arranged like the rungs of a ladder (FIG. 2A). This core "β-ladder" domain is formed by the C-terminal half of NS1 (amino acids 181-352), in an arrangement where each monomer contributes nine rungs to the anti-parallel β-ladder. In a simple (+1) topology, the first five β-strand rungs of each monomer begin at the dimer interface and proceed sequentially towards the end of the ladder (β10-β14, FIG. 1b). Asn207 in the β12-β13 loop is glycosylated (FIG. 7D). Most of the inter-strand loops are short with the notable exception of a "spaghetti loop" between β3 and β4, with remarkable length (54 amino acids, 219-272), lack of secondary structure and excellent order (57 hydrogen bonds) (FIG. 2C). A highly conserved tip region (FIGS. 8 and 11) at each end of the β-ladder domain (amino acids 278-352) contains four strands of the central β-ladder (β18, β19, β16, β21), a small three-stranded β-sheet (β15, β17, β20), and three cystine disulfides (280-329, 291-312, 313-316).

The overall dimensions of the NS1 dimer are 90 Å along the length of the β-ladder and 90 Å in width from wingtip to wingtip (FIG. 2A). The β-ladder defines a plane through the NS1 dimer (FIG. 2C). The β-roll domain resides on one side of this plane. On the other side of the plane, in a different neighborhood, are the spaghetti loop, the glycosylation sites, the wing domain disordered loop, and the C-terminus, which, prior to proteolytic cleavage, is fused to the >20-residue lumen-side N-terminus of viral protein NS2A. The NS1 dimer is 40 Å thick in this third direction from β-roll to spaghetti loop.

Figure 3:
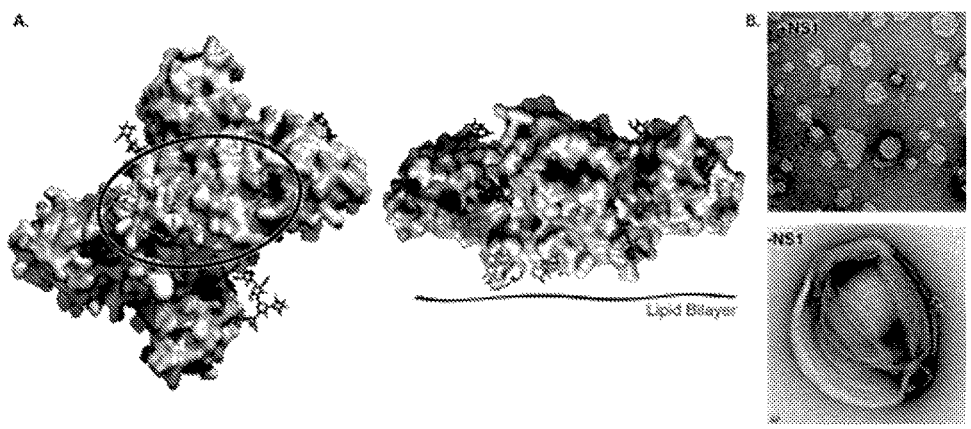
FIG. 3 shows the hydrophobic protrusion for membrane interaction. (A) NS1 electrostatic surface potential at pH 6.5 colored from electropositive (+5 kT) to electronegative (−5 kT) with bound detergent and glycosylation sites, viewed on the left as in FIG. 2A with the β-roll circled and facing the reader, and on the right as in FIG. 2c (right panel). (B) Effect of WNV NS1 on liposome structure.
Figure 4:
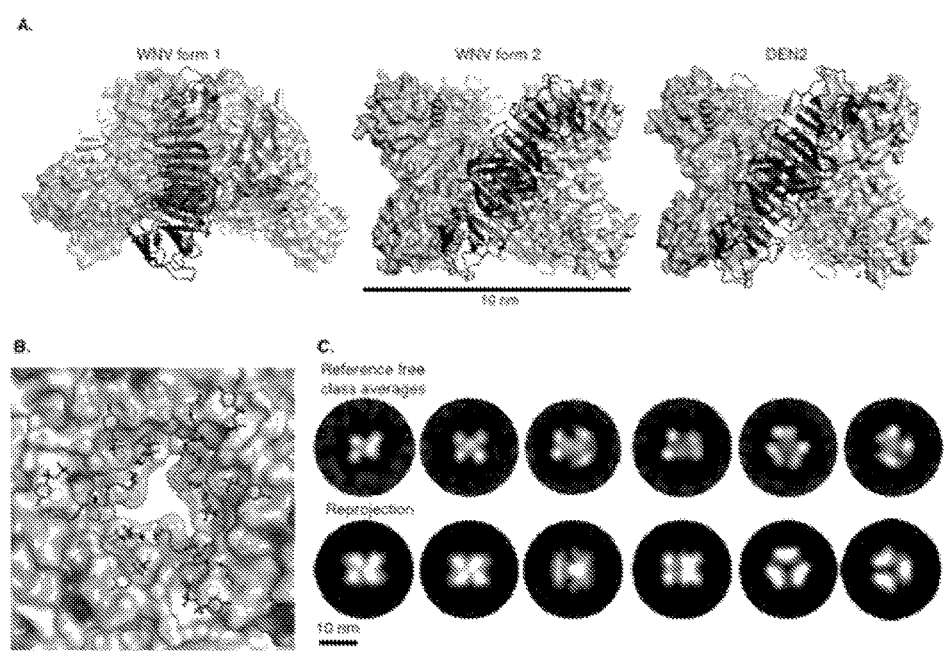
FIG. 4 shows NS1 hexamer association. (A) NS1 hexamers: the splayed hexamer in WNV NS1 crystal form 1 (left) and the symmetric hexamers in WNV NS1 form 2 (center) and in DEN2 crystals (right). (B) Association of hydrophobic protrusions at the center of the WNV NS1 hexamer in crystal form 1: The electrostatic surface potential illustrates the hydrophobicity of the surfaces. (C) Comparison of WNV NS1 hexamers in solution with the symmetric NS1 hexamer in crystals.
Figure 5:
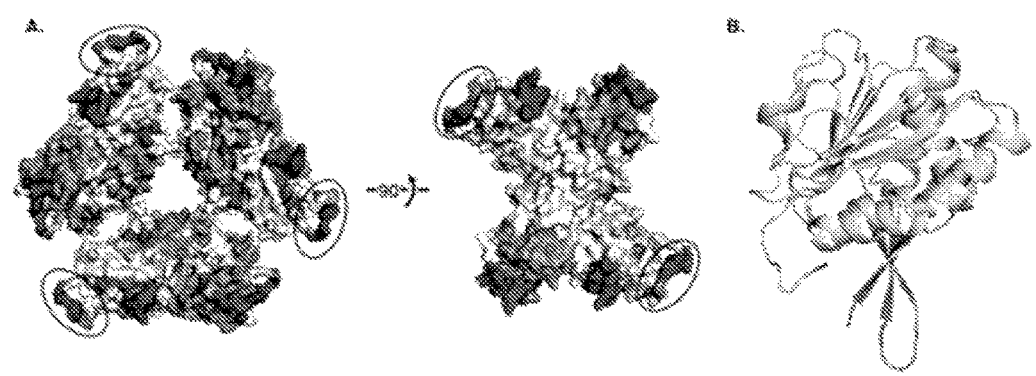
FIG. 5 shows NS1 and the immune system (A) Linear epitopes to NS1 mapped on the structure. (B) Similarity of the NS1 wing α/β subdomain to the RIG-I family of innate immune proteins.
Figure 6:
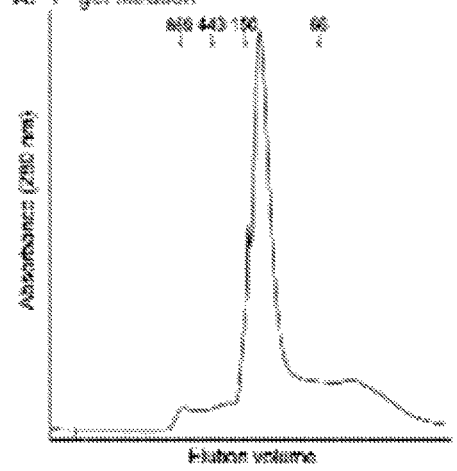
FIG. 6 shows preparation of recombinant NS1. (A) Gel filtration of DEN2 NS1 following Ni-affinity purification in the presence of detergent and cleavage of the $His_6$ tag. (B) Negative-stain EM image of the peak fraction from the elution in A. Scale bar in the lower left is 20 nm. (C) Second detergent-free gel filtration of DEN2 NS1. Fractions from the major peak in A were pooled and eluted from a second analytical-scale S200 gel filtration column. (D) Negative-stain EM image of the peak fraction from the elution in C, showing larger particles than in seen in B. Scale bar in the lower left of B and C is 20 nm.
Figure 6:
Figure 6:
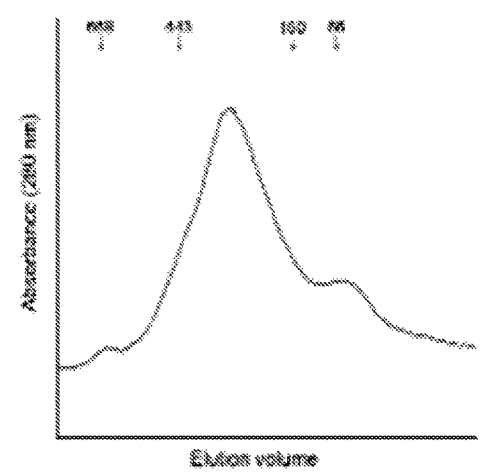
Figure 6:
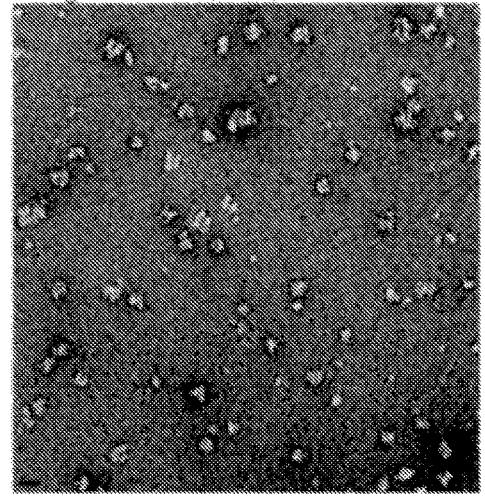
Figure 8:
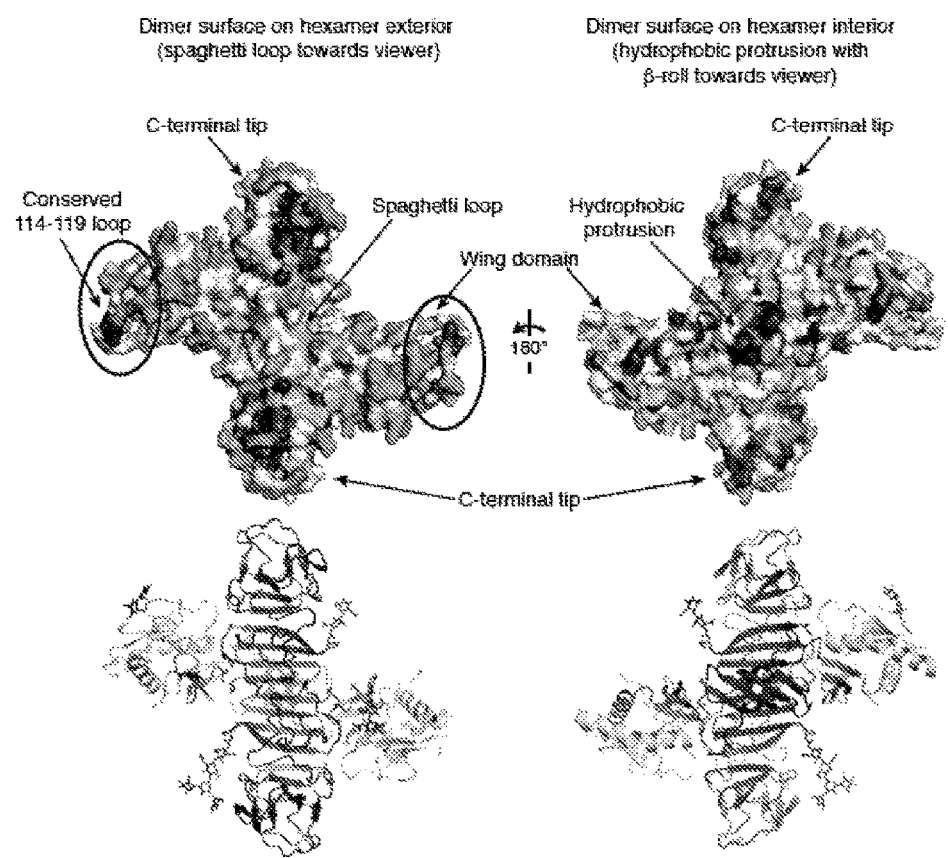
FIG. 8 shows NS1 sequence conservation mapped onto the protein surface. The NS1 surface is colored in a ramp (CONSURF) (Ashkenazy et al., *Nucleic Acids Res* 38, W529-533 (2010)) according to sequence conservation from the most conserved to the most divergent based on an alignment (Clustal) (Larkin et al., *Bioinformatics* 23, 2947-2948 (2007)) of NS1 sequences from 61 different flaviviruses.

On one side of the β-ladder plane, the β-roll and connector subdomain of the wing create a protrusion with a strikingly hydrophobic surface (FIGS. 2C, 3A). Extra electron densities at this surface were evident in the earliest maps, but were not fit with an atomic model until all regions of the polypeptide had been assigned to other densities (FIG. 7B, C). These densities were interpreted as three detergent molecules by considering all components of the crystallization solution and purification buffers. The hydrophobic character of the β-roll/connector protrusion is strongly conserved (FIGS. 8; 11). Furthermore, a dipeptide (Arg10-Gln11) implicated in interaction with the transmembrane protein NS4B (Youn et al., Evidence for a genetic and physical interaction between nonstructural proteins NS1 and NS4B that modulates replication of West Nile virus. *J Virol* 86, 7360-7371 (2012)) is located at the periphery of the hydrophobic surface in a loop of the β-roll (FIG. 8B). Thus the hydrophobic protrusion is a strong candidate for the membrane-interaction region of dimeric NS1 in the ER lumen, where NS1 plays a poorly defined but essential role in viral replication.

Figure 9:
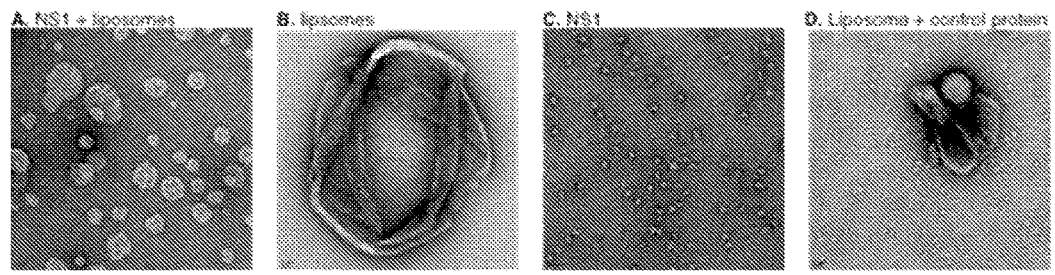
FIG. 9 shows NS1 remodeling of liposomes visualized by negative-stain EM. (A) Nano-particles resulting from WNV NS1 treatment of liposomes (composition 10:90 cholesterol:phosphatidylcholine) at pH 5.5 in a ratio of 585 lipid/cholesterol molecules per NS1 hexamer. (B) Untreated liposomes. (C) NS1 without liposomes. (D) Liposomes treated with a control protein (MycE tetramer (Akey et al., *J Mol Biol* 413, 438-450 (2011)) of similar molecular weight and isoelectric point to NS1. All images are on the same scale (scale bar 20 nm).

The ability of recombinant WNV NS1 to interact with membranes was investigated by incubating purified protein with liposomes and imaging the mixture by negative-stain EM. Upon exposure to NS1, the large heterogeneous liposomes were not only coated with NS1 but also were converted into much smaller lipid-protein nano-particles (FIG. 3B, FIG. 9). This ability to interact with and re-model membranes was completely unexpected and may have implications for the role of NS1 in organizing replication complexes or other functions in the viral infection cycle.

A "greasy finger" loop on the connector subdomain forms a prominent part of the hydrophobic protrusion (amino acids 158-161 joining β8 with β9) and was tested for its importance to virus viability. Mutations to this region (Gly159-Phe-Gly-Val162) were highly deleterious to virus replication as measured by plaque assay (Table 2). Substitution of charged amino acids in the conserved sequence (Gly-Phe-Gly-Val) in DEN2 NS1 (F160D and V162D) resulted in no detectable plaques. A single substitution (F160A) impaired virus viability (FIG. 10). The double mutant GF159/160AA was also non-viable, indicating that the loop conformation is important to function. Purified NS1 variants with these substitutions re-modeled liposomes similarly to the wild type (FIG. 10D), indicating that the observed phenotype is due to loss of effective interactions with transmembrane proteins of the replication complex.

Intracellular NS1 is thought to be predominantly dimeric whereas secreted NS1 is a soluble, hexameric protein-lipid particle (Muller et al., *Antiviral Res* 98, 192-208 (2013); Gutsche et al., *Proc Natl Acad Sci USA* 108, 8003-8008 (2011); Muller et al., *J Gen Virol* 93, 771-779 (2012)). A shift of dimeric to hexameric association of recombinant NS1 in solution through successive gel filtration steps in the absence of detergent (FIG. 6) was observed. A WNV NS1 hexamer exists on a threefold symmetry axis in crystal form 1. The form 1 hexamer, which resembles a tripod, (FIG. 4A, left panel) is formed primarily through polar contacts of the wing domains and hydrophobic contacts of the hydrophobic protrusions of adjacent dimers. This arrangement places the β-rolls in the interior of the hexamer while the outer hexamer surface contains the spaghetti loops and glycosylation sites. The WNV NS1 form 1 hexamer is splayed open at one end, and thus has a simple three-fold symmetry and not full hexameric symmetry. Hexamer formation creates a large, conserved hydrophobic interior surface of diameter 10-20 Å that is lined with detergent molecules (FIG. 4B, FIG. 8, FIG. 11). A different hexamer is found in WNV NS1 crystal form 2 (3 dimers per asymmetric unit) and in DEN2 NS1 crystals (1 dimer per asymmetric unit) (FIG. 4A, center and right panels). Here the dimers are again arranged with β-rolls facing the interior, as a loose, open hexamer with full D3 hexameric symmetry and dimensions ~80 Å along the central three-fold axis and ~110 Å in diameter.

The symmetric hexamers with images of the NS1 hexamer in solution are shown in FIG. 4C. Two-dimensional EM class averages of NS1 embedded in negative stain reveal particle projections that are similar to reprojections of the D3 symmetric hexamer assemblies observed in DEN2 NS1 and in WNV NS1 crystal form 2. The symmetric hexamers in the crystal structures and EM images, although without lipid, have similar overall dimensions to those of lipid-bound sNS1 secreted from virus-infected cells (Gutsche et al., *Proc Natl Acad Sci USA* 108, 8003-8008 (2011); Muller et al., *J Gen Virol* 93, 771-779 (2012)). Given the hydrophobic interior of the crystallized hexamer, it was concluded that the lipid-NS1 particle is organized similarly with β-rolls facing inward and the spaghetti loop, glycosylation sites and disordered loop facing outward.

Secreted NS1 is a diagnostic marker for flavivirus infection in serum (Alcon-LePoder et al., *Novartis Found Symp* 277, 233-247; discussion 247-253 (2006)), where immune system proteins encounter the sNS1 hexamer as a proteolipid particle. 108 NS1 epitopes elicited in response to immune stimulation by virus or full-length NS1 were identified (Vita et al., *Nucleic Acids Res* 38, D854-862 (2010)) and mapped onto the hexamer structure (FIG. 5A). The epitopes localize to a few hot spots, including the wing domain, the C-terminal tip of the β-ladder and the β-roll. A frequent epitope is the wing domain disordered loop, also the most accessible part of the NS1 hexamer. These epitopes are concentrated at a highly conserved Gly-Trp-Lys-Ala-Trp-Gly peptide (amino acids 114-119) (FIGS. 8 and 11), where the tryptophans are invariant and the lysine is highly conserved. Other frequently identified epitopes are in the C-terminal tip of the β-ladder, also highly accessible in the NS1 hexamer, and in the hydrophobic protrusion, indicating that the inside of the hexameric proteolipid is accessible to the immune recognition system at some point, perhaps by hexamer dissociation. Anti-NS1 antibodies have been implicated in immune pathogenesis in dengue virus (Falconar, *Clin Vaccine Immunol* 15, 549-561 (2008); Falconar, *Arch Virol* 142, 897-916 (1997); Henchal et al., *J Gen Virol* 69 (Pt 8), 2101-2107 (1988); Cheng et al., *Exp Biol Med* (Maywood) 234, 63-73 (2009); Liu et al., *J Biol Chem* 286, 9726-9736 (2011), and antibodies with cross-reactivity with human proteins have been mapped to the conserved wing peptide (Liu et al., supra) and to the conserved tip of the β-ladder (Cheng et al., supra).

Production of interferons and cytokines by the innate immune system is an important host defense against flaviviruses, particularly through the pattern recognition receptors RIG-I, MDA5 and TLR3 (Suthar et al., *Nat Rev Microbiol* 11, 115-128 (2013); Wilson et al., *J Virol* 82, 8262-8271 (2008). The α/β subdomain of the NS1 wing resembles a helicase domain of RIG-I (Civril et al., *EMBO Rep* 12, 1127-1134 (2011)) and MDA5 (Motz et al., *Science* 339, 690-693 (2013)). (FIG. 5B). These cytoplasmic helicase domains recognize pathogenic RNAs and trigger the antiviral response.

TABLE 1

Crystallographic data and refinement statistics

|  | WNV form 1 | | WNV form 2 | DEN2 |
|---|---|---|---|---|
|  | S anomalous | Native | Native | Native |
| Data | | | | |
| Space group | P321 | P321 | P3 | H3 |
| Unit cell a = b, c (Å) | 167.80, 93.82 | 168.69, 92.89 | 186.89, 81.77 | 176.34, 81.94 |
| Wavelength (Å) | 1.7462 | 1.0332 | 1.0332 | 0.97934 |
| $d_{min}$ (Å) | 3.00 (3.16-3.00)[1] | 2.59 (2.68-2.59) | 2.75 (2.80-2.75) | 3.00 (3.18-3.00) |
| Observations (#) | 5,732,471 (667,694) | 857,143 (28,659) | 489,465 (26,765) | 35,174 (5,648) |
| Unique reflections | 61,538 (8,844)[2] | 47,162 (4,377) | 82,996 (4,565) | 17,731 (2,893) |
| Avg I/$\sigma_I$ | 27.8 (2.5)[2] | 21.1 (1.2) | 7.4 (1.0) | 8.8 (1.3) |
| $R_{merge}$ | 0.292 (4.187)[2] | 0.091 (1.558) | 0.244 (2.410) | 0.070 (0.613) |
| $CC_{1/2}$[3] | 0.999 (0.442)[2] | 0.999 (0.531) | 0.992 (0.457) | 0.996 (0.444) |
| CC*[4] | 1.000 (0.771)[2] | 1.000 (0.833) | 0.998 (0.792) | 0.999 (0.784) |
| Completeness % | 100.0 (100.0)[2] | 99.5 (94.8) | 100.0 (1000) | 94.3 (95.1) |
| Wilson B (Å$^2$) | 88.2 | 83.4 | 67.8 | 73.7 |
| Refinement | | | | |
| Reflections (#) | | 46,980 | 82,941 | 17,724 |
| $R_{work}$ | | 0.172 (0.377) | 0.195 (0.341) | 0.185 (0.314) |
| $R_{free}$ | | 0.199 (0.455) | 0.235 (0.316) | 0.218 (0.318) |
| RMSD bonds (Å) | | 0.008 | 0.004 | 0.004 |
| RMSD angles (°) | | 1.115 | 0.820 | 0.712 |
| Atoms (#) | | | | |
| Protein | | 5351 | 15996 | 5098 |
| Solvent | | 218 | 15 ($SO_4^{-2}$) | 0 |
| Carbohydrate/Det | | 229 | 84 | 28 |
| Avg B-factors (Å$^2$) | | | | |
| Protein | | 85.0 | 82.8 | 88.6 |
| Solvent | | 77.3 | 94.9 | |
| Carbohydrate/Det | | 126.4 | 101.2 | 67.3 |
| Ramachandran | | | | |
| Favored (%) | | 94.8 | 96.4 | 94.7 |
| Allowed (%) | | 5.2 | 3.3 | 5.3 |
| Outliers (%) | | 0 | 0.3 | 0 |

[1]Numbers in parentheses refer to the outermost shell of data.
[2]Anomalous pairs are treated separately.
[3]$CC_{1/2}$ is the correlation of one-half of the observations with the other half (29, 30).

[4]$CC^* = \sqrt{\dfrac{2CC_{1/2}}{1+CC_{1/2}}}$ (29, 30)

TABLE 2

Phenotypic Characteristics of DEN2 NS1 Mutations

| Virus | Plaque size | Titer (PFU[1]/mL) |
|---|---|---|
| Wild type | 3 mm | 4.8 × 10$^6$ |
| F160A | 1 mm | 6.0 × 10$^3$ |
| F160D | Not recovered | — |
| GF159/160AA | Not recovered | — |
| V162D | Not recovered | — |

[1]PFU = plaque-forming units

Although a variety of embodiments have been described in connection with the present disclosure, it should be understood that the claimed invention should not be unduly limited to such specific embodiments. Indeed, various modifications and variations of the described compositions and methods of the invention will be apparent to those of ordinary skill in the art and are intended to be within the scope of the following claims.

We claim:

1. A composition for inducing an immune response, comprising:
   a) one or more peptides selected from the group consisting of SEQ ID NOs: 51-54 and peptides that are at least 80% identical to SEQ ID NOs: 51-54; and
   b) an adjuvant that enhances the ability of said one or more peptides to induce an immune response.

2. The composition of claim 1, wherein said peptides are at least 90% identical to SEQ ID NOs: 51-54.

3. The composition of claim 1, wherein said peptides are at least 95% identical to SEQ ID NOs: 51-54.

4. The composition of claim 1, wherein said adjuvant is selected from the group consisting of an insoluble suspension of acylated sugars, cationically or anionically derivatized polysaccharides, diphosphoryl lipid A, 3-O-deacylated variants of diphosporyl lipid A, QS7, QS17, QS21, unmethylated CpG dinucleotides, interleukin-2, interferon-γ, interleukin-4, macrophage colony stimulating factor, tumor necrosis factor, monophosphoryl lipid A, and OM-174.

5. A method of inducing an immune response in a subject, comprising: administering the composition of claim 1 to a subject.

6. A kit comprising the composition of claim 1.

7. The kit of claim 6, wherein said kit further comprises a device for administering said composition to a subject.

8. The kit of claim 7, wherein said device is selected from the group consisting of a syringe, a needle, and an intranasal delivery device.

* * * * *

SEQUENCE LISTING

<160> NUMBER OF SEQ ID NOS: 142

<210> SEQ ID NO 1
<211> LENGTH: 13
<212> TYPE: PRT
<213> ORGANISM: Dengue virus type 1

<400> SEQUENCE: 1

```
Lys Arg Leu Ser Ala Ala Ile Gly Lys Ala Trp Glu Glu
1               5                   10
```

<210> SEQ ID NO 2
<211> LENGTH: 13
<212> TYPE: PRT
<213> ORGANISM: Dengue virus type 2

<400> SEQUENCE: 2

```
Ser Lys Leu Ala Ser Ala Ile Gln Lys Ala His Glu Glu
1               5                   10
```

<210> SEQ ID NO 3
<211> LENGTH: 13
<212> TYPE: PRT
<213> ORGANISM: Dengue virus type 3

<400> SEQUENCE: 3

```
Lys Arg Val Ala Thr Ala Ile Ala Gly Ala Trp Glu Asn
1               5                   10
```

<210> SEQ ID NO 4
<211> LENGTH: 13
<212> TYPE: PRT
<213> ORGANISM: Dengue virus type 4

<400> SEQUENCE: 4

```
Ala Arg Leu Ala Ser Ala Ile Leu Asn Ala His Lys Asp
1               5                   10
```

<210> SEQ ID NO 5
<211> LENGTH: 14
<212> TYPE: PRT
<213> ORGANISM: Dengue virus type 1

<400> SEQUENCE: 5

```
Gln Gly Arg Lys Met Ile Gly Pro Gln Pro Met Glu His Lys
1               5                   10
```

<210> SEQ ID NO 6
<211> LENGTH: 14
<212> TYPE: PRT
<213> ORGANISM: Dengue virus type 2

<400> SEQUENCE: 6

```
Val Gly Lys Arg Ser Leu Gln Pro Gln Pro Thr Glu Leu Arg
1               5                   10
```

<210> SEQ ID NO 7
<211> LENGTH: 14
<212> TYPE: PRT
<213> ORGANISM: Dengue virus type 3

<400> SEQUENCE: 7

```
Gln Gly Lys Arg Thr Leu Thr Pro Gln Pro Met Glu Leu Lys
1               5                   10
```

<210> SEQ ID NO 8
<211> LENGTH: 14
<212> TYPE: PRT
<213> ORGANISM: Dengue virus type 4

<400> SEQUENCE: 8

```
Lys Gly Lys Arg Ala Leu Thr Pro Pro Val Ser Asp Leu Lys
```

<210> SEQ ID NO 9
<211> LENGTH: 9
<212> TYPE: PRT
<213> ORGANISM: Dengue virus type 1

<400> SEQUENCE: 9

Asn Thr Pro Glu Cys Pro Asp Asp Gln
1               5

<210> SEQ ID NO 10
<211> LENGTH: 9
<212> TYPE: PRT
<213> ORGANISM: Dengue virus type 2

<400> SEQUENCE: 10

Glu Thr Ala Glu Cys Pro Asn Thr Asn
1               5

<210> SEQ ID NO 11
<211> LENGTH: 9
<212> TYPE: PRT
<213> ORGANISM: Dengue virus type 3

<400> SEQUENCE: 11

Ser Thr Pro Glu Cys Pro Ser Ala Ser
1               5

<210> SEQ ID NO 12
<211> LENGTH: 9
<212> TYPE: PRT
<213> ORGANISM: Dengue virus type 4

<400> SEQUENCE: 12

Asp Thr Ser Glu Cys Pro Asn Glu Arg
1               5

<210> SEQ ID NO 13
<211> LENGTH: 9
<212> TYPE: PRT
<213> ORGANISM: Dengue virus type 1

<400> SEQUENCE: 13

Ser Tyr Thr Gln Val Cys Asp Pro Arg
1               5

<210> SEQ ID NO 14
<211> LENGTH: 9
<212> TYPE: PRT
<213> ORGANISM: Dengue virus type 2

<400> SEQUENCE: 14

Lys Gln Asp Val Phe Cys Asp Ser Lys
1               5

<210> SEQ ID NO 15
<211> LENGTH: 9
<212> TYPE: PRT
<213> ORGANISM: Dengue virus type 3

<400> SEQUENCE: 15

Val Tyr Thr Gln Leu Cys Asp His Arg
1               5

```
<210> SEQ ID NO 16
<211> LENGTH: 9
<212> TYPE: PRT
<213> ORGANISM: Dengue virus type 4

<400> SEQUENCE: 16

Gly Ser Ser Glu Val Cys Asp His Arg
1               5

<210> SEQ ID NO 17
<211> LENGTH: 9
<212> TYPE: PRT
<213> ORGANISM: Dengue virus type 1

<400> SEQUENCE: 17

Glu Lys Asn Glu Thr Trp Lys Leu Ala
1               5

<210> SEQ ID NO 18
<211> LENGTH: 9
<212> TYPE: PRT
<213> ORGANISM: Dengue virus type 2

<400> SEQUENCE: 18

Ala Leu Asn Asp Thr Trp Lys Ile Glu
1               5

<210> SEQ ID NO 19
<211> LENGTH: 9
<212> TYPE: PRT
<213> ORGANISM: Dengue virus type 3

<400> SEQUENCE: 19

Gln Lys Asn Gly Ser Trp Lys Leu Glu
1               5

<210> SEQ ID NO 20
<211> LENGTH: 9
<212> TYPE: PRT
<213> ORGANISM: Dengue virus type 4

<400> SEQUENCE: 20

Ser Lys Asn Gln Thr Trp Gln Ile Glu
1               5

<210> SEQ ID NO 21
<211> LENGTH: 6
<212> TYPE: PRT
<213> ORGANISM: Dengue virus type 1

<400> SEQUENCE: 21

Ile Tyr Gly Gly Pro Ile
1               5

<210> SEQ ID NO 22
<211> LENGTH: 6
<212> TYPE: PRT
<213> ORGANISM: Dengue virus type 2

<400> SEQUENCE: 22

Asn Leu Ala Gly Pro Val
1               5

<210> SEQ ID NO 23
```

```
<211> LENGTH: 6
<212> TYPE: PRT
<213> ORGANISM: Dengue virus type 3

<400> SEQUENCE: 23

Ser Leu Ala Gly Pro Ile
1               5

<210> SEQ ID NO 24
<211> LENGTH: 6
<212> TYPE: PRT
<213> ORGANISM: Dengue virus type 4

<400> SEQUENCE: 24

Ser Tyr Ala Gly Pro Phe
1               5

<210> SEQ ID NO 25
<211> LENGTH: 10
<212> TYPE: PRT
<213> ORGANISM: Dengue virus type 1

<400> SEQUENCE: 25

Tyr Arg Pro Gly Tyr Ser Thr Gln Thr Ala
1               5                   10

<210> SEQ ID NO 26
<211> LENGTH: 10
<212> TYPE: PRT
<213> ORGANISM: Dengue virus type 2

<400> SEQUENCE: 26

Asn Arg Pro Gly Tyr Tyr Thr Gln Thr Ala
1               5                   10

<210> SEQ ID NO 27
<211> LENGTH: 10
<212> TYPE: PRT
<213> ORGANISM: Dengue virus type 3

<400> SEQUENCE: 27

His Arg Pro Gly Tyr His Thr Gln Thr Ala
1               5                   10

<210> SEQ ID NO 28
<211> LENGTH: 10
<212> TYPE: PRT
<213> ORGANISM: Dengue virus type 4

<400> SEQUENCE: 28

Tyr Arg Gln Gly Tyr Ala Thr Gln Thr Val
1               5                   10

<210> SEQ ID NO 29
<211> LENGTH: 8
<212> TYPE: PRT
<213> ORGANISM: Dengue virus type 1

<400> SEQUENCE: 29

Val Val Asp Glu His Cys Gly Asn
1               5

<210> SEQ ID NO 30
<211> LENGTH: 8
<212> TYPE: PRT
```

```
<213> ORGANISM: Dengue virus type 2

<400> SEQUENCE: 30

Val Val Thr Glu Asp Cys Gly Asn
1               5

<210> S

```
Asp Met Gly Cys Val Val Ser Trp Ser Gly Lys Glu Leu Lys Cys Gly
1               5                   10                  15

Ser Gly Ile Phe Val Val Asp Asn Val His Thr Trp Thr
            20                  25

<210> SEQ ID NO 37
<211> LENGTH: 29
<212> TYPE: PRT
<213> ORGANISM: West Nile virus

<400> SEQUENCE: 37

Asp Thr Gly Cys Ala Ile Asp Ile Ser Arg Gln Glu Leu Arg Cys Gly
1               5                   10                  15

Ser Gly Val Phe Ile His Asn Asp Val Glu Ala Trp Met
            20                  25

<210> SEQ ID NO 38
<211> LENGTH: 29
<212> TYPE: PRT
<213> ORGANISM: Japanese encephalitis virus

<400> SEQUENCE: 38

Asp Thr Gly Cys Ala Ile Asp Ile Thr Arg Lys Glu Met Arg Cys Gly
1               5                   10                  15

Ser Gly Ile Phe Val His Asn Asp Val Glu Ala Trp Val
            20                  25

<210> SEQ ID NO 39
<211> LENGTH: 22
<212> TYPE: PRT
<213> ORGANISM: Dengue virus type 1

<400> SEQUENCE: 39

Pro Met Glu Tyr Lys Tyr Ser Trp Lys Ser Trp Gly Lys Ala Lys Ile
1               5                   10                  15

Ile Gly Ala Asp Val Gln
            20

<210> SEQ ID NO 40
<211> LENGTH: 22
<212> TYPE: PRT
<213> ORGANISM: Dengue virus type 2

<400> SEQUENCE: 40

Pro Thr Glu Leu Lys Tyr Ser Trp Lys Thr Trp Gly Lys Ala Lys Met
1               5                   10                  15

Leu Ser Thr Glu Ser His
            20

<210> SEQ ID NO 41
<211> LENGTH: 22
<212> TYPE: PRT
<213> ORGANISM: Dengue virus type 3

<400> SEQUENCE: 41

Pro Met Glu Leu Lys Tyr Ser Trp Lys Thr Trp Gly Leu Ala Lys Ile
1               5                   10                  15

Val Thr Ala Glu Thr Gln
            20

<210> SEQ ID NO 42
<211> LENGTH: 22
```

-continued

```
<212> TYPE: PRT
<213> ORGANISM: Dengue virus type 4

<400> SEQUENCE: 42

Val Ser Asp Leu Lys Tyr Ser Trp Lys Thr Trp Gly Lys Ala Lys Ile
1               5                   10                  15

Phe Thr Pro Glu Ala Arg
            20

<210> SEQ ID NO 43
<211> LENGTH: 22
<212> TYPE: PRT
<213> ORGANISM: West Nile virus

<400> SEQUENCE: 43

Thr Glu Lys Leu Glu Ile Gly Trp Lys Ala Trp Gly Lys Ser Ile Leu
1               5                   10                  15

Phe Ala Pro Glu Leu Ala
            20

<210> SEQ ID NO 44
<211> LENGTH: 22
<212> TYPE: PRT
<213> ORGANISM: Japanese encephalitis virus

<400> SEQUENCE: 44

Gln Glu Lys Phe Glu Met Gly Trp Lys Ala Trp Gly Lys Ser Leu Leu
1               5                   10                  15

Phe Ala Pro Glu Leu Ala
            20

<210> SEQ ID NO 45
<211> LENGTH: 50
<212> TYPE: PRT
<213> ORGANISM: Dengue virus type 1

<400> SEQUENCE: 45

Glu Gln Tyr Lys Phe Gln Ala Asp Ser Pro Lys Arg Leu Ser Ala Ala
1               5                   10                  15

Ile Gly Lys Ala Trp Glu Glu Gly Val Cys Gly Ile Arg Ser Ala Thr
            20                  25                  30

Arg Leu Glu Asn Ile Met Trp Lys Gln Ile Ser Asn Glu Leu Asn His
        35                  40                  45

Ile Leu
    50

<210> SEQ ID NO 46
<211> LENGTH: 50
<212> TYPE: PRT
<213> ORGANISM: Dengue virus type 2

<400> SEQUENCE: 46

Glu Gln Tyr Lys Phe Gln Pro Glu Ser Pro Ser Lys Leu Ala Ser Ala
1               5                   10                  15

Ile Gln Lys Ala His Glu Glu Gly Ile Cys Gly Ile Arg Ser Val Thr
            20                  25                  30

Arg Leu Glu Asn Leu Met Trp Lys Gln Ile Thr Pro Glu Leu Asn His
        35                  40                  45

Ile Leu
    50
```

<210> SEQ ID NO 47
<211> LENGTH: 50
<212> TYPE: PRT
<213> ORGANISM: Dengue virus type 3

<400> SEQUENCE: 47

```
Glu Gln Tyr Lys Phe Gln Ala Asp Ser Pro Lys Arg Val Ala Thr Ala
1               5                   10                  15

Ile Ala Gly Ala Trp Glu Asn Gly Val Cys Gly Ile Arg Ser Thr Thr
            20                  25                  30

Arg Met Glu Asn Leu Leu Trp Lys Gln Ile Ala Asn Glu Leu Asn Tyr
        35                  40                  45

Ile Leu
    50
```

<210> SEQ ID NO 48
<211> LENGTH: 50
<212> TYPE: PRT
<213> ORGANISM: Dengue virus type 4

<400> SEQUENCE: 48

```
Glu Gln Tyr Lys Phe Gln Pro Glu Ser Pro Ala Arg Leu Ala Ser Ala
1               5                   10                  15

Ile Leu Asn Ala His Lys Asp Gly Val Cys Gly Ile Arg Ser Thr Thr
            20                  25                  30

Arg Leu Glu Asn Val Met Trp Lys Gln Ile Thr Asn Glu Leu Asn Tyr
        35                  40                  45

Val Leu
    50
```

<210> SEQ ID NO 49
<211> LENGTH: 50
<212> TYPE: PRT
<213> ORGANISM: West Nile virus

<400> SEQUENCE: 49

```
Asp Arg Tyr Lys Tyr Tyr Pro Glu Thr Pro Gln Gly Leu Ala Lys Ile
1               5                   10                  15

Ile Gln Lys Ala His Lys Glu Gly Val Cys Gly Leu Arg Ser Val Ser
            20                  25                  30

Arg Leu Glu His Gln Met Trp Glu Ala Val Lys Asp Glu Leu Asn Thr
        35                  40                  45

Leu Leu
    50
```

<210> SEQ ID NO 50
<211> LENGTH: 50
<212> TYPE: PRT
<213> ORGANISM: Japanese encephalitis virus

<400> SEQUENCE: 50

```
Asp Arg Tyr Lys Tyr Leu Pro Glu Thr Pro Arg Ser Leu Ala Lys Ile
1               5                   10                  15

Val His Lys Ala His Gln Glu Gly Val Cys Gly Val Arg Ser Val Thr
            20                  25                  30

Arg Leu Glu His Gln Met Trp Glu Ser Val Arg Asp Glu Leu Asn Val
        35                  40                  45

Leu Leu
    50
```

<210> SEQ ID NO 51
<211> LENGTH: 50
<212> TYPE: PRT
<213> ORGANISM: Dengue virus type 1

<400> SEQUENCE: 51

Leu Glu Asn Asp Met Lys Phe Thr Val Val Gly Asp Val Ser Gly
1               5                   10                  15

Ile Leu Ala Gln Gly Lys Lys Met Ile Arg Pro Gln Pro Met Glu Tyr
            20                  25                  30

Lys Tyr Ser Trp Lys Ser Trp Gly Lys Ala Lys Ile Ile Gly Ala Asp
        35                  40                  45

Val Gln
    50

<210> SEQ ID NO 52
<211> LENGTH: 50
<212> TYPE: PRT
<213> ORGANISM: Dengue virus type 2

<400> SEQUENCE: 52

Ser Glu Asn Glu Val Lys Leu Thr Ile Met Thr Gly Asp Ile Lys Gly
1               5                   10                  15

Ile Met Gln Ala Gly Lys Arg Ser Leu Arg Pro Gln Pro Thr Glu Leu
            20                  25                  30

Lys Tyr Ser Trp Lys Thr Trp Gly Lys Ala Lys Met Leu Ser Thr Glu
        35                  40                  45

Ser His
    50

<210> SEQ ID NO 53
<211> LENGTH: 50
<212> TYPE: PRT
<213> ORGANISM: Dengue virus type 3

<400> SEQUENCE: 53

Trp Glu Asn Asp Ile Lys Leu Thr Val Val Gly Asp Ile Thr Gly
1               5                   10                  15

Val Leu Glu Gln Gly Lys Arg Thr Leu Thr Pro Gln Pro Met Glu Leu
            20                  25                  30

Lys Tyr Ser Trp Lys Thr Trp Gly Leu Ala Lys Ile Val Thr Ala Glu
        35                  40                  45

Thr Gln
    50

<210> SEQ ID NO 54
<211> LENGTH: 50
<212> TYPE: PRT
<213> ORGANISM: Dengue virus type 4

<400> SEQUENCE: 54

Trp Glu Gly Gly His Asp Leu Thr Val Val Ala Gly Asp Val Lys Gly
1               5                   10                  15

Val Leu Thr Lys Gly Lys Arg Ala Leu Thr Pro Pro Val Ser Asp Leu
            20                  25                  30

Lys Tyr Ser Trp Lys Thr Trp Gly Lys Ala Lys Ile Phe Thr Pro Glu
        35                  40                  45

Ala Arg

<210> SEQ ID NO 55
<211> LENGTH: 50
<212> TYPE: PRT
<213> ORGANISM: West Nile virus

<400> SEQUENCE: 55

Lys Glu Asn Gly Val Asp Leu Ser Val Val Glu Lys Gln Glu Gly
1               5                   10                  15

Met Tyr Lys Ser Ala Pro Lys Arg Leu Thr Ala Thr Thr Glu Lys Leu
                20                  25                  30

Glu Ile Gly Trp Lys Ala Trp Gly Lys Ser Ile Leu Phe Ala Pro Glu
            35                  40                  45

Leu Ala
    50

<210> SEQ ID NO 56
<211> LENGTH: 50
<212> TYPE: PRT
<213> ORGANISM: Japanese encephalitis virus

<400> SEQUENCE: 56

Lys Glu Asn Ala Val Asp Leu Ser Val Val Asn Lys Pro Val Gly
1               5                   10                  15

Arg Tyr Arg Ser Ala Pro Lys Arg Leu Ser Met Thr Gln Glu Lys Phe
                20                  25                  30

Glu Met Gly Trp Lys Ala Trp Gly Lys Ser Leu Leu Phe Ala Pro Glu
            35                  40                  45

Leu Ala
    50

<210> SEQ ID NO 57
<211> LENGTH: 45
<212> TYPE: PRT
<213> ORGANISM: Dengue virus type 1

<400> SEQUENCE: 57

Asn Ser Thr Phe Ile Ile Asp Gly Pro Asn Thr Pro Glu Cys Pro Asp
1               5                   10                  15

Asp Gln Arg Ala Trp Asn Ile Trp Glu Val Glu Asp Tyr Gly Phe Gly
                20                  25                  30

Ile Phe Thr Thr Asn Ile Trp Leu Lys Leu Arg Asp Ser
            35                  40                  45

<210> SEQ ID NO 58
<211> LENGTH: 45
<212> TYPE: PRT
<213> ORGANISM: Dengue virus type 2

<400> SEQUENCE: 58

Asn Gln Thr Phe Leu Ile Asp Gly Pro Glu Thr Ala Glu Cys Pro Asn
1               5                   10                  15

Thr Asn Arg Ala Trp Asn Ser Leu Glu Val Glu Asp Tyr Gly Phe Gly
                20                  25                  30

Val Phe Thr Thr Asn Ile Trp Leu Lys Leu Lys Glu Lys
            35                  40                  45

<210> SEQ ID NO 59
<211> LENGTH: 45

-continued

```
<212> TYPE: PRT
<213> ORGANISM: Dengue virus type 3

<400> SEQUENCE: 59

Asn Ser Ser Phe Ile Ile Asp Gly Pro Ser Thr Pro Glu Cys Pro Ser
1               5                   10                  15

Ala Ser Arg Ala Trp Asn Val Trp Glu Val Glu Asp Tyr Gly Phe Gly
            20                  25                  30

Val Phe Thr Thr Asn Ile Trp Leu Lys Leu Arg Glu Val
        35                  40                  45

<210> SEQ ID NO 60
<211> LENGTH: 45
<212> TYPE: PRT
<213> ORGANISM: Dengue virus type 4

<400> SEQUENCE: 60

Asn Ser Thr Phe Leu Ile Asp Gly Pro Asp Thr Ser Glu Cys Pro Asn
1               5                   10                  15

Glu Arg Arg Ala Trp Asn Ser Leu Glu Val Glu Asp Tyr Gly Phe Gly
            20                  25                  30

Met Phe Thr Thr Asn Ile Trp Met Lys Phe Arg Glu Gly
        35                  40                  45

<210> SEQ ID NO 61
<211> LENGTH: 45
<212> TYPE: PRT
<213> ORGANISM: West Nile virus

<400> SEQUENCE: 61

Asn Asn Thr Phe Val Val Asp Gly Pro Glu Thr Lys Glu Cys Pro Thr
1               5                   10                  15

Gln Asn Arg Ala Trp Asn Ser Leu Glu Val Glu Asp Phe Gly Phe Gly
            20                  25                  30

Leu Thr Ser Thr Arg Met Phe Leu Lys Val Arg Glu Ser
        35                  40                  45

<210> SEQ ID NO 62
<211> LENGTH: 45
<212> TYPE: PRT
<213> ORGANISM: Japanese encephalitis virus

<400> SEQUENCE: 62

Asn Ser Ser Phe Val Val Asp Gly Pro Glu Thr Lys Glu Cys Pro Asp
1               5                   10                  15

Glu Arg Arg Ala Trp Asn Ser Met Gln Ile Glu Asp Phe Gly Phe Gly
            20                  25                  30

Ile Thr Ser Thr Arg Val Trp Leu Lys Ile Arg Glu Glu
        35                  40                  45

<210> SEQ ID NO 63
<211> LENGTH: 9
<212> TYPE: PRT
<213> ORGANISM: Dengue virus type 1

<400> SEQUENCE: 63

Trp Ser Asn Gly Val Leu Glu Ser Glu
1               5

<210> SEQ ID NO 64
<211> LENGTH: 9
```

-continued

<212> TYPE: PRT
<213> ORGANISM: Dengue virus type 2

<400> SEQUENCE: 64

Trp Ser Asn Gly Val Leu Glu Ser Glu
1               5

<210> SEQ ID NO 65
<211> LENGTH: 9
<212> TYPE: PRT
<213> ORGANISM: Dengue virus type 3

<400> SEQUENCE: 65

Trp Ser Asn Gly Val Leu Glu Ser Asp
1               5

<210> SEQ ID NO 66
<211> LENGTH: 9
<212> TYPE: PRT
<213> ORGANISM: Dengue virus type 4

<400> SEQUENCE: 66

Trp Ser Asn Gly Val Leu Glu Ser Gln
1               5

<210> SEQ ID NO 67
<211> LENGTH: 9
<212> TYPE: PRT
<213> ORGANISM: West Nile virus

<400> SEQUENCE: 67

Trp Gly Asp Gly Val Leu Glu Ser Asp
1               5

<210> SEQ ID NO 68
<211> LENGTH: 9
<212> TYPE: PRT
<213> ORGANISM: Japanese encephalitis virus

<400> SEQUENCE: 68

Trp Gly Asp Gly Val Glu Glu Ser Glu
1               5

<210> SEQ ID NO 69
<211> LENGTH: 50
<212> TYPE: PRT
<213> ORGANISM: Dengue virus type 1

<400> SEQUENCE: 69

Ala Gly Pro Trp His Leu Gly Lys Leu Glu Leu Asp Phe Asp Leu Cys
1               5                   10                  15

Glu Gly Thr Thr Val Val Val Asp Glu His Cys Gly Asn Arg Gly Pro
                20                  25                  30

Ser Leu Arg Thr Thr Thr Val Thr Gly Lys Ile Ile His Glu Trp Cys
            35                  40                  45

Cys Arg
    50

<210> SEQ ID NO 70
<211> LENGTH: 50
<212> TYPE: PRT
<213> ORGANISM: Dengue virus type 2

<400> SEQUENCE: 70

```
Thr Gly Pro Trp His Leu Gly Lys Leu Glu Met Asp Phe Asp Phe Cys
1               5                   10                  15

Asp Gly Thr Thr Val Val Val Thr Glu Asp Cys Gly Asn Arg Gly Pro
            20                  25                  30

Ser Leu Arg Thr Thr Thr Ala Ser Gly Lys Leu Ile Thr Glu Trp Cys
        35                  40                  45

Cys Arg
    50

<210> SEQ ID NO 71
<211> LENGTH: 50
<212> TYPE: PRT
<213> ORGANISM: Dengue virus type 3

<400> SEQUENCE: 71

Ala Gly Pro Trp His Leu Gly Lys Leu Glu Leu Asp Phe Asn Tyr Cys
1               5                   10                  15

Glu Gly Thr Thr Val Val Ile Ser Glu Asn Cys Gly Thr Arg Gly Pro
            20                  25                  30

Ser Leu Arg Thr Thr Thr Val Ser Gly Lys Leu Ile His Glu Trp Cys
        35                  40                  45

Cys Arg
    50

<210> SEQ ID NO 72
<211> LENGTH: 50
<212> TYPE: PRT
<213> ORGANISM: Dengue virus type 4

<400> SEQUENCE: 72

Val Gly Pro Trp His Leu Gly Lys Leu Glu Ile Asp Phe Gly Glu Cys
1               5                   10                  15

Pro Gly Thr Thr Val Thr Ile Gln Glu Asp Cys Asp His Arg Gly Pro
            20                  25                  30

Ser Leu Arg Thr Thr Thr Ala Ser Gly Lys Leu Val Thr Gln Trp Cys
        35                  40                  45

Cys Arg
    50

<210> SEQ ID NO 73
<211> LENGTH: 50
<212> TYPE: PRT
<213> ORGANISM: West Nile virus

<400> SEQUENCE: 73

Gln Gly Pro Trp Asp Glu Gly Arg Val Glu Ile Asp Phe Asp Tyr Cys
1               5                   10                  15

Pro Gly Thr Thr Val Thr Leu Ser Glu Ser Cys Gly His Arg Gly Pro
            20                  25                  30

Ala Thr Arg Thr Thr Thr Glu Ser Gly Lys Leu Ile Thr Asp Trp Cys
        35                  40                  45

Cys Arg
    50

<210> SEQ ID NO 74
<211> LENGTH: 50
<212> TYPE: PRT
<213> ORGANISM: Japanese encephalitis virus
```

```
<400> SEQUENCE: 74

Gln Gly Pro Trp Asp Glu Asn Gly Leu Val Pro Gly Leu Asp Tyr Cys
1               5                   10                  15

Pro Gly Thr Lys Val Thr Ile Thr Glu Asp Cys Gly Lys Arg Gly Pro
            20                  25                  30

Ser Ile Arg Thr Thr Thr Asp Ser Gly Lys Leu Ile Thr Asp Trp Cys
        35                  40                  45

Cys Arg
    50

<210> SEQ ID NO 75
<211> LENGTH: 38
<212> TYPE: PRT
<213> ORGANISM: Dengue virus type 1

<400> SEQUENCE: 75

Ser Cys Thr Leu Pro Pro Leu Arg Phe Lys Gly Glu Asp Gly Cys Trp
1               5                   10                  15

Tyr Gly Met Glu Ile Arg Pro Val Lys Glu Lys Glu Asn Leu Val
            20                  25                  30

Lys Ser Met Val Ser Ala
        35

<210> SEQ ID NO 76
<211> LENGTH: 38
<212> TYPE: PRT
<213> ORGANISM: Dengue virus type 2

<400> SEQUENCE: 76

Ser Cys Thr Leu Pro Pro Leu Arg Tyr Arg Gly Glu Asp Gly Cys Trp
1               5                   10                  15

Tyr Gly Met Glu Ile Arg Pro Leu Lys Glu Lys Glu Asn Leu Val
            20                  25                  30

Asn Ser Leu Val Thr Ala
        35

<210> SEQ ID NO 77
<211> LENGTH: 38
<212> TYPE: PRT
<213> ORGANISM: Dengue virus type 3

<400> SEQUENCE: 77

Ser Cys Thr Leu Pro Pro Leu Arg Tyr Met Gly Glu Asp Gly Cys Trp
1               5                   10                  15

Tyr Gly Met Glu Ile Arg Pro Ile Asn Glu Lys Glu Asn Met Val
            20                  25                  30

Lys Ser Leu Ala Ser Ala
        35

<210> SEQ ID NO 78
<211> LENGTH: 38
<212> TYPE: PRT
<213> ORGANISM: Dengue virus type 4

<400> SEQUENCE: 78

Ser Cys Thr Met Pro Pro Leu Arg Phe Leu Gly Glu Asp Gly Cys Trp
1               5                   10                  15

Tyr Gly Met Glu Ile Arg Pro Leu Ser Glu Lys Glu Asn Met Val
            20                  25                  30
```

Lys Ser Gln Val Thr Ala
        35

<210> SEQ ID NO 79
<211> LENGTH: 38
<212> TYPE: PRT
<213> ORGANISM: West Nile virus

<400> SEQUENCE: 79

Ser Cys Thr Leu Pro Pro Leu Arg Tyr Gln Thr Asp Ser Gly Cys Trp
1               5                   10                  15

Tyr Gly Met Glu Ile Arg Pro Gln Arg His Asp Glu Lys Thr Leu Val
            20                  25                  30

Gln Ser Gln Val Asn Ala
        35

<210> SEQ ID NO 80
<211> LENGTH: 38
<212> TYPE: PRT
<213> ORGANISM: Japanese encephalitis virus

<400> SEQUENCE: 80

Ser Cys Ser Leu Pro Pro Leu Arg Phe Arg Thr Glu Asn Gly Cys Trp
1               5                   10                  15

Tyr Gly Met Glu Ile Arg Pro Val Arg His Asp Glu Thr Thr Leu Val
            20                  25                  30

Arg Ser Gln Val Asp Ala
        35

<210> SEQ ID NO 81
<211> LENGTH: 352
<212> TYPE: PRT
<213> ORGANISM: West Nile virus

<400> SEQUENCE: 81

Asp Thr Gly Cys Ala Ile Asp Ile Ser Arg Gln Glu Leu Arg Cys Gly
1               5                   10                  15

Ser Gly Val Phe Ile His Asn Asp Val Glu Ala Trp Met Asp Arg Tyr
            20                  25                  30

Lys Tyr Tyr Pro Glu Thr Pro Gln Gly Leu Ala Lys Ile Ile Gln Lys
        35                  40                  45

Ala His Lys Glu Gly Val Cys Gly Leu Arg Ser Val Ser Arg Leu Glu
    50                  55                  60

His Gln Met Trp Glu Ala Val Lys Asp Glu Leu Asn Thr Leu Leu Lys
65                  70                  75                  80

Glu Asn Gly Val Asp Leu Ser Val Val Val Glu Lys Gln Glu Gly Met
                85                  90                  95

Tyr Lys Ser Ala Pro Lys Arg Leu Thr Ala Thr Thr Glu Lys Leu Glu
            100                 105                 110

Ile Gly Trp Lys Ala Trp Gly Lys Ser Ile Leu Phe Ala Pro Glu Leu
        115                 120                 125

Ala Asn Asn Thr Phe Val Val Asp Gly Pro Glu Thr Lys Glu Cys Pro
    130                 135                 140

Thr Gln Asn Arg Ala Trp Asn Ser Leu Glu Val Glu Asp Phe Gly Phe
145                 150                 155                 160

Gly Leu Thr Ser Thr Arg Met Phe Leu Lys Val Arg Glu Ser Asn Thr
                165                 170                 175

Thr Glu Cys Asp Ser Lys Ile Ile Gly Thr Ala Val Lys Asn Asn Leu

```
            180                 185                 190
Ala Ile His Ser Asp Leu Ser Tyr Trp Ile Glu Ser Arg Leu Asn Asp
            195                 200                 205

Thr Trp Lys Leu Glu Arg Ala Val Leu Gly Glu Val Lys Ser Cys Thr
210                 215                 220

Trp Pro Glu Thr His Thr Leu Trp Gly Asp Gly Ile Leu Glu Ser Asp
225                 230                 235                 240

Leu Ile Ile Pro Val Thr Leu Ala Gly Pro Arg Ser Asn His Asn Arg
                245                 250                 255

Arg Pro Gly Tyr Lys Thr Gln Asn Gln Gly Pro Trp Asp Glu Gly Arg
            260                 265                 270

Val Glu Ile Asp Phe Asp Tyr Cys Pro Gly Thr Thr Val Thr Leu Ser
            275                 280                 285

Glu Ser Cys Gly His Arg Gly Pro Ala Thr Arg Thr Thr Thr Glu Ser
            290                 295                 300

Gly Lys Leu Ile Thr Asp Trp Cys Cys Arg Ser Cys Thr Leu Pro Pro
305                 310                 315                 320

Leu Arg Tyr Gln Thr Asp Ser Gly Cys Trp Tyr Gly Met Glu Ile Arg
                325                 330                 335

Pro Gln Arg His Asp Glu Lys Thr Leu Val Gln Ser Gln Val Asn Ala
            340                 345                 350

<210> SEQ ID NO 82
<211> LENGTH: 352
<212> TYPE: PRT
<213> ORGANISM: Dengue virus type 2

<400> SEQUENCE: 82

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Ser Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205
```

```
Thr Trp Lys Ile Glu Lys Ala Ser Phe Ile Glu Val Lys Asn Cys His
        210                 215                 220
Trp Pro Lys Ser His Thr Leu Trp Ser Asn Gly Val Leu Glu Ser Glu
225                 230                 235                 240
Met Ile Ile Pro Lys Asn Leu Ala Gly Pro Val Ser Gln His Asn Tyr
                245                 250                 255
Arg Pro Gly Tyr His Thr Gln Ile Thr Gly Pro Trp His Leu Gly Lys
                260                 265                 270
Leu Glu Met Asp Phe Asp Phe Cys Asp Gly Thr Thr Val Val Val Thr
                275                 280                 285
Glu Asp Cys Gly Asn Arg Gly Pro Ser Leu Arg Thr Thr Thr Ala Ser
290                 295                 300
Gly Lys Leu Ile Thr Glu Trp Cys Cys Arg Ser Cys Thr Leu Pro Pro
305                 310                 315                 320
Leu Arg Tyr Arg Gly Glu Asp Gly Cys Trp Tyr Gly Met Glu Ile Arg
                325                 330                 335
Pro Leu Lys Glu Lys Glu Glu Asn Leu Val Asn Ser Leu Val Thr Ala
                340                 345                 350
```

<210> SEQ ID NO 83
<211> LENGTH: 72
<212> TYPE: PRT
<213> ORGANISM: West Nile virus

<400> SEQUENCE: 83

```
Asp Thr Gly Cys Ala Ile Asp Ile Ser Arg Gln Glu Leu Arg Cys Gly
1               5                   10                  15
Ser Gly Val Phe Ile His Asn Asp Val Glu Ala Trp Met Asp Arg Tyr
                20                  25                  30
Lys Tyr Tyr Pro Glu Thr Pro Gln Gly Leu Ala Lys Ile Ile Gln Lys
                35                  40                  45
Ala His Lys Glu Gly Val Cys Gly Leu Arg Ser Val Ser Arg Leu Glu
            50                  55                  60
His Gln Met Trp Glu Ala Val Lys
65                  70
```

<210> SEQ ID NO 84
<211> LENGTH: 72
<212> TYPE: PRT
<213> ORGANISM: Dengue virus type 1

<400> SEQUENCE: 84

```
Asp Ser Gly Cys Val Ile Asn Trp Lys Gly Arg Glu Leu Lys Cys Gly
1               5                   10                  15
Ser Gly Ile Phe Val Thr Asn Glu Val His Thr Trp Thr Glu Gln Tyr
                20                  25                  30
Lys Phe Gln Ala Asp Ser Pro Lys Arg Leu Ser Ala Ala Ile Gly Lys
                35                  40                  45
Ala Trp Glu Glu Gly Val Cys Gly Ile Arg Ser Ala Thr Arg Leu Glu
            50                  55                  60
Asn Ile Met Trp Lys Gln Ile Ser
65                  70
```

<210> SEQ ID NO 85
<211> LENGTH: 72
<212> TYPE: PRT
<213> ORGANISM: Dengue virus type 2

<400> SEQUENCE: 85

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr
65                  70

<210> SEQ ID NO 86
<211> LENGTH: 72
<212> TYPE: PRT
<213> ORGANISM: Dengue virus type 3

<400> SEQUENCE: 86

Asp Met Gly Cys Val Ile Asn Trp Lys Gly Lys Glu Leu Lys Cys Gly
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ala Thr Ala Ile Ala Gly
        35                  40                  45

Ala Trp Glu Asn Gly Val Cys Gly Ile Arg Ser Thr Thr Arg Met Glu
    50                  55                  60

Asn Leu Leu Trp Lys Gln Ile Ala
65                  70

<210> SEQ ID NO 87
<211> LENGTH: 72
<212> TYPE: PRT
<213> ORGANISM: Dengue virus type 4

<400> SEQUENCE: 87

Asp Met Gly Cys Val Val Ser Trp Ser Gly Lys Glu Leu Lys Cys Gly
1               5                   10                  15

Ser Gly Ile Phe Val Val Asp Asn Val His Thr Trp Thr Glu Gln Tyr
            20                  25                  30

Lys Phe Gln Pro Glu Ser Pro Ala Arg Leu Ala Ser Ala Ile Leu Asn
        35                  40                  45

Ala His Lys Asp Gly Val Cys Gly Ile Arg Ser Thr Thr Arg Leu Glu
    50                  55                  60

Asn Val Met Trp Lys Gln Ile Thr
65                  70

<210> SEQ ID NO 88
<211> LENGTH: 72
<212> TYPE: PRT
<213> ORGANISM: Yellow fever virus

<400> SEQUENCE: 88

Asp Gln Gly Cys Ala Ile Asn Phe Gly Lys Arg Glu Leu Lys Cys Gly
1               5                   10                  15

Asp Gly Val Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
        35                  40                  45

Ser Phe Glu Glu Gly Lys Cys Gly Leu Asn Ser Val Asp Ser Leu Glu
            50                  55                  60

His Glu Met Trp Arg Ser Arg Ala
 65                  70

<210> SEQ ID NO 89
<211> LENGTH: 72
<212> TYPE: PRT
<213> ORGANISM: Japanese encephalitis virus

<400> SEQUENCE: 89

Asp Thr Gly Cys Ala Ile Asp Ile Thr Arg Lys Glu Met Arg Cys Gly
  1               5                  10                  15

Ser Gly Ile Phe Val His Asn Asp Val Glu Ala Trp Val Asp Arg Tyr
             20                  25                  30

Lys Tyr Leu Pro Glu Thr Pro Arg Ser Leu Ala Lys Ile Val His Lys
         35                  40                  45

Ala His Gln Glu Gly Val Cys Gly Val Arg Ser Val Thr Arg Leu Glu
     50                  55                  60

His Gln Met Trp Glu Ser Val Arg
 65                  70

<210> SEQ ID NO 90
<211> LENGTH: 72
<212> TYPE: PRT
<213> ORGANISM: Saint Louis encephalitis virus

<400> SEQUENCE: 90

Asp Ser Gly Cys Ala Ile Asp Leu Gln Arg Arg Glu Leu Lys Cys Gly
  1               5                  10                  15

Gly Gly Ile Phe Val Tyr Asn Asp Val Glu Lys Trp Lys Ser Asp Tyr
             20                  25                  30

Lys Tyr Phe Pro Leu Thr Pro Thr Gly Leu Ala His Val Ile Gln Glu
         35                  40                  45

Ala His Ala Asn Gly Ile Cys Gly Ile Arg Ser Thr Ser Arg Leu Glu
     50                  55                  60

His Leu Met Trp Glu Asn Ile Gln
 65                  70

<210> SEQ ID NO 91
<211> LENGTH: 72
<212> TYPE: PRT
<213> ORGANISM: Murray Valley encephalitis virus

<400> SEQUENCE: 91

Asp Thr Gly Cys Ala Ile Asp Ile Thr Arg Arg Glu Leu Lys Cys Gly
  1               5                  10                  15

Ser Gly Ile Phe Ile His Asn Asp Val Glu Ala Trp Ile Asp Arg Tyr
             20                  25                  30

Lys Tyr Leu Pro Glu Thr Pro Lys Gln Leu Ala Lys Val Val Glu Asn
         35                  40                  45

Ala His Lys Ser Gly Ile Cys Gly Ile Arg Ser Val Asn Arg Phe Glu
     50                  55                  60

His Gln Met Trp Glu Ser Val Arg
 65                  70

<210> SEQ ID NO 92
<211> LENGTH: 72

```
<212> TYPE: PRT
<213> ORGANISM: Tick-borne encephalitis virus

<400> SEQUENCE: 92

Asp Val Gly Cys Ala Val Asp Thr Glu Arg Met Glu Leu Arg Cys Gly
1               5                   10                  15

Glu Gly Leu Val Val Trp Arg Glu Val Ser Glu Trp Tyr Asp Asn Tyr
            20                  25                  30

Ala Tyr Tyr Pro Glu Thr Pro Gly Ala Leu Ala Ser Ala Ile Lys Glu
        35                  40                  45

Thr Phe Glu Glu Gly Ser Cys Gly Val Val Pro Gln Asn Arg Leu Glu
    50                  55                  60

Met Ala Met Trp Arg Ser Ser Val
65                  70

<210> SEQ ID NO 93
<211> LENGTH: 70
<212> TYPE: PRT
<213> ORGANISM: West Nile virus

<400> SEQUENCE: 93

Asp Glu Leu Asn Thr Leu Leu Lys Glu Asn Gly Val Asp Leu Ser Val
1               5                   10                  15

Val Val Glu Lys Gln Glu Gly Met Tyr Lys Ser Ala Pro Lys Arg Leu
            20                  25                  30

Thr Ala Thr Thr Glu Lys Leu Glu Ile Gly Trp Lys Ala Trp Gly Lys
        35                  40                  45

Ser Ile Leu Phe Ala Pro Glu Leu Ala Asn Asn Thr Phe Val Val Asp
    50                  55                  60

Gly Pro Glu Thr Lys Glu
65                  70

<210> SEQ ID NO 94
<211> LENGTH: 70
<212> TYPE: PRT
<213> ORGANISM: Dengue virus type 1

<400> SEQUENCE: 94

Asn Glu Leu Asn His Ile Leu Leu Glu Asn Asp Met Lys Phe Thr Val
1               5                   10                  15

Val Val Gly Asp Val Ser Gly Ile Leu Ala Gln Gly Lys Lys Met Ile
            20                  25                  30

Arg Pro Gln Pro Met Glu His Lys Tyr Ser Trp Lys Ser Trp Gly Lys
        35                  40                  45

Ala Lys Ile Ile Gly Ala Asp Val Gln Asn Thr Thr Phe Ile Ile Asp
    50                  55                  60

Gly Pro Asn Thr Pro Glu
65                  70

<210> SEQ ID NO 95
<211> LENGTH: 70
<212> TYPE: PRT
<213> ORGANISM: Dengue virus type 2

<400> SEQUENCE: 95

Pro Glu Leu Asn His Ile Leu Ser Glu Asn Glu Val Lys Leu Thr Ile
1               5                   10                  15

Met Thr Gly Asp Ile Lys Gly Ile Met Gln Ala Gly Lys Arg Ser Leu
            20                  25                  30
```

```
Arg Pro Gln Pro Thr Glu Leu Lys Tyr Ser Trp Lys Thr Trp Gly Lys
        35                  40                  45

Ala Lys Met Leu Ser Thr Glu Ser His Asn Gln Thr Phe Leu Ile Asp
    50                  55                  60

Gly Pro Glu Thr Ala Glu
65                  70

<210> SEQ ID NO 96
<211> LENGTH: 70
<212> TYPE: PRT
<213> ORGANISM: Dengue virus type 3

<400> SEQUENCE: 96

Asn Glu Leu Asn Tyr Ile Leu Trp Glu Asn Asn Ile Lys Leu Thr Val
1               5                   10                  15

Val Val Gly Asp Ile Thr Gly Val Leu Glu Gln Gly Lys Arg Thr Leu
            20                  25                  30

Thr Pro Gln Pro Met Glu Leu Lys Tyr Ser Trp Lys Thr Trp Gly Lys
        35                  40                  45

Ala Lys Ile Val Thr Ala Glu Thr Gln Asn Ser Ser Phe Ile Ile Asp
    50                  55                  60

Gly Pro Ser Thr Pro Glu
65                  70

<210> SEQ ID NO 97
<211> LENGTH: 70
<212> TYPE: PRT
<213> ORGANISM: Dengue virus type 4

<400> SEQUENCE: 97

Asn Glu Leu Asn Tyr Val Leu Trp Glu Gly Gly His Asp Leu Thr Val
1               5                   10                  15

Val Ala Gly Asp Val Lys Gly Val Leu Thr Lys Gly Lys Arg Ala Leu
            20                  25                  30

Thr Pro Pro Val Ser Asp Leu Lys Tyr Ser Trp Lys Thr Trp Gly Lys
        35                  40                  45

Ala Lys Ile Phe Thr Pro Glu Ala Arg Asn Ser Thr Phe Leu Ile Asp
    50                  55                  60

Gly Pro Asp Thr Ser Glu
65                  70

<210> SEQ ID NO 98
<211> LENGTH: 70
<212> TYPE: PRT
<213> ORGANISM: Yellow fever virus

<400> SEQUENCE: 98

Asp Glu Ile Asn Ala Ile Leu Glu Glu Asn Glu Val Asp Ile Ser Val
1               5                   10                  15

Val Val Gln Asp Pro Lys Asn Ile Tyr Gln Arg Gly Thr His Pro Phe
            20                  25                  30

Ser Arg Ile Arg Asp Gly Leu Gln Tyr Gly Trp Lys Thr Trp Gly Lys
        35                  40                  45

Asn Leu Val Phe Ser Pro Gly Arg Lys Asn Gly Ser Phe Ile Ile Asp
    50                  55                  60

Gly Lys Ser Arg Lys Glu
65                  70
```

<210> SEQ ID NO 99
<211> LENGTH: 70
<212> TYPE: PRT
<213> ORGANISM: Japanese encephalitis virus

<400> SEQUENCE: 99

Asp Glu Leu Asn Val Leu Leu Lys Glu Asn Ala Val Asp Leu Ser Val
1               5                   10                  15

Val Val Asn Lys Pro Val Gly Arg Tyr Arg Ser Ala Pro Lys Arg Leu
            20                  25                  30

Ser Met Thr Gln Glu Lys Phe Glu Met Gly Trp Lys Ala Trp Gly Lys
        35                  40                  45

Ser Leu Leu Phe Ala Pro Glu Leu Ala Asn Ser Ser Phe Val Val Asp
    50                  55                  60

Gly Pro Glu Thr Lys Glu
65                  70

<210> SEQ ID NO 100
<211> LENGTH: 70
<212> TYPE: PRT
<213> ORGANISM: Saint Louis encephalitis virus

<400> SEQUENCE: 100

Arg Glu Leu Asn Ala Ile Phe Glu Asp Asn Glu Ile Asp Leu Ser Val
1               5                   10                  15

Val Val Gln Glu Asp Pro Lys Tyr Tyr Lys Arg Ala Pro Arg Arg Leu
            20                  25                  30

Lys Lys Leu Glu Asp Glu Leu Asp Tyr Gly Trp Lys Lys Trp Gly Lys
        35                  40                  45

Thr Leu Phe Val Glu Pro Arg Leu Gly Asn Asn Thr Phe Val Val Asp
    50                  55                  60

Gly Pro Glu Thr Lys Glu
65                  70

<210> SEQ ID NO 101
<211> LENGTH: 70
<212> TYPE: PRT
<213> ORGANISM: Murray Valley encephalitis virus

<400> SEQUENCE: 101

Asp Glu Leu Asn Ala Leu Leu Lys Glu Asn Ala Ile Asp Leu Ser Val
1               5                   10                  15

Val Val Glu Lys Gln Lys Gly Met Tyr Arg Ala Ala Pro Asn Arg Leu
            20                  25                  30

Arg Leu Thr Val Glu Glu Leu Asp Ile Gly Trp Lys Ala Trp Gly Lys
        35                  40                  45

Ser Leu Leu Phe Ala Ala Glu Leu Ala Asn Ser Thr Phe Val Val Asp
    50                  55                  60

Gly Pro Glu Thr Ala Glu
65                  70

<210> SEQ ID NO 102
<211> LENGTH: 71
<212> TYPE: PRT
<213> ORGANISM: Tick-borne encephalitis virus

<400> SEQUENCE: 102

Thr Glu Leu Asn Leu Ala Leu Ala Glu Gly Glu Ala Asn Leu Thr Val
1               5                   10                  15

```
Val Val Asp Lys Phe Asp Pro Thr Asp Tyr Arg Gly Gly Val Pro Gly
         20                  25                  30

Leu Leu Lys Lys Gly Lys Asp Ile Lys Val Ser Trp Lys Ser Trp Gly
         35                  40                  45

His Ser Met Ile Trp Ser Ile Pro Glu Ala Pro Arg Arg Phe Met Val
     50                  55                  60

Gly Thr Glu Gly Gln Ser Glu
65                  70

<210> SEQ ID NO 103
<211> LENGTH: 71
<212> TYPE: PRT
<213> ORGANISM: West Nile virus

<400> SEQUENCE: 103

Cys Pro Thr Gln Asn Arg Ala Trp Asn Ser Leu Glu Val Glu Asp Phe
1               5                   10                  15

Gly Phe Gly Leu Thr Ser Thr Arg Met Phe Leu Lys Val Arg Glu Ser
             20                  25                  30

Asn Thr Thr Glu Cys Asp Ser Lys Ile Ile Gly Thr Ala Val Lys Asn
         35                  40                  45

Asn Leu Ala Ile His Ser Asp Leu Ser Tyr Trp Ile Glu Ser Arg Leu
     50                  55                  60

Asn Asp Thr Trp Lys Leu Glu
65                  70

<210> SEQ ID NO 104
<211> LENGTH: 71
<212> TYPE: PRT
<213> ORGANISM: Dengue virus type 1

<400> SEQUENCE: 104

Cys Pro Asp Asn Gln Arg Ala Trp Asn Ile Trp Glu Val Glu Asp Tyr
1               5                   10                  15

Gly Phe Gly Ile Phe Thr Thr Asn Ile Trp Leu Lys Leu Arg Asp Ser
             20                  25                  30

Tyr Thr Gln Val Cys Asp His Arg Leu Met Ser Ala Ala Ile Lys Asp
         35                  40                  45

Ser Lys Ala Val His Ala Asp Met Gly Tyr Trp Ile Glu Ser Glu Lys
     50                  55                  60

Asn Glu Thr Trp Lys Leu Ala
65                  70

<210> SEQ ID NO 105
<211> LENGTH: 71
<212> TYPE: PRT
<213> ORGANISM: Dengue virus type 2

<400> SEQUENCE: 105

Cys Pro Asn Thr Asn Arg Ala Trp Asn Ser Leu Glu Val Glu Asp Tyr
1               5                   10                  15

Gly Phe Gly Val Phe Thr Thr Asn Ile Trp Leu Lys Leu Arg Glu Lys
             20                  25                  30

Gln Asp Val Phe Cys Asp Ser Lys Leu Met Ser Ala Ala Ile Lys Asp
         35                  40                  45

Asn Arg Ala Val His Ala Asp Met Gly Tyr Trp Ile Glu Ser Ala Leu
     50                  55                  60
```

```
Asn Asp Thr Trp Lys Met Glu
 65                  70

<210> SEQ ID NO 106
<211> LENGTH: 71
<212> TYPE: PRT
<213> ORGANISM: Dengue virus type 3

<400> SEQUENCE: 106

Cys Pro Ser Ala Ser Arg Ala Trp Asn Val Trp Glu Val Glu Asp Tyr
 1               5                  10                  15

Gly Phe Gly Val Phe Thr Thr Asn Ile Trp Leu Lys Leu Arg Glu Val
             20                  25                  30

Tyr Thr Gln Leu Cys Asp His Arg Leu Met Ser Ala Ala Val Lys Asp
         35                  40                  45

Glu Arg Ala Val His Ala Asp Met Gly Tyr Trp Ile Glu Ser Gln Lys
     50                  55                  60

Asn Gly Ser Trp Lys Leu Glu
 65                  70

<210> SEQ ID NO 107
<211> LENGTH: 71
<212> TYPE: PRT
<213> ORGANISM: Dengue virus type 4

<400> SEQUENCE: 107

Cys Pro Asn Glu Arg Arg Ala Trp Asn Ser Leu Glu Val Glu Asp Tyr
 1               5                  10                  15

Gly Phe Gly Met Phe Thr Thr Asn Ile Trp Met Lys Phe Arg Glu Gly
             20                  25                  30

Ser Ser Glu Val Cys Asp His Arg Leu Met Ser Ala Ala Ile Lys Asp
         35                  40                  45

Gln Lys Ala Val His Ala Asp Met Gly Tyr Trp Ile Glu Ser Ser Lys
     50                  55                  60

Asn Gln Thr Trp Gln Ile Glu
 65                  70

<210> SEQ ID NO 108
<211> LENGTH: 72
<212> TYPE: PRT
<213> ORGANISM: Yellow fever virus

<400> SEQUENCE: 108

Cys Pro Phe Ser Asn Arg Val Trp Asn Ser Leu Gln Ile Glu Glu Phe
 1               5                  10                  15

Gly Thr Gly Val Phe Thr Thr Arg Val Tyr Met Asp Ala Val Phe Glu
             20                  25                  30

Tyr Thr Met Asp Cys Asp Gly Ser Ile Leu Gly Ala Ala Val Asn Gly
         35                  40                  45

Lys Lys Ser Ala His Gly Ser Pro Thr Phe Trp Met Gly Ser His Glu
     50                  55                  60

Val Asn Gly Thr Trp Met Ile His
 65                  70

<210> SEQ ID NO 109
<211> LENGTH: 71
<212> TYPE: PRT
<213> ORGANISM: Japanese encephalitis virus

<400> SEQUENCE: 109
```

Cys Pro Asp Glu Arg Arg Ala Trp Asn Ser Met Gln Ile Glu Asp Phe
1               5                   10                  15

Gly Phe Gly Ile Thr Ser Thr Arg Val Trp Leu Lys Ile Arg Glu Glu
                20                  25                  30

Asn Thr Asp Glu Cys Asp Gly Ala Ile Ile Gly Thr Ala Val Lys Gly
            35                  40                  45

His Val Ala Leu His Ser Asp Leu Ser Tyr Trp Ile Glu Ser Arg Leu
        50                  55                  60

Asn Asp Thr Trp Lys Leu Glu
65              70

<210> SEQ ID NO 110
<211> LENGTH: 71
<212> TYPE: PRT
<213> ORGANISM: Saint Louis encephalitis virus

<400> SEQUENCE: 110

Cys Pro Thr Ala Asn Arg Ala Trp Asn Ser Phe Lys Val Glu Asp Phe
1               5                   10                  15

Gly Phe Gly Met Val Phe Thr Arg Leu Trp Leu Thr Ile Arg Glu Glu
                20                  25                  30

Asn Thr Thr Glu Cys Asp Ser Ala Ile Ile Gly Thr Ala Ile Lys Gly
            35                  40                  45

Asp Arg Ala Val His Ser Asp Leu Ser Tyr Trp Ile Glu Ser Lys Lys
        50                  55                  60

Asn Glu Thr Trp Gln Leu Glu
65              70

<210> SEQ ID NO 111
<211> LENGTH: 71
<212> TYPE: PRT
<213> ORGANISM: Murray Valley encephalitis virus

<400> SEQUENCE: 111

Cys Pro Asn Ser Lys Arg Ala Trp Asn Ser Phe Glu Ile Glu Asp Phe
1               5                   10                  15

Gly Phe Gly Ile Thr Ser Thr Arg Gly Trp Leu Lys Leu Arg Glu Glu
                20                  25                  30

Asn Thr Ser Glu Cys Asp Ser Thr Ile Ile Gly Thr Ala Val Lys Gly
            35                  40                  45

Asn His Ala Val His Ser Asp Leu Ser Tyr Trp Ile Glu Ser Gly Leu
        50                  55                  60

Asn Gly Thr Trp Lys Leu Glu
65              70

<210> SEQ ID NO 112
<211> LENGTH: 70
<212> TYPE: PRT
<213> ORGANISM: Tick-borne encephalitis virus

<400> SEQUENCE: 112

Cys Pro Leu Glu Arg Arg Lys Thr Gly Val Phe Thr Val Ala Glu Phe
1               5                   10                  15

Gly Val Gly Leu Arg Thr Lys Val Phe Leu Asp Phe Arg Gln Glu Pro
                20                  25                  30

Thr His Glu Cys Asp Thr Gly Val Met Gly Ala Ala Val Lys Asn Gly
            35                  40                  45

Met Ala Ile His Thr Asp Gln Ser Leu Trp Met Arg Ser Met Lys Asn
50                  55                  60

Asp Thr Gly Thr Tyr Ile
65                  70

<210> SEQ ID NO 113
<211> LENGTH: 71
<212> TYPE: PRT
<213> ORGANISM: West Nile virus

<400> SEQUENCE: 113

Arg Ala Val Leu Gly Glu Val Lys Ser Cys Thr Trp Pro Glu Thr His
1               5                   10                  15

Thr Leu Trp Gly Asp Gly Ile Leu Glu Ser Asp Leu Ile Ile Pro Val
            20                  25                  30

Thr Leu Ala Gly Pro Arg Ser Asn His Asn Arg Arg Pro Gly Tyr Lys
        35                  40                  45

Thr Gln Asn Gln Gly Pro Trp Asp Glu Gly Arg Val Glu Ile Asp Phe
    50                  55                  60

Asp Tyr Cys Pro Gly Thr Thr
65                  70

<210> SEQ ID NO 114
<211> LENGTH: 71
<212> TYPE: PRT
<213> ORGANISM: Dengue virus type 1

<400> SEQUENCE: 114

Arg Ala Ser Phe Ile Glu Val Lys Thr Cys Ile Trp Pro Lys Ser His
1               5                   10                  15

Thr Leu Trp Ser Asn Gly Val Leu Glu Ser Glu Met Ile Ile Pro Lys
            20                  25                  30

Ile Tyr Gly Gly Pro Ile Ser Gln His Asn Tyr Arg Pro Gly Tyr Phe
        35                  40                  45

Thr Gln Thr Ala Gly Pro Trp His Leu Gly Lys Leu Glu Leu Asp Phe
    50                  55                  60

Asp Phe Cys Glu Gly Thr Thr
65                  70

<210> SEQ ID NO 115
<211> LENGTH: 71
<212> TYPE: PRT
<213> ORGANISM: Dengue virus type 2

<400> SEQUENCE: 115

Lys Ala Ser Phe Ile Glu Val Lys Ser Cys His Trp Pro Lys Ser His
1               5                   10                  15

Thr Leu Trp Ser Asn Gly Val Leu Glu Ser Glu Met Ile Ile Pro Lys
            20                  25                  30

Ser Phe Ala Gly Pro Val Ser Gln His Asn Tyr Arg Pro Gly Tyr Tyr
        35                  40                  45

Thr Gln Thr Ala Gly Pro Trp His Leu Gly Lys Leu Glu Met Asp Phe
    50                  55                  60

Asp Phe Cys Glu Gly Thr Thr
65                  70

<210> SEQ ID NO 116
<211> LENGTH: 71
<212> TYPE: PRT

<213> ORGANISM: Dengue virus type 3

<400> SEQUENCE: 116

Lys Ala Ser Leu Ile Glu Val Lys Thr Cys Th

Thr Ile Ala Gly Pro Arg Ser Lys His Asn Arg Arg Glu Gly Tyr Lys
            35                  40                  45

Thr Gln Asn Gln Gly Pro Trp Asp Glu Asn Gly Leu Val Pro Gly Leu
        50                  55                  60

Asp Tyr Cys Pro Gly Thr Lys
65                  70

<210> SEQ ID NO 120
<211> LENGTH: 71
<212> TYPE: PRT
<213> ORGANISM: Saint Louis encephalitis virus

<400> SEQUENCE: 120

Arg Ala Val Met Gly Glu Val Lys Ser Cys Thr Trp Pro Glu Thr His
1               5                   10                  15

Thr Leu Trp Gly Asp Gly Val Val Glu Ser Glu Met Ile Ile Pro Val
            20                  25                  30

Thr Leu Gly Gly Pro Lys Ser His His Asn Lys Arg Asn Gly Tyr His
            35                  40                  45

Thr Gln Thr Lys Gly Pro Trp Ser Glu Gly Glu Ile Thr Leu Asp Phe
        50                  55                  60

Asp Tyr Cys Pro Gly Thr Thr
65                  70

<210> SEQ ID NO 121
<211> LENGTH: 71
<212> TYPE: PRT
<213> ORGANISM: Murray Valley encephalitis virus

<400> SEQUENCE: 121

Arg Ala Ile Phe Gly Glu Val Lys Ser Cys Thr Trp Pro Glu Thr His
1               5                   10                  15

Thr Leu Trp Gly Asp Ala Val Glu Gly Thr Glu Leu Ile Ile Pro Val
            20                  25                  30

Thr Leu Ala Gly Pro Arg Ser Lys His Asn Arg Arg Glu Gly Tyr Lys
            35                  40                  45

Val Gln Val Gln Gly Pro Trp Asp Glu Glu Asp Ile Lys Leu Asp Phe
        50                  55                  60

Asp Tyr Cys Pro Gly Thr Thr
65                  70

<210> SEQ ID NO 122
<211> LENGTH: 72
<212> TYPE: PRT
<213> ORGANISM: Tick-borne encephalitis virus

<400> SEQUENCE: 122

Val Glu Leu Leu Val Thr Asp Leu Arg Asn Cys Ser Trp Pro Ala Ser
1               5                   10                  15

His Thr Ile Asp Asn Ala Asp Val Val Asp Ser Glu Leu Phe Leu Pro
            20                  25                  30

Ala Ser Leu Ala Gly Pro Arg Ser Trp Tyr Asn Arg Ile Pro Gly Tyr
            35                  40                  45

Ser Glu Gln Val Lys Gly Pro Trp Lys Tyr Thr Pro Ile Arg Val Ile
        50                  55                  60

Arg Glu Glu Cys Pro Gly Thr Thr
65                  70

```
<210> SEQ ID NO 123
<211> LENGTH: 68
<212> TYPE: PRT
<213> ORGANISM: West Nile virus

<400> SEQUENCE: 123

Val Thr Leu Ser Glu Ser Cys Gly His Arg Gly Pro Ala Thr Arg Thr
1               5                   10                  15

Thr Thr Glu Ser Gly Lys Leu Ile Thr Asp Trp Cys Cys Arg Ser Cys
            20                  25                  30

Thr Leu Pro Pro Leu Arg Tyr Gln Thr Asp Ser Gly Cys Trp Tyr Gly
        35                  40                  45

Met Glu Ile Arg Pro Gln Arg His Asp Glu Lys Thr Leu Val Gln Ser
    50                  55                  60

Gln Val Asn Ala
65

<210> SEQ ID NO 124
<211> LENGTH: 68
<212> TYPE: PRT
<213> ORGANISM: Dengue virus type 1

<400> SEQUENCE: 124

Val Val Val Asp Glu His Cys Gly Asn Arg Gly Pro Ser Leu Arg Thr
1               5                   10                  15

Thr Thr Val Thr Gly Lys Ile Ile His Glu Trp Cys Cys Arg Ser Cys
            20                  25                  30

Thr Leu Pro Pro Leu Arg Phe Lys Gly Glu Asp Gly Cys Trp Tyr Gly
        35                  40                  45

Met Glu Ile Arg Pro Val Lys Asp Lys Glu Glu Asn Leu Val Lys Ser
    50                  55                  60

Met Val Ser Ala
65

<210> SEQ ID NO 125
<211> LENGTH: 68
<212> TYPE: PRT
<213> ORGANISM: Dengue virus type 2

<400> SEQUENCE: 125

Val Val Val Thr Glu Asp Cys Gly Asn Arg Gly Pro Ser Leu Arg Thr
1               5                   10                  15

Thr Thr Ala Ser Gly Lys Leu Ile Thr Glu Trp Cys Cys Arg Ser Cys
            20                  25                  30

Thr Leu Pro Pro Leu Arg Tyr Arg Gly Glu Asp Gly Cys Trp Tyr Gly
        35                  40                  45

Met Glu Ile Arg Pro Leu Lys Glu Lys Glu Glu Asn Leu Val Asn Ser
    50                  55                  60

Leu Val Thr Ala
65

<210> SEQ ID NO 126
<211> LENGTH: 68
<212> TYPE: PRT
<213> ORGANISM: Dengue virus type 3

<400> SEQUENCE: 126

Val Val Ile Ser Glu Asn Cys Gly Thr Arg Gly Pro Ser Leu Arg Thr
1               5                   10                  15
```

Thr Thr Val Ser Gly Lys Leu Ile His Glu Trp Cys Cys Arg Ser Cys
            20                  25                  30

Thr Leu Pro Pro Leu Arg Tyr Met Gly Glu Asp Gly Cys Trp Tyr Gly
            35                  40                  45

Met Glu Ile Arg Pro Ile Asn Glu Lys Glu Glu Asn Met Val Lys Ser
        50                  55                  60

Leu Ala Ser Ala
65

<210> SEQ ID NO 127
<211> LENGTH: 68
<212> TYPE: PRT
<213> ORGANISM: Dengue virus type 4

<400> SEQUENCE: 127

Val Thr Ile Gln Glu Asp Cys Asp His Arg Gly Pro Ser Leu Arg Thr
1               5                   10                  15

Thr Thr Ala Ser Gly Lys Leu Val Thr Gln Trp Cys Cys Arg Ser Cys
            20                  25                  30

Thr Met Pro Pro Leu Arg Phe Leu Gly Glu Asp Gly Cys Trp Tyr Gly
            35                  40                  45

Met Glu Ile Arg Pro Leu Ser Glu Lys Glu Glu Asn Met Val Lys Ser
        50                  55                  60

Gln Val Thr Ala
65

<210> SEQ ID NO 128
<211> LENGTH: 68
<212> TYPE: PRT
<213> ORGANISM: Yellow fever virus

<400> SEQUENCE: 128

Val Val Val Asp Gly Gly Cys Asp Gly Arg Gly Lys Ser Thr Arg Ser
1               5                   10                  15

Thr Thr Asp Ser Gly Lys Ile Ile Pro Glu Trp Cys Cys Arg Ser Cys
            20                  25                  30

Thr Met Pro Pro Val Ser Phe His Gly Ser Asp Gly Cys Trp Tyr Pro
            35                  40                  45

Met Glu Ile Arg Pro Arg Lys Thr His Asp Asn His Leu Val Arg Ser
        50                  55                  60

Trp Val Thr Ala
65

<210> SEQ ID NO 129
<211> LENGTH: 68
<212> TYPE: PRT
<213> ORGANISM: Japanese encephalitis virus

<400> SEQUENCE: 129

Val Thr Ile Thr Glu Asp Cys Gly Lys Arg Gly Pro Ser Ile Arg Thr
1               5                   10                  15

Thr Thr Asp Ser Gly Lys Leu Ile Thr Asp Trp Cys Cys Arg Ser Cys
            20                  25                  30

Ser Leu Pro Pro Leu Arg Phe Arg Thr Glu Asn Gly Cys Trp Tyr Gly
            35                  40                  45

Met Glu Ile Arg Pro Val Arg His Asp Glu Thr Thr Leu Val Arg Ser
        50                  55                  60

Gln Val Asp Ala

<210> SEQ ID NO 130
<211> LENGTH: 68
<212> TYPE: PRT
<213> ORGANISM: Saint Louis encephalitis virus

<400> SEQUENCE: 130

Val Thr Val Thr Glu His Cys Gly Asn Arg Gly Ala Ser Leu Arg Thr
1               5                   10                  15

Thr Thr Ala Ser Gly Lys Leu Val Thr Asp Trp Cys Cys Arg Ser Cys
            20                  25                  30

Ser Leu Pro Pro Leu Arg Tyr Thr Thr Lys Asp Gly Cys Trp Tyr Gly
        35                  40                  45

Met Glu Ile Arg Pro Val Lys Glu Glu Glu Ala Lys Leu Val Lys Ser
    50                  55                  60

Arg Val Thr Ala
65

<210> SEQ ID NO 131
<211> LENGTH: 68
<212> TYPE: PRT
<213> ORGANISM: Murray Valley encephalitis virus

<400> SEQUENCE: 131

Val Thr Val Ser Glu His Cys Gly Lys Arg Gly Pro Ser Val Arg Thr
1               5                   10                  15

Thr Thr Asp Ser Gly Lys Leu Val Thr Asp Trp Cys Cys Arg Ser Cys
            20                  25                  30

Thr Leu Pro Pro Leu Arg Phe Thr Thr Ala Ser Gly Cys Trp Tyr Gly
        35                  40                  45

Met Glu Ile Arg Pro Met Lys His Asp Glu Ser Thr Leu Val Lys Ser
    50                  55                  60

Arg Val Gln Ala
65

<210> SEQ ID NO 132
<211> LENGTH: 67
<212> TYPE: PRT
<213> ORGANISM: Tick-borne encephalitis virus

<400> SEQUENCE: 132

Val Thr Ile Asn Ala Lys Cys Asp Lys Arg Gly Ala Ser Val Arg Ser
1               5                   10                  15

Thr Thr Glu Ser Gly Lys Val Ile Pro Glu Trp Cys Cys Arg Ala Cys
            20                  25                  30

Thr Met Pro Pro Val Thr Phe Arg Thr Gly Thr Asp Cys Trp Tyr Ala
        35                  40                  45

Met Glu Ile Arg Pro Val His Asp Gln Gly Gly Leu Val Arg Ser Met
    50                  55                  60

Val Val Ala
65

<210> SEQ ID NO 133
<211> LENGTH: 352
<212> TYPE: PRT
<213> ORGANISM: West Nile virus

<400> SEQUENCE: 133

Asp Thr Gly Cys Ala Ile Asp Ile Ser Arg Gln Glu Leu Arg Cys Gly
1               5                   10                  15

Ser Gly Val Phe Ile His Asn Asp Val Glu Ala Trp Met Asp Arg Tyr
            20                  25                  30

Lys Tyr Tyr Pro Glu Thr Pro Gln Gly Leu Ala Lys Ile Ile Gln Lys
        35                  40                  45

Ala His Lys Glu Gly Val Cys Gly Leu Arg Ser Val Ser Arg Leu Glu
50                  55                  60

His Gln Met Trp Glu Ala Val Lys Asp Glu Leu Asn Thr Leu Leu Lys
65                  70                  75                  80

Glu Asn Gly Val Asp Leu Ser Val Val Glu Lys Gln Glu Gly Met
            85                  90                  95

Tyr Lys Ser Ala Pro Lys Arg Leu Thr Ala Thr Thr Glu Lys Leu Glu
            100                 105                 110

Ile Gly Trp Lys Ala Trp Gly Lys Ser Ile Leu Phe Ala Pro Glu Leu
        115                 120                 125

Ala Asn Asn Thr Phe Val Val Asp Gly Pro Glu Thr Lys Glu Cys Pro
        130                 135                 140

Thr Gln Asn Arg Ala Trp Asn Ser Leu Glu Val Glu Asp Phe Gly Phe
145                 150                 155                 160

Gly Leu Thr Ser Thr Arg Met Phe Leu Lys Val Arg Glu Ser Asn Thr
            165                 170                 175

Thr Glu Cys Asp Ser Lys Ile Ile Gly Thr Ala Val Lys Asn Asn Leu
            180                 185                 190

Ala Ile His Ser Asp Leu Ser Tyr Trp Ile Glu Ser Arg Leu Asn Asp
        195                 200                 205

Thr Trp Lys Leu Glu Arg Ala Val Leu Gly Glu Val Lys Ser Cys Thr
210                 215                 220

Trp Pro Glu Thr His Thr Leu Trp Gly Asp Gly Ile Leu Glu Ser Asp
225                 230                 235                 240

Leu Ile Ile Pro Val Thr Leu Ala Gly Pro Arg Ser Asn His Asn Arg
            245                 250                 255

Arg Pro Gly Tyr Lys Thr Gln Asn Gln Gly Pro Trp Asp Glu Gly Arg
            260                 265                 270

Val Glu Ile Asp Phe Asp Tyr Cys Pro Gly Thr Thr Val Thr Leu Ser
        275                 280                 285

Glu Ser Cys Gly His Arg Gly Pro Ala Thr Arg Thr Thr Thr Glu Ser
        290                 295                 300

Gly Lys Leu Ile Thr Asp Trp Cys Cys Arg Ser Cys Thr Leu Pro Pro
305                 310                 315                 320

Leu Arg Tyr Gln Thr Asp Ser Gly Cys Trp Tyr Gly Met Glu Ile Arg
            325                 330                 335

Pro Gln Arg His Asp Glu Lys Thr Leu Val Gln Ser Gln Val Asn Ala
            340                 345                 350

<210> SEQ ID NO 134
<211> LENGTH: 352
<212> TYPE: PRT
<213> ORGANISM: Dengue virus type 1

<400> SEQUENCE: 134

Asp Ser Gly Cys Val Ile Asn Trp Lys Gly Arg Glu Leu Lys Cys Gly
1               5                   10                  15

Ser Gly Ile Phe Val Thr Asn Glu Val His Thr Trp Thr Glu Gln Tyr
            20                  25                  30

```
Lys Phe Gln Ala Asp Ser Pro Lys Arg Leu Ser Ala Ile Gly Lys
        35                  40                  45

Ala Trp Glu Glu Gly Val Cys Gly Ile Arg Ser Ala Thr Arg Leu Glu
 50                  55                  60

Asn Ile Met Trp Lys Gln Ile Ser Asn Glu Leu Asn His Ile Leu Leu
 65                  70                  75                  80

Glu Asn Asp Met Lys Phe Thr Val Val Gly Asp Val Ser Gly Ile
                85                  90                  95

Leu Ala Gln Gly Lys Lys Met Ile Arg Pro Gln Pro Met Glu His Lys
                100                 105                 110

Tyr Ser Trp Lys Ser Trp Gly Lys Ala Lys Ile Ile Gly Ala Asp Val
                115                 120                 125

Gln Asn Thr Thr Phe Ile Ile Asp Gly Pro Asn Thr Pro Glu Cys Pro
    130                 135                 140

Asp Asn Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Val Cys Asp His Arg Leu Met Ser Ala Ala Ile Lys Asp Ser Lys
                180                 185                 190

Ala Val His Ala Asp Met Gly Tyr Trp Ile Glu Ser Glu Lys Asn Glu
                195                 200                 205

Thr Trp Lys Leu Ala Arg Ala Ser Phe Ile Glu Val Lys Thr Cys Ile
                210                 215                 220

Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
                245                 250                 255

Arg Pro Gly Tyr Phe Thr Gln Thr Ala Gly Pro Trp His Leu Gly Lys
                260                 265                 270

Leu Glu Leu Asp Phe Asp Phe Cys Glu Gly Thr Thr Val Val Val Asp
                275                 280                 285

Glu His Cys Gly Asn Arg Gly Pro Ser Leu Arg Thr Thr Thr Val Thr
                290                 295                 300

Gly Lys Ile Ile His Glu Trp Cys Cys Arg Ser Cys Thr Leu Pro Pro
305                 310                 315                 320

Leu Arg Phe Lys Gly Glu Asp Gly Cys Trp Tyr Gly Met Glu Ile Arg
                325                 330                 335

Pro Val Lys Asp Lys Glu Glu Asn Leu Val Lys Ser Met Val Ser Ala
                340                 345                 350

<210> SEQ ID NO 135
<211> LENGTH: 352
<212> TYPE: PRT
<213> ORGANISM: Dengue virus type 2

<400> SEQUENCE: 135

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
                20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
```

```
            50                  55                  60
Asn Leu Met Trp Lys Gln Ile Thr Pro Glu Leu Asn His Ile Leu Ser
 65                  70                  75                  80

Glu Asn Glu Val Lys Leu Thr Ile Met Thr Gly Asp Ile Lys Gly Ile
                     85                  90                  95

Met Gln Ala Gly Lys Arg Ser Leu Arg Pro Gln Pro Thr Glu Leu Lys
                100                 105                 110

Tyr Ser Trp Lys Thr Trp Gly Lys Ala Lys Met Leu Ser Thr Glu Ser
            115                 120                 125

His Asn Gln Thr Phe Leu Ile Asp Gly Pro Glu Thr Ala Glu Cys Pro
        130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                    165                 170                 175

Val Phe Cys Asp Ser Lys Leu Met Ser Ala Ala Ile Lys Asp Asn Arg
                180                 185                 190

Ala Val His Ala Asp Met Gly Tyr Trp Ile Glu Ser Ala Leu Asn Asp
            195                 200                 205

Thr Trp Lys Ile Glu Lys Ala Ser Phe Ile Glu Val Lys Asn Cys His
        210                 215                 220

Trp Pro Lys Ser His Thr Leu Trp Ser Asn Gly Val Leu Glu Ser Glu
225                 230                 235                 240

Met Ile Ile Pro Lys Asn Leu Ala Gly Pro Val Ser Gln His Asn Tyr
                    245                 250                 255

Arg Pro Gly Tyr His Thr Gln Ile Thr Gly Pro Trp His Leu Gly Lys
                260                 265                 270

Leu Glu Met Asp Phe Asp Phe Cys Asp Gly Thr Thr Val Val Val Thr
            275                 280                 285

Glu Asp Cys Gly Asn Arg Gly Pro Ser Leu Arg Thr Thr Thr Ala Ser
        290                 295                 300

Gly Lys Leu Ile Thr Glu Trp Cys Cys Arg Ser Cys Thr Leu Pro Pro
305                 310                 315                 320

Leu Arg Tyr Arg Gly Glu Asp Gly Cys Trp Tyr Gly Met Glu Ile Arg
                    325                 330                 335

Pro Leu Lys Glu Lys Glu Asn Leu Val Asn Ser Leu Val Thr Ala
                340                 345                 350

<210> SEQ ID NO 136
<211> LENGTH: 352
<212> TYPE: PRT
<213> ORGANISM: Dengue virus type 3

<400> SEQUENCE: 136

Asp Met Gly Cys Val Ile Asn Trp Lys Gly Lys Glu Leu Lys Cys Gly
 1                   5                  10                  15

Ser Gly Ile Phe Val Thr Asn Glu Val His Thr Trp Thr Glu Gln Tyr
                 20                  25                  30

Lys Phe Gln Ala Asp Ser Pro Lys Arg Leu Ala Thr Ala Ile Ala Gly
             35                  40                  45

Ala Trp Glu Asn Gly Val Cys Gly Ile Arg Ser Thr Thr Arg Met Glu
         50                  55                  60

Asn Leu Leu Trp Lys Gln Ile Ala Asn Glu Leu Asn Tyr Ile Leu Trp
 65                  70                  75                  80
```

```
Glu Asn Asn Ile Lys Leu Thr Val Val Gly Asp Ile Thr Gly Val
                    85                  90                  95

Leu Glu Gln Gly Lys Arg Thr Leu Thr Pro Gln Pro Met Glu Leu Lys
                100                 105                 110

Tyr Ser Trp Lys Thr Trp Gly Lys Ala Lys Ile Val Thr Ala Glu Thr
            115                 120                 125

Gln Asn Ser Ser Phe Ile Ile Asp Gly Pro Ser Thr Pro Glu Cys Pro
    130                 135                 140

Ser Ala Ser Arg Ala Trp Asn Val Trp Glu Val Glu Asp Tyr Gly Phe
145                 150                 155                 160

Gly Val Phe Thr Thr Asn Ile Trp Leu Lys Leu Arg Glu Val Tyr Thr
                165                 170                 175

Gln Leu Cys Asp His Arg Leu Met Ser Ala Ala Val Lys Asp Glu Arg
            180                 185                 190

Ala Val His Ala Asp Met Gly Tyr Trp Ile Glu Ser Gln Lys Asn Gly
        195                 200                 205

Ser Trp Lys Leu Glu Lys Ala Ser Leu Ile Glu Val Lys Thr Cys Thr
    210                 215                 220

Trp Pro Lys Ser His Thr Leu Trp Ser Asn Gly Val Leu Glu Ser Asp
225                 230                 235                 240

Met Ile Ile Pro Lys Ser Leu Ala Gly Pro Ile Ser Gln His Asn His
                245                 250                 255

Arg Pro Gly Tyr His Thr Gln Thr Ala Gly Pro Trp His Leu Gly Lys
            260                 265                 270

Leu Glu Leu Asp Phe Asn Tyr Cys Glu Gly Thr Thr Val Val Ile Ser
        275                 280                 285

Glu Asn Cys Gly Thr Arg Gly Pro Ser Leu Arg Thr Thr Thr Val Ser
    290                 295                 300

Gly Lys Leu Ile His Glu Trp Cys Cys Arg Ser Cys Thr Leu Pro Pro
305                 310                 315                 320

Leu Arg Tyr Met Gly Glu Asp Gly Cys Trp Tyr Gly Met Glu Ile Arg
                325                 330                 335

Pro Ile Asn Glu Lys Glu Glu Asn Met Val Lys Ser Leu Ala Ser Ala
            340                 345                 350

<210> SEQ ID NO 137
<211> LENGTH: 352
<212> TYPE: PRT
<213> ORGANISM: Dengue virus type 4

<400> SEQUENCE: 137

Asp Met Gly Cys Val Val Ser Trp Ser Gly Lys Glu Leu Lys Cys Gly
1               5                   10                  15

Ser Gly Ile Phe Val Val Asp Asn His Thr Trp Thr Glu Gln Tyr
                20                  25                  30

Lys Phe Gln Pro Glu Ser Pro Ala Arg Leu Ala Ser Ala Ile Leu Asn
            35                  40                  45

Ala His Lys Asp Gly Val Cys Gly Ile Arg Ser Thr Thr Arg Leu Glu
        50                  55                  60

Asn Val Met Trp Lys Gln Ile Thr Asn Glu Leu Asn Tyr Val Leu Trp
65                  70                  75                  80

Glu Gly Gly His Asp Leu Thr Val Val Ala Gly Asp Val Lys Gly Val
                85                  90                  95

Leu Thr Lys Gly Lys Arg Ala Leu Thr Pro Pro Val Ser Asp Leu Lys
            100                 105                 110
```

Tyr Ser Trp Lys Thr Trp Gly Lys Ala Lys Ile Phe Thr Pro Glu Ala
            115                 120                 125

Arg Asn Ser Thr Phe Leu Ile Asp Gly Pro Asp Thr Ser Glu Cys Pro
130                 135                 140

Asn Glu Arg Arg Ala Trp Asn Ser Leu Glu Val Glu Asp Tyr Gly Phe
145                 150                 155                 160

Gly Met Phe Thr Thr Asn Ile Trp Met Lys Phe Arg Glu Gly Ser Ser
            165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Ser Lys Asn Gln
            195                 200                 205

Thr Trp Gln Ile Glu Lys Ala Ser Leu Ile Glu Val Lys Thr Cys Leu
            210                 215                 220

Trp Pro Lys Thr His Thr Leu Trp Ser Asn Gly Val Leu Glu Ser Gln
225                 230                 235                 240

Met Leu Ile Pro Lys Ser Tyr Ala Gly Pro Phe Ser Gln His Asn Tyr
            245                 250                 255

Arg Gln Gly Tyr Ala Thr Gln Thr Val Gly Pro Trp His Leu Gly Lys
            260                 265                 270

Leu Glu Ile Asp Phe Gly Glu Cys Pro Gly Thr Thr Val Thr Ile Gln
            275                 280                 285

Glu Asp Cys Asp His Arg Gly Pro Ser Leu Arg Thr Thr Thr Ala Ser
            290                 295                 300

Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
            325                 330                 335

Pro Leu Ser Glu Lys Glu Glu Asn Met Val Lys Ser Gln Val Thr Ala
            340                 345                 350

<210> SEQ ID NO 138
<211> LENGTH: 352
<212> TYPE: PRT
<213> ORGANISM: Yellow fever virus

<400> SEQUENCE: 138

Asp Gln Gly Cys Ala Ile Asn Phe Gly Lys Arg Glu Leu Lys Cys Gly
1               5                   10                  15

Asp Gly Val Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
            35                  40                  45

Ser Phe Glu Glu Gly Lys Cys Gly Leu Asn Ser Val Asp Ser Leu Glu
50                  55                  60

His Glu Met Trp Arg Ser Arg Ala Asp Glu Ile Asn Ala Ile Leu Glu
65                  70                  75                  80

Glu Asn Glu Val Asp Ile Ser Val Val Gln Asp Pro Lys Asn Val
            85                  90                  95

Tyr Gln Arg Gly Thr His Pro Phe Ser Arg Ile Arg Asp Gly Leu Gln
            100                 105                 110

Tyr Gly Trp Lys Thr Trp Gly Lys Asn Leu Val Phe Ser Pro Gly Arg
            115                 120                 125

Lys Asn Gly Ser Phe Ile Ile Asp Gly Lys Ser Arg Lys Glu Cys Pro

```
                130             135             140
Phe Ser Asn Arg Val Trp Asn Ser Leu Gln Ile Glu Glu Phe Gly Thr
145                 150                 155                 160

Gly Val Phe Thr Thr Arg Val Tyr Met Asp Ala Val Phe Glu Tyr Thr
                165                 170                 175

Met Asp Cys Asp Gly Ser Ile Leu Gly Ala Ala Val Asn Gly Lys Lys
            180                 185                 190

Ser Ala His Gly Ser Pro Thr Phe Trp Met Gly Ser His Glu Val Asn
        195                 200                 205

Gly Thr Trp Met Ile His Thr Leu Glu Thr Leu Asp Tyr Lys Glu Cys
    210                 215                 220

Glu Trp Pro Leu Thr His Thr Ile Gly Thr Ser Val Glu Glu Ser Asp
225                 230                 235                 240

Met Phe Met Pro Arg Ser Ile Gly Gly Pro Val Ser Ser His Asn His
                245                 250                 255

Ile Pro Gly Tyr Lys Val Gln Thr Asn Gly Pro Trp Met Gln Val Pro
            260                 265                 270

Leu Glu Val Lys Arg Glu Ala Cys Pro Gly Thr Ser Val Val Val Asp
        275                 280                 285

Gly Gly Cys Asp Gly Arg Gly Lys Ser Thr Arg Ser Thr Thr Asp Ser
    290                 295                 300

Gly Lys Ile Ile Pro Glu Trp Cys Cys Arg Ser Cys Thr Met Pro Pro
305                 310                 315                 320

Val Ser Phe His Gly Ser Asp Gly Cys Trp Tyr Pro Met Glu Ile Arg
                325                 330                 335

Pro Arg Lys Thr His Asp Asn His Leu Val Arg Ser Trp Val Thr Ala
            340                 345                 350

<210> SEQ ID NO 139
<211> LENGTH: 352
<212> TYPE: PRT
<213> ORGANISM: Japanese encephalitis virus

<400> SEQUENCE: 139

Asp Thr Gly Cys Ala Ile Asp Ile Thr Arg Lys Glu Met Arg Cys Gly
1               5                   10                  15

Ser Gly Ile Phe Val His Asn Asp Val Glu Ala Trp Val Asp Arg Tyr
            20                  25                  30

Lys Tyr Leu Pro Glu Thr Pro Arg Ser Leu Ala Lys Ile Val His Lys
        35                  40                  45

Ala His Gln Glu Gly Val Cys Gly Val Arg Ser Val Thr Arg Leu Glu
    50                  55                  60

His Gln Met Trp Glu Ser Val Arg Asp Glu Leu Asn Val Leu Leu Lys
65                  70                  75                  80

Glu Asn Ala Val Asp Leu Ser Val Val Asn Lys Pro Val Gly Arg
                85                  90                  95

Tyr Arg Ser Ala Pro Lys Arg Leu Ser Met Thr Gln Glu Lys Phe Glu
                100                 105                 110

Met Gly Trp Lys Ala Trp Gly Lys Ser Leu Leu Phe Ala Pro Glu Leu
            115                 120                 125

Ala Asn Ser Ser Phe Val Val Asp Gly Pro Glu Thr Lys Glu Cys Pro
        130                 135                 140

Asp Glu Arg Arg Ala Trp Asn Ser Met Gln Ile Glu Asp Phe Gly Phe
145                 150                 155                 160
```

```
Gly Ile Thr Ser Thr Arg Val Trp Leu Lys Ile Arg Glu Glu Asn Thr
                165                 170                 175

Asp Glu Cys Asp Gly Ala Ile Ile Gly Thr Ala Val Lys Gly His Val
            180                 185                 190

Ala Leu His Ser Asp Leu Ser Tyr Trp Ile Glu Ser Arg Leu Asn Asp
        195                 200                 205

Thr Trp Lys Leu Glu Arg Ala Val Phe Gly Glu Val Lys Ser Cys Thr
    210                 215                 220

Trp Pro Glu Thr His Thr Leu Trp Gly Asp Gly Val Glu Glu Ser Glu
225                 230                 235                 240

Leu Ile Ile Pro His Thr Ile Ala Gly Pro Arg Ser Lys His Asn Arg
                245                 250                 255

Arg Glu Gly Tyr Lys Thr Gln Asn Gln Gly Pro Trp Asp Glu Asn Gly
            260                 265                 270

Leu Val Pro Gly Leu Asp Tyr Cys Pro Gly Thr Lys Val Thr Ile Thr
        275                 280                 285

Glu Asp Cys Gly Lys Arg Gly Pro Ser Ile Arg Thr Thr Thr Asp Ser
    290                 295                 300

Gly Lys Leu Ile Thr Asp Trp Cys Cys Arg Ser Cys Ser Leu Pro Pro
305                 310                 315                 320

Leu Arg Phe Arg Thr Glu Asn Gly Cys Trp Tyr Gly Met Glu Ile Arg
                325                 330                 335

Pro Val Arg His Asp Glu Thr Thr Leu Val Arg Ser Gln Val Asp Ala
            340                 345                 350

<210> SEQ ID NO 140
<211> LENGTH: 352
<212> TYPE: PRT
<213> ORGANISM: Saint Louis encephalitis virus

<400> SEQUENCE: 140

Asp Ser Gly Cys Ala Ile Asp Leu Gln Arg Arg Glu Leu Lys Cys Gly
1               5                   10                  15

Gly Gly Ile Phe Val Tyr Asn Asp Val Glu Lys Trp Lys Ser Asp Tyr
            20                  25                  30

Lys Tyr Phe Pro Leu Thr Pro Thr Gly Leu Ala His Val Ile Gln Glu
        35                  40                  45

Ala His Ala Asn Gly Ile Cys Gly Ile Arg Ser Thr Ser Arg Leu Glu
    50                  55                  60

His Leu Met Trp Glu Asn Ile Gln Arg Glu Leu Asn Ala Ile Phe Glu
65                  70                  75                  80

Asp Asn Glu Ile Asp Leu Ser Val Val Val Gln Glu Asp Pro Lys Tyr
                85                  90                  95

Tyr Lys Arg Ala Pro Arg Arg Leu Lys Lys Leu Glu Asp Glu Leu Asp
            100                 105                 110

Tyr Gly Trp Lys Lys Trp Gly Lys Thr Leu Phe Val Glu Pro Arg Leu
        115                 120                 125

Gly Asn Asn Thr Phe Val Val Asp Gly Pro Glu Thr Lys Glu Cys Pro
    130                 135                 140

Thr Ala Asn Arg Ala Trp Asn Ser Phe Lys Val Glu Asp Phe Gly Phe
145                 150                 155                 160

Gly Met Val Phe Thr Arg Leu Trp Leu Thr Ile Arg Glu Glu Asn Thr
                165                 170                 175

Thr Glu Cys Asp Ser Ala Ile Ile Gly Thr Ala Ile Lys Gly Asp Arg
            180                 185                 190
```

```
Ala Val His Ser Asp Leu Ser Tyr Trp Ile Glu Ser Lys Lys Asn Glu
            195                 200                 205

Thr Trp Gln Leu Glu Arg Ala Val Met Gly Glu Val Lys Ser Cys Thr
210                 215                 220

Trp Pro Glu Thr His Thr Leu Trp Gly Asp Gly Val Val Glu Ser Glu
225                 230                 235                 240

Met Ile Ile Pro Val Thr Leu Gly Gly Pro Lys Ser His His Asn Lys
                245                 250                 255

Arg Asn Gly Tyr His Thr Gln Thr Lys Gly Pro Trp Ser Glu Gly Glu
                260                 265                 270

Ile Thr Leu Asp Phe Asp Tyr Cys Pro Gly Thr Thr Val Thr Val Thr
                275                 280                 285

Glu His Cys Gly Asn Arg Gly Ala Ser Leu Arg Thr Thr Thr Ala Ser
                290                 295                 300

Gly Lys Leu Val Thr Asp Trp Cys Cys Arg Ser Cys Ser Leu Pro Pro
305                 310                 315                 320

Leu Arg Tyr Thr Thr Lys Asp Gly Cys Trp Tyr Gly Met Glu Ile Arg
                325                 330                 335

Pro Val Lys Glu Glu Ala Lys Leu Val Lys Ser Arg Val Thr Ala
                340                 345                 350

<210> SEQ ID NO 141
<211> LENGTH: 352
<212> TYPE: PRT
<213> ORGANISM: Murray Valley encephalitis virus

<400> SEQUENCE: 141

Asp Thr Gly Cys Ala Ile Asp Ile Thr Arg Arg Glu Leu Lys Cys Gly
1               5                   10                  15

Ser Gly Ile Phe Ile His Asn Asp Val Glu Ala Trp Ile Asp Arg Tyr
                20                  25                  30

Lys Tyr Leu Pro Glu Thr Pro Lys Gln Leu Ala Lys Val Val Glu Asn
            35                  40                  45

Ala His Lys Ser Gly Ile Cys Gly Ile Arg Ser Val Asn Arg Phe Glu
    50                  55                  60

His Gln Met Trp Glu Ser Val Arg Asp Glu Leu Asn Ala Leu Leu Lys
65                  70                  75                  80

Glu Asn Ala Ile Asp Leu Ser Val Val Val Glu Lys Gln Lys Gly Met
                85                  90                  95

Tyr Arg Ala Ala Pro Asn Arg Leu Arg Leu Thr Val Glu Glu Leu Asp
            100                 105                 110

Ile Gly Trp Lys Ala Trp Gly Lys Ser Leu Leu Phe Ala Ala Glu Leu
        115                 120                 125

Ala Asn Ser Thr Phe Val Val Asp Gly Pro Glu Thr Ala Glu Cys Pro
130                 135                 140

Asn Ser Lys Arg Ala Trp Asn Ser Phe Glu Ile Glu Asp Phe Gly Phe
145                 150                 155                 160

Gly Ile Thr Ser Thr Arg Gly Trp Leu Lys Leu Arg Glu Glu Asn Thr
                165                 170                 175

Ser Glu Cys Asp Ser Thr Ile Ile Gly Thr Ala Val Lys Gly Asn His
            180                 185                 190

Ala Val His Ser Asp Leu Ser Tyr Trp Ile Glu Ser Gly Leu Asn Gly
        195                 200                 205

Thr Trp Lys Leu Glu Arg Ala Ile Phe Gly Glu Val Lys Ser Cys Thr
210                 215                 220
```

```
                   210                 215                 220
Trp Pro Glu Thr His Thr Leu Trp Gly Asp Ala Val Glu Thr Glu
225                 230                 235                 240

Leu Ile Ile Pro Val Thr Leu Ala Gly Pro Arg Ser Lys His Asn Arg
                245                 250                 255

Arg Glu Gly Tyr Lys Val Gln Val Gln Gly Pro Trp Asp Glu Asp
                260                 265                 270

Ile Lys Leu Asp Phe Asp Tyr Cys Pro Gly Thr Thr Val Thr Val Ser
                275                 280                 285

Glu His Cys Gly Lys Arg Gly Pro Ser Val Arg Thr Thr Thr Asp Ser
                290                 295                 300

Gly Lys Leu Val Thr Asp Trp Cys Cys Arg Ser Cys Thr Leu Pro Pro
305                 310                 315                 320

Leu Arg Phe Thr Thr Ala Ser Gly Cys Trp Tyr Gly Met Glu Ile Arg
                325                 330                 335

Pro Met Lys His Asp Glu Ser Thr Leu Val Lys Ser Arg Val Gln Ala
                340                 345                 350

<210> SEQ ID NO 142
<211> LENGTH: 352
<212> TYPE: PRT
<213> ORGANISM: Tick-borne encephalitis virus

<400> SEQUENCE: 142

Asp Val Gly Cys Ala Val Asp Thr Glu Arg Met Glu Leu Arg Cys Gly
1               5                   10                  15

Glu Gly Leu Val Val Trp Arg Glu Val Ser Glu Trp Tyr Asp Asn Tyr
                20                  25                  30

Ala Tyr Tyr Pro Glu Thr Pro Gly Ala Leu Ala Ser Ala Ile Lys Glu
                35                  40                  45

Thr Phe Glu Glu Gly Ser Cys Gly Val Val Pro Gln Asn Arg Leu Glu
                50                  55                  60

Met Ala Met Trp Arg Ser Ser Val Thr Glu Leu Asn Leu Ala Leu Ala
65                  70                  75                  80

Glu Gly Glu Ala Asn Leu Thr Val Val Asp Lys Phe Asp Pro Thr
                85                  90                  95

Asp Tyr Arg Gly Gly Val Pro Gly Leu Leu Lys Lys Gly Lys Asp Ile
                100                 105                 110

Lys Val Ser Trp Lys Ser Trp Gly His Ser Met Ile Trp Ser Ile Pro
                115                 120                 125

Glu Ala Pro Arg Arg Phe Met Val Gly Thr Glu Gly Gln Ser Glu Cys
                130                 135                 140

Pro Leu Glu Arg Arg Lys Thr Gly Val Phe Thr Val Ala Glu Phe Gly
145                 150                 155                 160

Val Gly Leu Arg Thr Lys Val Phe Leu Asp Phe Arg Gln Glu Pro Thr
                165                 170                 175

His Glu Cys Asp Thr Gly Val Met Gly Ala Ala Val Lys Asn Gly Met
                180                 185                 190

Ala Ile His Thr Asp Gln Ser Leu Trp Met Arg Ser Met Lys Asn Asp
                195                 200                 205

Thr Gly Thr Tyr Ile Val Glu Leu Leu Val Thr Asp Leu Arg Asn Cys
                210                 215                 220

Ser Trp Pro Ala Ser His Thr Ile Asp Asn Ala Asp Val Val Asp Ser
225                 230                 235                 240
```

```
Glu Leu Phe Leu Pro Ala Ser Leu Ala Gly Pro Arg Ser Trp Tyr Asn
            245             250                 255

Arg Ile Pro Gly Tyr Ser Glu Gln Val Lys Gly Pro Trp Lys Tyr Thr
            260             265                 270

Pro Ile Arg Val Ile Arg Glu Glu Cys Pro Gly Thr Thr Val Thr Ile
            275             280                 285

Asn Ala Lys Cys Asp Lys Arg Gly Ala Ser Val Arg Ser Thr Thr Glu
            290             295             300

Ser Gly Lys Val Ile Pro Glu Trp Cys Cys Arg Ala Cys Thr Met Pro
305             310                 315                 320

Pro Val Thr Phe Arg Thr Gly Thr Asp Cys Trp Tyr Ala Met Glu Ile
                325             330                 335

Arg Pro Val His Asp Gln Gly Gly Leu Val Arg Ser Met Val Val Ala
                340             345             350
```